US012599786B2

(12) United States Patent (10) Patent No.: US 12,599,786 B2

Krone et al. (45) Date of Patent: Apr. 14, 2026

(54) ULTRASOUND DEVICE WITH ATTACHABLE COMPONENTS

(71) Applicant: MADORRA INC., Portland, OR (US)

(72) Inventors: Ryan Taylor Krone, Portland, OR (US); Holly Elizabeth Rockweiler, Portland, OR (US); Lauren Paige Jones, Portland, OR (US); Eric Schultz, Portland, OR (US); Bryan Flaherty, Mountain View, CA (US)

(73) Assignee: Madorra Inc., Portland, OR (US)

( * ) Notice: Subject to any disclaimer, the term of this patent is extended or adjusted under 35 U.S.C. 154(b) by 258 days.

(21) Appl. No.: 17/628,341

(22) PCT Filed: Jul. 17, 2020

(86) PCT No.: PCT/US2020/042496

§ 371 (c)(1),
(2) Date: Jan. 19, 2022

(87) PCT Pub. No.: WO2021/016070

PCT Pub. Date: Jan. 28, 2021

(65) Prior Publication Data

US 2022/0249876 A1 Aug. 11, 2022

Related U.S. Application Data

(60) Provisional application No. 62/891,246, filed on Aug. 23, 2019, provisional application No. 62/876,459, filed on Jul. 19, 2019.

(51) Int. Cl.
A61N 7/02 (2006.01)
A61N 7/00 (2006.01)

(52) U.S. Cl.
CPC ........ A61N 7/02 (2013.01); *A61N 2007/0004* (2013.01)

(58) Field of Classification Search
CPC .............................................. A61N 2007/0004
See application file for complete search history.

(56) References Cited

U.S. PATENT DOCUMENTS

| | | | |
|---|---|---|---|
| 3,504,665 A | 4/1970 | Bakunin et al. | |
| 4,646,725 A | 3/1987 | Moasser | |
| (Continued) | | | |

FOREIGN PATENT DOCUMENTS

| | | |
|---|---|---|
| CN | 1778414 A | 5/2006 |
| CN | 102170938 A | 8/2011 |
| (Continued) | | |

OTHER PUBLICATIONS

Krone et al.; U.S. Appl. No. 18/054,062 entitled "Ultrasound device for vulvovaginal rejuvenation," filed Nov. 9, 2022.

(Continued)

*Primary Examiner* — Anh Tuan T Nguyen
*Assistant Examiner* — Tommy T Ly
(74) *Attorney, Agent, or Firm* — Shay Glenn LLP

(57) ABSTRACT

A handheld ultrasound device and corresponding methods, including devices and methods used for rejuvenating the vulvovaginal area of the user. In general, the handheld ultrasound devices include a device body coupled to an acoustic coupler and a handle. The device body further includes internal components including an ultrasound transducer, an energy delivery element, and circuitry for controlling the ultrasound output. In particular examples, the methods of using the handheld ultrasound device include engaging the tissue in and around the vulvovaginal area with the energy delivery element, applying ultrasound energy to the vulvovaginal tissue from the energy delivery element and through the acoustic coupler, and affecting a measurable parameter associated with vulvovaginal rejuvenation.

19 Claims, 65 Drawing Sheets

(56) References Cited

U.S. PATENT DOCUMENTS

| | | | | |
|---|---|---|---|---|
| 4,757,820 | A | 7/1988 | Itoh | |
| 4,938,217 | A | 7/1990 | Lele | |
| D316,376 | S | 4/1991 | Dubut | |
| 5,361,203 | A * | 11/1994 | Hiyama | G16H 30/20 |
| | | | | 385/117 |
| D389,918 | S | 1/1998 | Ninomiya et al. | |
| 5,827,203 | A | 10/1998 | Nita | |
| 6,169,914 | B1 | 1/2001 | Hovland et al. | |
| 6,221,021 | B1 | 4/2001 | Redano | |
| 6,741,895 | B1 | 5/2004 | Gafni et al. | |
| D705,433 | S | 5/2014 | Ran et al. | |
| 9,072,487 | B2 | 7/2015 | Hebrard et al. | |
| D763,452 | S | 8/2016 | Ryu et al. | |
| D847,353 | S | 4/2019 | Hasegawa et al. | |
| 10,543,382 | B2 | 1/2020 | Rockweiler et al. | |
| D897,543 | S | 9/2020 | Jones et al. | |
| 2002/0068900 | A1 | 6/2002 | Barnes et al. | |
| 2002/0091339 | A1 | 7/2002 | Horzewski et al. | |
| 2005/0049509 | A1 | 3/2005 | Mansour et al. | |
| 2005/0203399 | A1 | 9/2005 | Vaezy et al. | |
| 2005/0215901 | A1 | 9/2005 | Anderson et al. | |
| 2005/0216069 | A1 | 9/2005 | Cohen et al. | |
| 2005/0222273 | A1 | 10/2005 | Dodd | |
| 2006/0004290 | A1 * | 1/2006 | Smith | A61B 8/4483 |
| | | | | 600/459 |
| 2006/0100552 | A1 | 5/2006 | Schultheiss et al. | |
| 2006/0235303 | A1 | 10/2006 | Vaezy et al. | |
| 2007/0021809 | A1 | 1/2007 | Cole et al. | |
| 2007/0167820 | A1 | 7/2007 | Hirayama et al. | |
| 2007/0179413 | A1 | 8/2007 | Imboden et al. | |
| 2007/0197918 | A1 | 8/2007 | Vitek et al. | |
| 2007/0233191 | A1 | 10/2007 | Parmer | |
| 2009/0043248 | A1 | 2/2009 | Peterson et al. | |
| 2009/0171138 | A1 | 7/2009 | Eli | |
| 2011/0040187 | A1 | 2/2011 | Matsumura | |
| 2011/0087107 | A1 | 4/2011 | Lindekugel et al. | |
| 2011/0313293 | A1 | 12/2011 | Lindekugel et al. | |
| 2012/0065501 | A1 | 3/2012 | Dae et al. | |
| 2012/0108918 | A1 * | 5/2012 | Jarvik | A61B 5/4827 |
| | | | | 600/301 |
| 2012/0143062 | A1 | 6/2012 | Nordgren et al. | |
| 2012/0289858 | A1 | 11/2012 | OuYang et al. | |
| 2013/0158397 | A1 | 6/2013 | Varna et al. | |
| 2013/0190661 | A1 | 7/2013 | Wing et al. | |
| 2013/0301395 | A1 | 11/2013 | Bahl et al. | |
| 2013/0303904 | A1 | 11/2013 | Barthe et al. | |
| 2013/0338503 | A1 | 12/2013 | Cohen et al. | |
| 2013/0338545 | A1 | 12/2013 | Azhari et al. | |
| 2014/0163437 | A1 | 6/2014 | Mack et al. | |
| 2014/0180116 | A1 | 6/2014 | Lindekugel et al. | |
| 2014/0257145 | A1 | 9/2014 | Emery | |
| 2015/0126810 | A1 | 5/2015 | Wood et al. | |
| 2015/0135840 | A1 | 5/2015 | Sato et al. | |
| 2015/0217141 | A1 * | 8/2015 | Barthe | A61N 7/00 |
| | | | | 601/2 |
| 2015/0231415 | A1 | 8/2015 | Lewis, Jr. et al. | |
| 2016/0030083 | A1 | 2/2016 | Blurton et al. | |
| 2016/0128670 | A1 | 5/2016 | Morgan | |
| 2016/0242736 | A1 | 8/2016 | Freiburg | |
| 2016/0287334 | A1 * | 10/2016 | Grant | A61B 18/02 |
| 2017/0065289 | A1 | 3/2017 | Hsu et al. | |
| 2017/0143997 | A1 * | 5/2017 | Rockweiler | A61B 5/4836 |
| 2017/0303857 | A1 | 10/2017 | Perkins et al. | |
| 2018/0104514 | A1 * | 4/2018 | Gertner | A61H 23/0263 |
| 2018/0140277 | A1 | 5/2018 | Pelissier et al. | |
| 2018/0196130 | A1 | 7/2018 | Okawa | |
| 2018/0240548 | A1 * | 8/2018 | Spohn | G16H 40/63 |
| 2019/0060675 | A1 | 2/2019 | Krone et al. | |
| 2019/0223837 | A1 | 7/2019 | Petrossian et al. | |
| 2019/0269943 | A1 * | 9/2019 | Lewis, Jr | G10K 11/02 |
| 2019/0274714 | A1 * | 9/2019 | Cuti | A61B 90/08 |
| 2020/0171329 | A1 | 6/2020 | Rockweller et al. | |
| 2022/0226471 | A1 * | 7/2022 | Marcus | A61B 5/4848 |
| 2023/0277216 | A1 | 9/2023 | Blante et al. | |

FOREIGN PATENT DOCUMENTS

| | | | | |
|---|---|---|---|---|
| CN | 102397633 | A | 4/2012 | |
| DE | 19509004 | C1 | 10/1996 | |
| EP | 2839804 | A2 | 2/2015 | |
| EP | 3179313 | A1 | 6/2017 | |
| JP | 2001340416 | A | 12/2001 | |
| JP | 2009028296 | A | 2/2009 | |
| JP | 2011167316 | A | 9/2011 | |
| WO | WO-0078232 | A1 * | 12/2000 | A61N 7/02 |
| WO | WO2007/092610 | A2 | 8/2007 | |
| WO | WO2011/082402 | A2 | 7/2011 | |
| WO | WO2012/081011 | A1 | 6/2012 | |
| WO | WO2013/048912 | A2 | 4/2013 | |
| WO | WO2013/184798 | A1 | 12/2013 | |
| WO | WO2013/188625 | A1 | 12/2013 | |
| WO | WO2015/130841 | A1 | 9/2015 | |
| WO | WO2020/026254 | A1 | 2/2020 | |

OTHER PUBLICATIONS

Chin et al.; The prevalence and severity of urogenital symptoms in postmenopausal women receiving endocrine therapy for breast cancer; Journal of Clinical Oncology; Meeting Abstract; 26(15 suppl); pp. 20551; May 2008.

Kaplan et al.; U.S. Appl. No. 18/553,486 entitled "Ultrasound device for vulvovaginal rejuvenation," filed Sep. 29, 2023.

Baker et al.; The effect of therapeutic modalities on blood flow in the human calf; Journal of Orthopaedic and sports Physical Therapy; 13(1); pp. 23-27; Jan. 1991.

Bishop et al.; Human tissue—temperature rise during ultrasound treatments with the aquaflex gel pad; Journal of Athletic Training; 39(2); pp. 126-131; Apr. 1, 2004.

breastcancer.org; U.S. breast cancer statistics; 2 pages; retrieved from the internet (http://www.breastcancer.org/symptoms/understand_bc/statistics); Last Modified Jun. 23, 2016.

Cao et al.; Measurements of female genital appearance in chinese adults seeking genital cosmetic surgery: a preliminary report from a gynecological center; Int. Urogynecol.; 26(5); pp. 729-735; Nov. 2014 (online).

Chin et al.; Prevalence and severity of urogenital symptoms in postmenopausal women receiving endocrine therapy for breast cancer; Clinical Breast Cancer; 9(2); pp. 108-117; May 31, 2009.

Chin et al.; The prevalence and severity of urogenital symptoms in postmenopausal women receiving endocrine therapy for breast cancer; Journal of Clinical Oncology; 26(15 suppl); pp. 20551; May 2008.

Committee on Practice Bulletins _ Gynecology; Acog Practice Bulletin No. 126: Management of gynecologie issues in women with breast cancer; Obstet Gynecol.; 119(126); pp. 666-682; Mar. 2012.

Dalecki; Mechanical bioeffects of ultrasound; Annu. Rev. Biomed. Eng.; 6; pp. 229-248; Aug. 15, 2004.

Ferguson; Ultrasound in the treatment of surgical wounds; Physiotherapy; 67(2); p. 43; Feb. 10, 1981.

Ganz et al.; Implementing a survivorship care plan for patients with breast cancer; Journal of Clinical Oncology; 26(5); pp. 759-767; Feb. 2008.

Hutchinson et al.; Intracavitary ultrasound phased arrays for non-invasive prostate surgery; IEEE transactions on ultrasonics, Ferroelectrics, and Frequency Control; 43(6); pp. 1032-1042; Nov. 1996.

Julien et al.; Identification of barriers to sexual health assessment in oncology nursing practice; Oncology Nursing Forum; 37(3); pp. E186-E190; May 2010.

Kingberg et al.; Vulvar and vaginal atrophy in postmenopausal women: findings from the REVIVE (Real Women's Views of Treatment Options for Menopausal Vaginal Changes) Survey; The Journal of Sexual Medicine; 10(7); pp. 1790-1799; Jul. 1, 2013.

Levin; The physiology of sexual arousal in the human female: a recreational and procreational synthesis; Archives of Sexual Behavior; 31(5); pp. 405-411; Oct. 2002.

(56)  References Cited

OTHER PUBLICATIONS

Lloyd et al.; Female genital appearance: 'normality' unfolds *; BJOG: an International Journal of Obstetrics and Gynaecology; 112; pp. 643-646; May 2005.

Macbride et al.; Vulvovaginal atrophy; Mayo Clinic Proceedings; 85(1); pp. 87-94; Jan. 2010.

Michlovitz et al.; Modalities for therapeutic intervention (contemporary perspectives in rehabilitation); 5th Edition; F.A. Davis Company; Chapter 5 Therapeutic Ultrasound; p. 91-92; Jun. 21, 2011.

Noble; Physical therapy in gyn: Ultrasound postpartum; 2 pgs.; (this information available to applicant(s) at least as of Jan. 14, 2015).

Nyborg; Biological effects of ultrasound: development of safety guidelines. Part II: general review; Ultrasound in Med. & Biol.; 27(3); pp. 301-333; Mar. 31, 2001.

PRWEB; Breast cancer therapeutics market worth $13.1 billion by 2020 says a new research report at reportsnreports.com; 4 pages; retrieved Aug. 5, 2020 from the internet (http://www.prweb.com/releases/breast-cancer-therapeutic/market-2020-forecasts/prweb11922634.htm); Jun. 7, 2014.

Rellini et al.; The sensitivity of event logs, self-administered questionnaires and photoplethysmography to detect treatment-induced changes in female sexual arousal disorder (FSAD) diagnosis; The Journal of Sexual Medicine; 3(2); pp. 283-291; 14 pages (Author Manuscript); Mar. 2006.

Rosen et al.; The female sexual function index (FSFI): a multidimensional self-report instrument for the assessment of female sexual function; Journal of Sex and Marital Therapy; 26(2); pp. 191-208; Apr. 2000.

Rossouw et al.; Risks and benefits of estrogen plus progestin in healthy postmenopausal women: principal results from the women's health initiative randomized controlled trial; JAMA; 288(3); pp. 321-333; Jul. 17, 2002.

Salani et al.; Gynecologic care for breast cancer survivors assisting in the transition to wellness; American Journal of Obstetrics and Gynecology; 206(5); pp. 390-397; May 2012.

Soneson; HIFU simulator v1.2 user's manual; US Food and Drug Administration; 17 pages; Jan. 30, 2011.

Szabo; Diagnostic Ultrasound Imaging: Inside Out, 2nd Edition; Chapter 5: Transducers; pp. 121-165; Academic Press; Dec. 2013.

Wadler; I was misinformed: what price love?; The New York Times; 2 pages; retrieved Aug. 5, 2020 from the internet (https://www.nytimes.com/2013/12/04/booming/what-price-love.html) ; Dec. 2013.

Writing Group for the Women's Health Initiative Investigators; Risks and benefits of estrogen plus progestin in healthy postmenopausal women: principals results from women health initiative randomized controlled trial; Journal America Medical Association; 288(3); pp. 321-333; Jul. 2002.

Young et al.; The effect of therapeutic ultrasound on angiogenesis; Ultrasound in Med. & Biol.; 16(3); pp. 261-269; Jan. 1, 1990.

Zethraeus et al.; The impact of hormone replacement therapy on quality of life and willingness to pay; British Journal of Obstetrics and Gynaecology; 104(10); pp. 1191-1195; Oct. 1997.

Normand et al.; New insight into agarose gel mechanical properties; Biomacromolecules; 1(4); pp. 730-738; Dec. 12, 2000.

* cited by examiner

*100*

CONDUCTIVE CHARGING

*100*

INDUCTIVE CHARGING

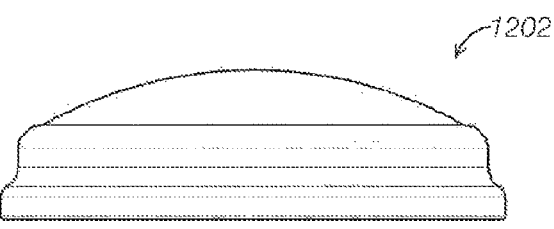
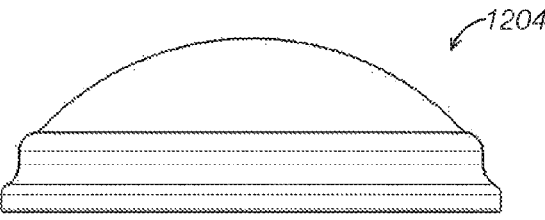
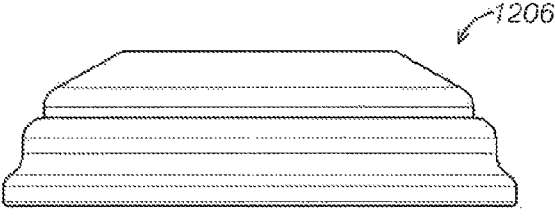
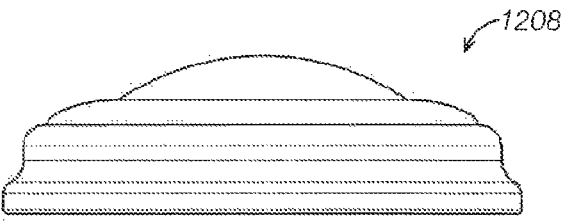
FIG. 12

2902

2904

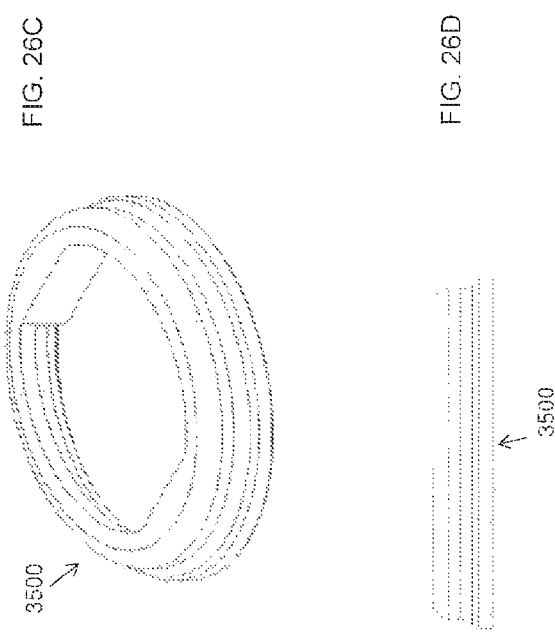
FIG. 26C
FIG. 26D
3500
3500
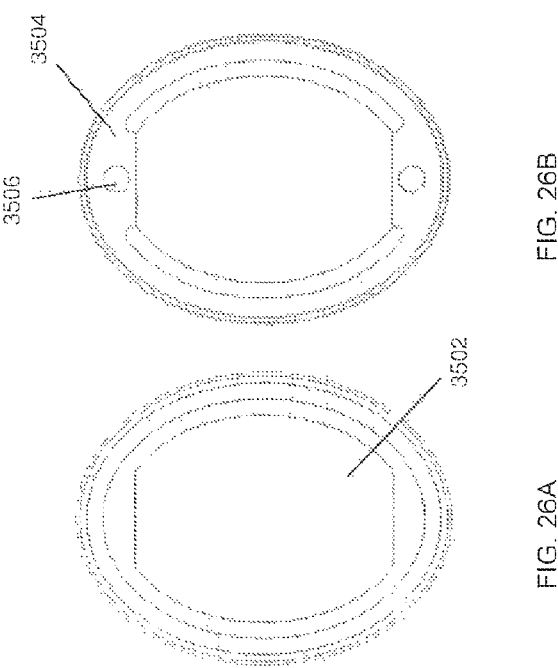
3504
3506
3502
FIG. 26B
FIG. 26A

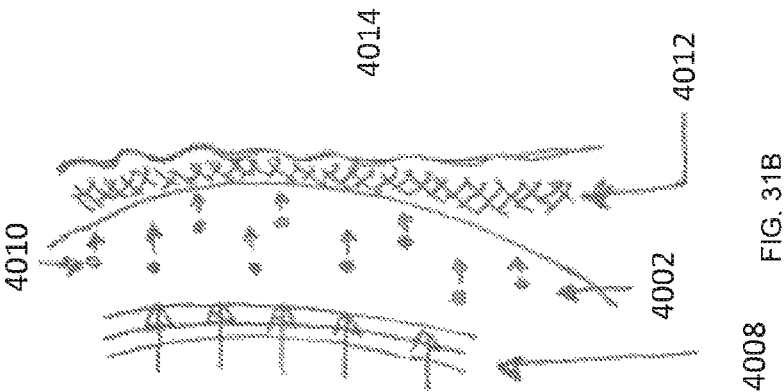
FIG. 31B
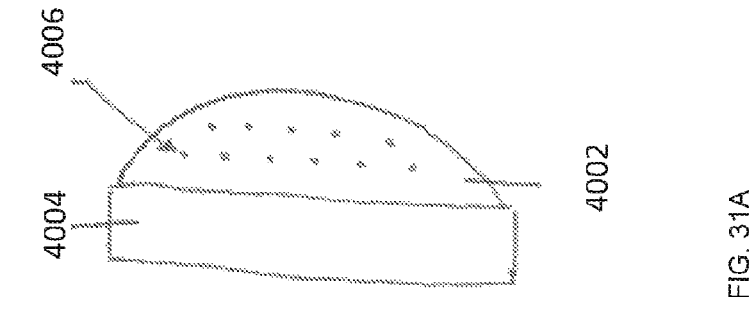
FIG. 31A
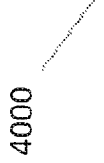

4400

4402

4400

4400

4400

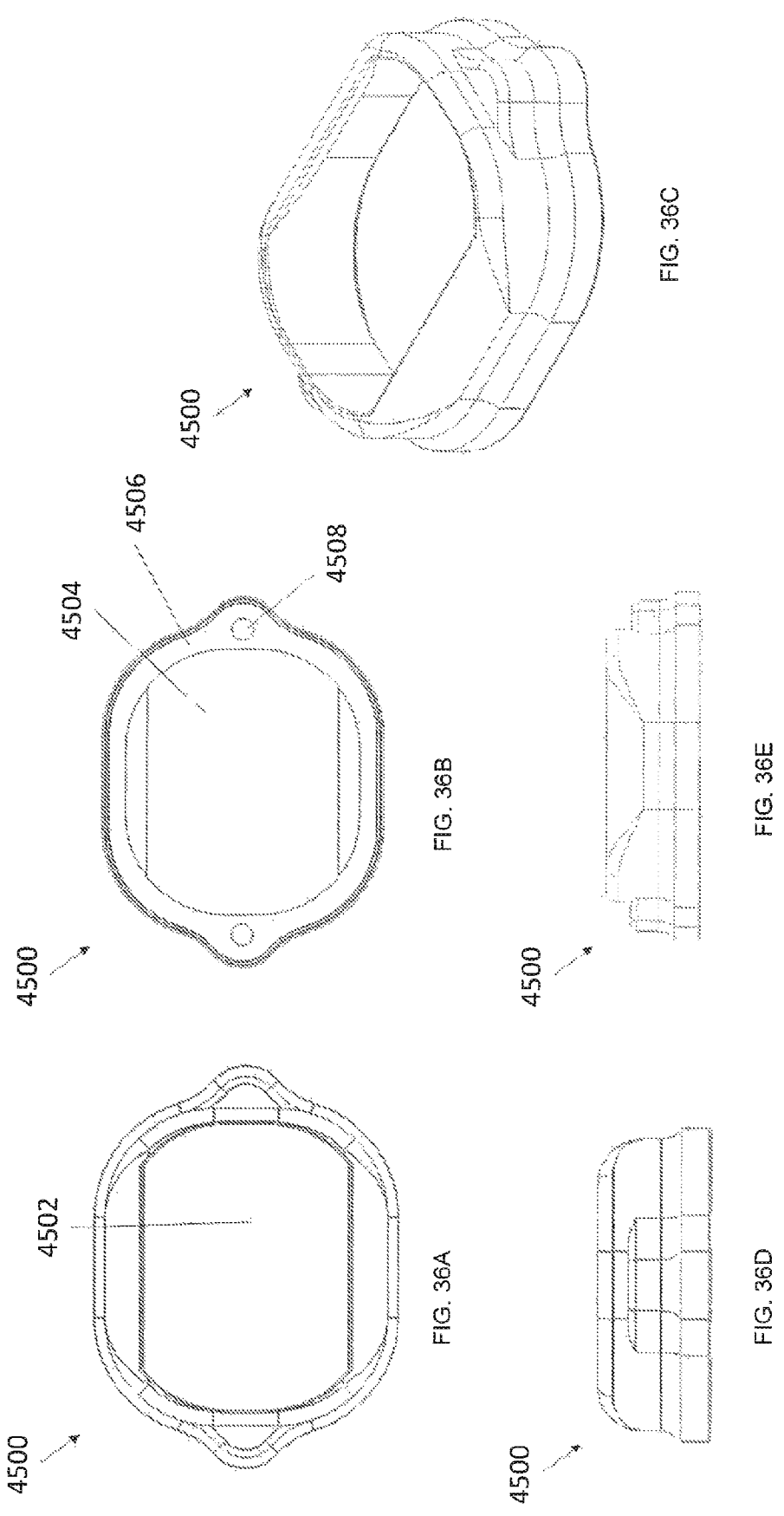

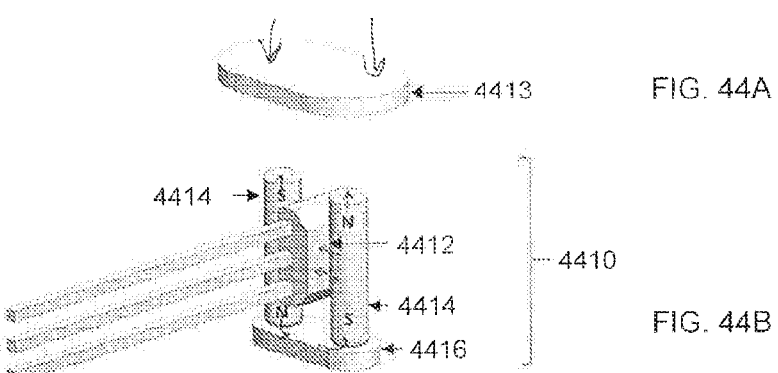
4413
FIG. 44A
4414
4412
4410
4414
4416
FIG. 44B
4420
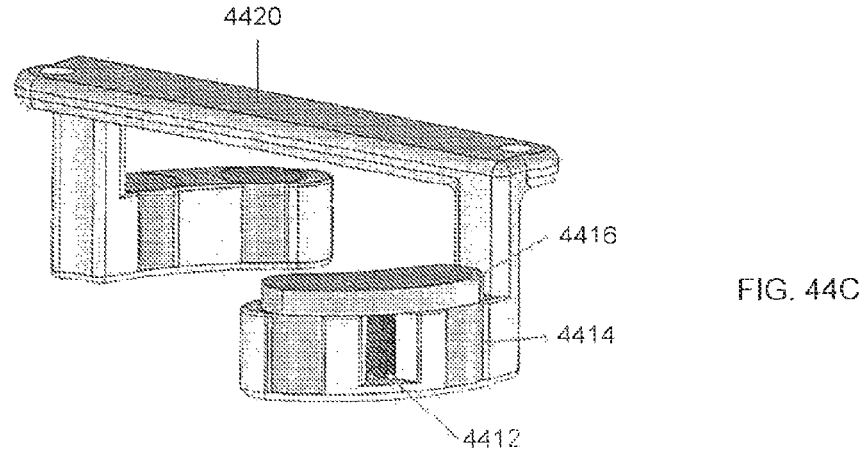
4416
4414
4412
FIG. 44C

4812

OPTICAL
READER

CODE AREA ON
SUPPORT RING

ULTRASOUND DEVICE WITH ATTACHABLE COMPONENTS

CROSS REFERENCE TO RELATED APPLICATIONS

This application claims priority to U.S. Provisional Patent Application No. 62/891,246, entitled "ULTRASOUND DEVICE FOR VULVOVAGINAL REJUVENATION" filed Aug. 23, 2019 and U.S. Provisional Patent Application No. 62/876,459, entitled "HAND HELD DEVICE TO TREAT VAGINAL DRYNESS AND ATROPHY" filed Jul. 19, 2019, each of which is herein incorporated by reference in its entirety.

This application relates to U.S. Patent Application Publication No. 2009/0060675 A1, entitled "ULTRASOUND DEVICE FOR VULVOVAGINAL REJUVENATION" filed Oct. 14, 2016, which is herein incorporated by reference in its entirety. This application may also be related to PCT Publication No. WO2015116512, entitled "DEVICE AND METHOD TO TREAT VAGINAL ATROPHY" filed Jan. 26, 2015, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Handheld medical ultrasound devices for applying ultrasonic energy to a subject. In some instances, the devices are designed for use in the genital area for treating vulvovaginal atrophy.

BACKGROUND

Vulvovaginal atrophy is an inflammation of the vagina, vulva, and outer urinary tract due to thinning and shrinking of these tissues. Vulvovaginal atrophy also may cause a decrease in lubrication in the vulvovaginal area. As a result, women experiencing vulvovaginal atrophy may not only suffer from decreased sexual enjoyment and day-to-day discomfort due to the lack of lubrication in the vulvovaginal area, but also discomfort during urination and urinary incontinence.

Factors that are known to contribute to vulvovaginal atrophy include menopause, treatments for breast cancer including chemotherapy and for some women, breastfeeding. In all of these causes, a change in the estrogen hormone level is a major contributor to vulvovaginal atrophy.

Until recently, there were limited options for women suffering from vulvovaginal atrophy. Vaginal moisturizers and lubricants only offer temporary relief and often do not provide enough symptomatic relief. Hormone replacement products, either applied locally or systematically, may also be an option, but involve risk of adverse side effects associated with their use. For example, hormone replacement therapies have common side effects such as nausea, vomiting, bloating, weight changes, and in addition may increase the user's risk of certain cancers and cardiovascular events. Furthermore, these types of hormone-based treatments are not recommended for women with, or who are survivors of, breast, ovarian, or endometrial cancers, and are contraindicated for women with a history of stroke or myocardial infarction because of these risks.

More recently, the drug Osphena®, a selective estrogen-receptor modulator that acts on specific estrogen receptors but is not itself a hormone, has become available. Osphena is a daily pill approved for dyspareunia in postmenopausal women; however, the drug acts like estrogen in the body and is currently not recommended for survivors of breast, ovarian or endometrial cancer due to the risk of cancer recurrence. Furthermore, women taking Osphena have experienced varying effects on improving vaginal dryness and have even experienced adverse side effects such as puffiness and redness on various parts of their bodies, severe hot flashes, and weight gain to name a few.

Also recently introduced is the MonaLisa Touch® from DEKA Medical Lasers. This therapy uses a transvaginal, $CO_2$ fractional laser to stimulate collagen production in the vaginal tissue over the course of three outpatient procedures. While early data from their first US clinical trial looks promising, the therapy has been slow to gain adoption because of its expense, invasive nature, and lack of multi-year safety data.

There is currently no safe, drug-free and highly effective FDA-approved solution for rejuvenating the thin, dry and inelastic vaginal tissue associated with vulvovaginal atrophy. The devices and methods described herein have been tested clinically and have shown compelling evidence of safety and efficacy as a treatment for vulvovaginal atrophy in both cancer survivors and pre-, peri-, and post-menopausal women. Further, there are currently no easy-to-use devices for treating vulvovaginal atrophy, for example, where a user can use at home.

BRIEF DESCRIPTION OF THE DRAWINGS

The novel features are set forth with particularity in the claims that follow. A better understanding of the features and advantages will be obtained by reference to the following detailed description that sets forth illustrative embodiments and the accompanying drawings.

FIGS. 1A and 1B are side views of two possible embodiments of the handheld ultrasound device. FIG. 1C is a drawing depicting a front view of the handheld ultrasound device.

FIG. 12 shows side views of various embodiments of coupling pads.

FIGS. 26A-26I show various views of an embodiment of a support ring of a coupling pad component.

FIGS. 31A and 31B illustrate further embodiments of a coupling pad component.

FIGS. 36A-36E show various views of an embodiment of a top portion of a coupling pad holder.

FIGS. 44A-44C show embodiments of a sensor assembly.

SUMMARY

Figure 1C:
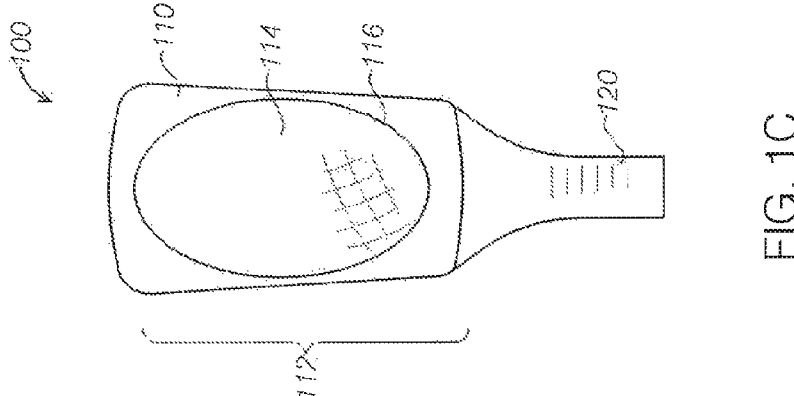
FIGS. 1A-1C show drawings of a handheld ultrasound device.

Described herein are ultrasound devices with features that make the devices easy to use and effective for delivering ultrasound energy in a prescribed manner. The devices can include a main component, which includes a hand-held ultrasound generator, and a disposable component that is attachable to the main component. In some cases, the devices are used to deliver therapeutic ultrasound treatment to a subject's vaginal region. The disposable component can include a pad adapted to contact external genital tissue around the subject's vagina. The pad can be configured to efficiently deliver ultrasound energy from the main component to the subject's tissue. To use the device, the device can be held up to the opening of the vaginal canal (introitus). Without penetrating the vaginal canal, the ultrasound generator can direct ultrasound energy along the vaginal canal to induce local heating, increase vaginal blood flow, and increase vaginal lubrication. Increased vaginal lubrication may be noticeable with a few minutes of daily use The main component may include one or more sensors for detecting attachment to the disposable component. In some examples, the device includes one or more magnetic sensors (e.g., Hall effect magnetic field sensor or a magneto-resistive sensor) for detecting magnetic attachment to the disposable component. The one or more sensors may be sealed within the device to protect the one or more sensors from moisture or other contaminants that may damage the one or more sensors. In some cases, the main component is configured to detect attachment of the disposable component. The main component may include a code reader (e.g., optical code reader) for reading a code on the disposable component to verify that the disposable component meets required specifications and/or is unused.

The devices can include features to provide easy use by a consumer. These features include the size, shape, materials, packaging, user interface, ultrasounds settings and transducer configuration. These features can also improve safety and reliability of the device. The devices can include software and/or firmware adapted to prevent tissue overheating and to ensure proper device use.

In some cases, the devices and methods are adapted to treat vaginal dryness, a condition in which the vaginal tissue becomes thin, dry, and inelastic, leading to day-to-day discomfort and pain with intercourse for women. The devices and methods can also be used to rejuvenate thin, dry and inelastic vaginal tissue associated with vulvovaginal atrophy. The treatments using the devices and methods may be non-hormonal, thereby avoiding risk factors and side effects associated with hormonal therapies. The devices may be home-use devices, thereby allowing women to apply treatment in the privacy of home. The devices are designed to effectively deliver the desired therapy directly to the vaginal tissue while being easy to use.

According to some aspects, a device for treating vaginal tissue atrophy in a female subject includes: a reusable component including an ultrasound transducer assembly, a controller configured to drive the ultrasound transducer assembly, and a coupling interface having at least one coupling element; and a disposable component including a coupling pad and a support, the coupling pad including a deformable coupling structure adapted to contact external genital tissue around the subject's vagina and geometric features configured to mate the coupling pad with the ultrasound transducer assembly, the support including at least one complementary coupling element the support adapted to reversibly attach to the coupling interface based on the interaction of the at least one coupling element and the at least one complementary coupling element; wherein the ultrasound transducer assembly and coupling pad being adapted, when the reusable component and the disposable component are attached together, to deliver ultrasound energy to the subject to increase blood flow to internal vaginal tissue to an increased level above a baseline level of blood flow to the internal vaginal tissue such that the increased level of blood flow to the internal vaginal tissue persists after energy application ceases; wherein the coupling interface can be adapted to attach the support to the coupling interface. The coupling element can include one or more sensors adapted to detect attachment of the disposable component to the reusable component. The one or more sensors can be sealed within the reusable component to protect the one or more sensors from moisture. The one or more sensors can be in communication with communication with the controller and adapted to provide feedback regarding quality and sufficiency of contact between the reusable component and the disposable component. The one or more sensors can include at least one magnetic sensor adapted to sense coupling with at least one coupling element complementary to the at least one magnetic sensor. The at least one magnetic sensor can be on the disposable component and the at least one coupling element can be on the reusable component. The at least one magnetic sensor can be on the reusable component and the at least one coupling element can be on the disposable component. The one or more sensors can include a Hall effect magnetic field sensor, a magneto-resistive sensor, or a Hall effect magnetic field sensor and a magneto-resistive sensor. The ultrasound transducer assembly can be adapted to deliver ultrasound energy at a frequency of between about 0.5 MHz and 4 MHz. The ultrasound transducer assembly can be adapted to deliver ultrasound energy at an intensity of between about 0.25 W/cm2 and 5 W/cm2. The ultrasound transducer assembly can be adapted to deliver ultrasound energy at a duty cycle in a range of about 20%-80%. The device can further include a sensor adapted and configured to measure a physiologic parameter of tissue in or around the subject's vagina when the ultrasound transducer assembly can be engaged with tissue in or around the subject's vagina, the device being further configured to use information from the sensor to control energy delivery from the ultrasound transducer assembly. The physiologic parameter can be temperature, blood flow, or vaginal lubrication. The coupling pad can include a gel. The coupling pad can include at least one of silicone rubber, soft plastics, fabrics, and flexible foams. The device can further include a feedback mechanism configured to provide feedback to the subject regarding quality and sufficiency of contact between the ultrasound transducer assembly and the coupling pad. The feedback mechanisms can include at least one of snap sounds and an alarm. The device can further include a feedback mechanism configured to provide feedback to the subject regarding quality and sufficiency of contact between the coupling pad and the subject's tissue. The at least one coupling element and the at least one complementary coupling element can be isolated from the environment. The at least one coupling element and the at least one complementary coupling element can be coated with a hydrophilic coating. The at least one coupling element and the at least one complementary coupling element can be coated with a hydrophobic coating. The at least one coupling element and the at least one complementary coupling element can be coated with Parylene. The at least one coupling element can be molded into the coupling interface, and the at least one complementary coupling element can be molded into the support. When the support is attached to the coupling interface, the at least one coupling element and the at least one complementary coupling element can generate a connection force of about 2 to 6 Newtons. The controller can be configured to only drive the ultrasound transducer assembly when the one or more sensors detects attachment of the disposable component to the reusable component. The one or more sensors can include a magneto-resistive sensor, wherein the device can further include a pair of magnets positioned on either side of the at least one magneto-resistive sensor, wherein the pair of magnets can have opposite orientations of polarity, and wherein a metallic connector can be attached to one side of the pair of magnets. The one or more sensors can include a magneto-resistive sensor, wherein the device can further include a common sensor assembly including a frame with at least one receptacle for the at least one magneto-resistive sensor and at least one receptacle for the at least one complementary coupling element. The reusable component can have a handle portion having a longitudinal axis, wherein the ultrasound transducer assembly can have a transducer face that has a normal vector that can be oriented between about 90 to 180 degrees to the longitudinal axis. The reusable component can have a handle portion having a longitudinal axis, wherein the ultrasound transducer assembly can have a transducer face having a normal that can be oriented about 115 degrees to the longitudinal axis. The coupling interface can have a surface that can be parallel to the transducer face. The handle portion can include one or more visual markings or protrusions on a side of the handle portion that can be visible to the female subject when the coupling pad is placed against the female subject's external genital tissue, wherein when the one or more visual markings or protrusions are aligned with one or more anatomical features of the female subject and the coupling pad is placed against the female subject's external genital tissue, the normal of the transducer face can be aligned within about 30 degrees of a longitudinal axis that extends through the female subjects vaginal canal. The at least one coupling element can be metal or magnetic and the at least one complementary coupling element can be metal or magnetic.

According to some aspects, a device for treating vaginal atrophy includes: a reusable component including an ultrasound transducer assembly, a controller configured to drive the ultrasound transducer assembly, and a transducer face, the reusable component including a handle portion; and a disposable component including a coupling pad and a support, the coupling pad including a deformable coupling structure adapted to contact external genital tissue around the subject's vagina and geometric features configured to mate the coupling pad with the ultrasound transducer assembly; wherein the ultrasound transducer assembly and coupling pad being adapted, when the reusable component and the disposable component are attached together, to deliver ultrasound energy to the subject to increase blood flow to internal vaginal tissue to an increased level above a baseline level of blood flow to the internal vaginal tissue such that the increased level of blood flow to the internal vaginal tissue persists after energy application ceases, and wherein the handle portion can include one or more visual markings or protrusions on a side of the handle portion that can be visible to the female subject when the coupling pad is placed against the female subject's external genital tissue, wherein when the one or more visual markings or protrusions are aligned with one or more anatomical features of the female subject and the coupling pad is placed against the female subject's external genital tissue, the normal of the transducer face can be aligned within about 30 degrees of a longitudinal axis that extends through the female subjects vaginal canal. The reusable component can be configured for blind placement by a user. The ultrasound transducer assembly can be adapted to deliver ultrasound energy at a frequency of between about 0.5 MHz and 4 MHz. The ultrasound transducer assembly can be adapted to deliver ultrasound energy at an intensity of between about 0.25 W/cm2 and 5 W/cm2. The ultrasound transducer assembly can be adapted to deliver ultrasound energy at a duty cycle in a range of about 20%-80%. The device can further include a sensor adapted and configured to measure a physiologic parameter of tissue in or around the subject's vagina when the ultrasound transducer assembly can be engaged with tissue in or around the subject's vagina, the device being further configured to use information from the sensor to control energy delivery from the ultrasound transducer assembly. The physiologic parameter can be temperature, blood flow, or vaginal lubrication. The coupling pad can include a gel. The coupling pad can include at least one of silicone rubber, soft plastics, fabrics, and flexible foams. The device can further include a feedback mechanism configured to provide feedback to the subject regarding quality and sufficiency of contact between the ultrasound transducer assembly and the coupling pad. The feedback mechanisms can include at least one of snap sounds and an alarm. The device can further include a feedback mechanism configured to provide feedback to the subject regarding quality and sufficiency of contact between the coupling pad and the subject's tissue. The device can be configured to be held vertically relative to a surface on which the user can be positioned. The device can be configured to be held in line with the user's navel. The configuration of the device can enable blind placement by a user.

According to some aspects, a device for applying ultrasonic energy to a subject includes: a disposable component including an optically readable code, wherein the optically readable code can include encoded identification information associated with the disposable component; and a reusable component including an ultrasound transducer assembly and a code reader assembly adapted to detect the optically readable code of the disposable component, wherein the reusable component can be adapted to verify that the disposable component corresponds to a pre-approved disposable component, that the disposable component is unused, or that the disposable component corresponds to a pre-approved disposable component and is unused, wherein when the reusable component and the disposable component are attached together, the ultrasound transducer assembly and the disposable component can be adapted to deliver ultrasound energy to the subject. The reusable component and the disposable component can be adapted to deliver the ultrasound energy for imaging internal body structures of the subject. The reusable component and the disposable component can be adapted to deliver a therapeutic ultrasound energy to one or more tissues of the subject. The reusable component and the disposable component can be adapted to deliver a therapeutic ultrasound energy to the subject's genital tissue. The disposable component can include a coupling pad adapted to contact external genital tissue around the subject's vagina. The reusable component and the disposable component can be adapted to deliver a therapeutic ultrasound energy to increase blood flow to internal vaginal tissue to an increased level above a baseline level of blood flow to the internal vaginal tissue such that the increased level of blood flow to the internal vaginal tissue persists after energy application ceases. The disposable component can include geometric features configured to mate the coupling pad with the ultrasound transducer assembly. The code reader assembly can be adapted to emit light to illuminate the optically readable code. The code reader assembly can be adapted to emit infrared light. The optical reader assembly operates at a focal distance ranging from about 1 millimeter (mm) to about 12 mm. The disposable component can include a coupling pad including a gel. The gel can include one or more of an acoustic conductive gel, a polymer hydrogel, an agar, a pectin, and a carrageenan. The coupling pad can include at least one of silicone rubber, soft plastics, fabrics, and flexible foams. A housing of the reusable component can include a window through which the code reader assembly transmits and receives light. The window can be on a head portion of the reusable component, the head portion including a transducer head of the ultrasound transducer assembly. The window can be on a transducer face of the head portion, wherein the transducer face can be adapted to contact a support of the disposable component when the disposable component can be properly attached to the reusable component. The optically readable code can be on the support of the disposable component. The support can have a ring shape or oval shape. The reusable component can include a handle portion, wherein the handle portion can include one or more visual markings or protrusions on a side of the handle portion that can be visible to the subject when the coupling pad is placed against the subject's female external genital tissue. When the one or more visual markings or protrusions are aligned with one or more anatomical features of the subject and a coupling pad of the disposable component is placed against the subject's female external genital tissue, the normal of a transducer face of the ultrasound transducer assembly can be aligned within about 30 degrees of a longitudinal axis that extends through the subject's vaginal canal. The device can further include a strain gauge to inform a user whether the disposable component can be being placed into sufficient contact with a treatment area of the subject. The strain gauge can provide feedback to the user as to a quality and sufficiency of contact between the disposable component and the treatment area of the subject. The device can be configured to provide feedback to a user indicating that the disposable component can be properly attached to the reusable component. The feedback can include at least one of a snap sound and an alarm. The device can be configured to be held vertically relative to a surface on which the subject can be positioned. The device can be configured to be held in line with the subject's navel.

According to some aspects, a method of applying ultrasonic energy to a subject includes: verifying an optically readable code on a disposable component using an optical reader assembly of an ultrasound device, wherein the verifying can include determining that the disposable component corresponds to a pre-approved disposable component, that the disposable component is unused, or that the disposable component corresponds to a pre-approved disposable component and is unused; and delivering the ultrasonic energy to the subject using the ultrasonic device with the disposable component attached thereto. The method can further include detecting ultrasonic energy reflected off of tissue of the subject to create images of the tissue. The ultrasonic energy can be adapted to deliver a therapeutic dose of ultrasound energy to one or more tissues of the subject. The therapeutic dose of ultrasound energy can be delivered to the subject's genital tissue. Delivering the therapeutic dose of ultrasonic energy can increase blood flow to internal vaginal tissue to an increased level above a baseline level of blood flow to the internal vaginal tissue such that the increased level of blood flow to the internal vaginal tissue persists after the applied ultrasonic energy ceases. The disposable component can include a coupling pad including a deformable coupling structure adapted to contact external genital tissue around the subject's vagina. The reusable component can include geometric features configured to mate the coupling pad with the ultrasound device. The method can further include determining that the disposable component can be properly attached to the ultrasound device prior to delivering the ultrasonic energy to the subject. The determining can include verifying sufficient contact between the disposable component and the ultrasound device. The determining can include detecting attachment of the disposable component to the ultrasound device using one or more magnetoresistive sensors. The method can further include providing feedback to the subject indicating that the disposable component can be properly attached to the ultrasound device. The disposable component can include a ring-shaped support that supports a coupling pad. The verifying can include receiving identification information associated with the disposable component from the optical reader assembly based on the optically readable code.

According to some aspects, a device for applying ultrasonic energy to a subject includes: a computer readable medium having instructions stored therein that, when executed by a processor of the device, cause the processor to perform operations including: verifying an optically readable code on a disposable component using an optical reader assembly of an ultrasound device, wherein the verifying can include determining that the disposable component corresponds to a pre-approved disposable component, that the disposable component is unused, or that the disposable component corresponds to a pre-approved disposable component and is unused; and delivering the ultrasonic energy to the subject using the ultrasonic device with the disposable component attached thereto. The ultrasound energy can be adapted for imaging internal body structures of the subject. The ultrasound energy can include a therapeutic dose of ultrasound energy delivered to one or more tissues of the subject. The ultrasound can include a therapeutic dose of ultrasound energy delivered to the subject's genital tissue. The ultrasound can include a therapeutic dose of ultrasound energy delivered to the subject's genital tissue, the delivered therapeutic dose of ultrasound energy can increase blood flow to internal vaginal tissue to an increased level above a baseline level of blood flow to the internal vaginal tissue such that the increased level of blood flow to the internal vaginal tissue persists after the delivered ultrasonic energy ceases. Verifying the optical code can include comparing identification information associated with the optically readable code to one or more databases of verified codes. The verified codes can be stored on the device. The instructions can further cause the processor to receive one or more signals from one or more sensors that provide feedback regarding quality and sufficiency of contact between the ultrasound device and the disposable component. The instructions can further cause the processor to receive one or more signals from one or more sensors that provide feedback regarding quality and sufficiency of contact between the disposable component and the subject's tissue. The instructions can further cause the processor to send one or more signals to one or more indicators of the device to inform the subject regarding quality and sufficiency of contact between the disposable component and the subject's tissue. A housing of the device can include a window through which the code reader assembly transmits and receives light. The window can be on a head portion of the ultrasound device, the head portion including a transducer head of the ultrasound transducer assembly. The window can be on a transducer face of the head portion, wherein the transducer face can be adapted to contact the support of the disposable component when the disposable component can be properly attached to the ultrasound device. The instructions can further include instructions to determine that the disposable component can be properly attached to the ultrasound device prior to delivering the ultrasonic energy to the subject. The determining can include verifying sufficient contact between the disposable component and the ultrasound device. The determining can include detecting attachment of the disposable component to the ultrasound device using one or more magnetoresistive sensors. The instruction can further include providing feedback to the subject indicating that the disposable component can be properly attached to the ultrasound device.

According to some aspects, a device for applying ultrasonic energy to a subject includes: a reusable component including an ultrasound transducer assembly and a code reader assembly adapted to detect an optically readable code; and a disposable component including the optically readable code, wherein the optically readable code can include encoded information related to ultrasound parameters for operating the ultrasound transducer assembly, wherein when the reusable component and the disposable component are attached together, the ultrasound transducer assembly and the disposable component are adapted to deliver ultrasound energy to the subject according to the ultrasound parameters. The ultrasound parameters can be adapted to deliver the ultrasound energy for imaging internal body structures of the subject. The ultrasound parameters can be adapted to deliver a therapeutic ultrasound energy to one or more tissues of the subject. The ultrasound parameters can be adapted to deliver the therapeutic ultrasound energy to the subject's genital tissue. The disposable component can include a coupling pad adapted to contact external genital tissue around the subject's vagina, the reusable component and the disposable component can be adapted to deliver the therapeutic ultrasound energy to increase blood flow to internal vaginal tissue to an increased level above a baseline level of blood flow to the internal vaginal tissue such that the increased level of blood flow to the internal vaginal tissue persists after energy application ceases. The ultrasound parameters can be in accordance with a prescribed therapeutic treatment. The reusable component can be adapted to deliver the prescribed therapeutic treatment once the optically readable code can be read by the code reader assembly. The disposable component can include a coupling pad, the coupling pad including a deformable coupling structure adapted to contact external genital tissue around the subject's vagina and geometric features configured to mate the coupling pad with the ultrasound transducer assembly, the disposable component can further include the optically readable code. The ultrasound parameters include one or more of therapy duration, lockout duration, ultrasound frequency, duty cycle and intensity of the ultrasound energy. The lockout duration can be a period of time after a treatment dose in which the device will not deliver another treatment dose. The lockout duration can range from about 4 to 24 hours. The intensity of the ultrasound energy can be associated with an electrical power delivered to the transducer. The optically readable code can include identification information associated with the disposable component, wherein the reusable component can be adapted to verify that the disposable component corresponds to pre-approved disposable component, that the disposable component is unused, or that the disposable component corresponds to pre-approved disposable component and that the disposable component is unused. Verifying can be based on the identification information of the optically readable code detected by the code reader assembly. The reusable component can be adapted to attach to a number of different disposable components having different optically readable code with different ultrasound parameters. The different ultrasound parameters can be associated with different prescribed therapeutic treatments.

According to some aspects, a method of applying ultrasonic energy to a subject includes: reading an optically readable code on a disposable component using an optical reader assembly of an ultrasound device, wherein the optically readable code includes encoded information related to ultrasound parameters for operating a ultrasound transducer assembly of the ultrasound device; and delivering ultrasound energy to the subject using the ultrasound device in accordance with the ultrasound parameters with the disposable component attached thereto. The method can further include detecting ultrasonic energy reflected off of tissue of the subject to create images of the tissue. The ultrasound parameters can be in accordance with a prescribed therapeutic treatment for treating the one or more tissues of the subject, and wherein delivering the ultrasound energy can include delivering the prescribed therapeutic treatment to the one or more tissues of the subject. The prescribed therapeutic treatment can be delivered to the subject's genital tissue. Delivering the prescribed therapeutic treatment can increase blood flow to internal vaginal tissue to an increased level above a baseline level of blood flow to the internal vaginal tissue such that the increased level of blood flow to the internal vaginal tissue persists after the applied ultrasonic energy ceases. The disposable component can include a coupling pad including a deformable coupling structure adapted to contact external genital tissue around the subject's vagina. The reusable component can include geometric features configured to mate the coupling pad with the ultrasound device. The ultrasound parameters can include one or more of ultrasound energy application duration, lockout duration, ultrasound frequency, duty cycle and intensity of the ultrasound energy. The optically readable code can be a first optically readable code on a first disposable component and can be associated with a first set of ultrasound parameters, the method can further include reading a second optically readable code on a second disposable component and associated with a second set of ultrasound parameters different than the first set of ultrasound parameters. The method can further include delivering ultrasound energy in accordance with the second set of ultrasound parameters with the second disposable component attached thereto. The second set of ultrasound parameters can include at least one different ultrasound parameter than the first set of ultrasound parameters. The least one different ultrasound parameter can include one or more of: a different lockout duration between applied treatments, a different treatment intensity, a different duty cycle and/or different duration.

According to some aspects, a device for applying ultrasonic energy to a subject includes: a computer readable medium having instructions stored therein that, when executed by a processor of the device, cause the processor to perform operations including: reading an optically readable code on a disposable component using an optical reader assembly of an ultrasound device, wherein the optically readable code can include encoded information related to ultrasound parameters for operating a ultrasound transducer assembly of the ultrasound device; and delivering ultrasound energy to the subject using the ultrasound device in accordance with the ultrasound parameters with the disposable component attached thereto. The ultrasound energy can be adapted for imaging internal body structures of the subject. The ultrasound energy can include a therapeutic dose of ultrasound energy delivered to one or more tissues of the subject. In some cases, the ultrasound energy is high intensity focused ultrasound (HIFU) to generate a focal area of high heat. HIFU may be used in treatments for cancer or aesthetic (e.g., skin tightening) applications. The ultrasound can include a therapeutic dose of ultrasound energy delivered to the subject's genital tissue. The delivered therapeutic dose of ultrasound energy can increase blood flow to internal vaginal tissue to an increased level above a baseline level of blood flow to the internal vaginal tissue such that the increased level of blood flow to the internal vaginal tissue persists after the delivered ultrasonic energy ceases. The instructions can further include instructions to determine that the disposable component can be properly attached to the ultrasound device prior to delivering the ultrasound energy to the subject. The instructions can further include instructions to verify that the disposable component meets required specifications, can be unused, or meets required specifications and can be unused. The instructions can further include adjusting one or more of ultrasound energy duration, lockout duration, ultrasound frequency, duty cycle and intensity of the ultrasound energy based on the read optically readable code. The instructions can further include instructions for determining that the disposable component corresponds to a pre-approved disposable component, that the disposable component is not used, or that the disposable component corresponds to a pre-approved disposable component and is not used. The instructions can further include instructions for verifying sufficient contact between the disposable component and the ultrasound device. The instructions can further include instructions for detecting attachment of the disposable component to the ultrasound device using one or more sensors. The instructions can further include instructions for providing feedback to the subject indicating that the disposable component can be properly attached to the ultrasound device. The device can further include an ultrasound transducer adapted to deliver the ultrasound energy, wherein the ultrasound transducer is adapted to penetrate tissue to a depth ranging from about 3 cm to about 5 cm before attenuation. The device can further include an ultrasound transducer adapted to deliver the ultrasound energy, wherein the ultrasound transducer is adapted to generate ultrasound waves having an intensity ranging from about 0.25 W/cm2 to about 5 W/cm2 and a frequency ranging from about 0.5 MHz to about 4 MHz. The device can further include an ultrasound transducer adapted to deliver the ultrasound energy, wherein the ultrasound transducer is adapted to generate high intensity focused ultrasound (HIFU) waves.

Although many of the examples described herein relate to devices and treatment for vaginal rejuvenation, the embodiments described herein are not necessarily limited to vaginal rejuvenation devices and methods. For example, the devices and methods may be adapted for providing ultrasound therapy to any of a number of tissues and/or organs. For example, the reusable component and the disposable component may be adapted to deliver energy for physical therapy (e.g., tendinitis, bursitis, muscle and/or bone healing) or resolving kidney stones. In some examples, the ultrasound energy is high intensity focused ultrasound (HIFU). In some applications, a HIFU is used to generate a focal area of high heat in treatments for cancer or cosmetic (e.g., skin tightening) applications. Alternatively or additionally, the devices and methods may be adapted for any of a number of ultrasound imaging applications. For example, the reusable component and the disposable component may be adapted to deliver energy for imaging internal body structures (e.g., for diagnostic imaging).

These and other aspects and advantages are described herein.

DETAILED DESCRIPTION

Figure 1B:
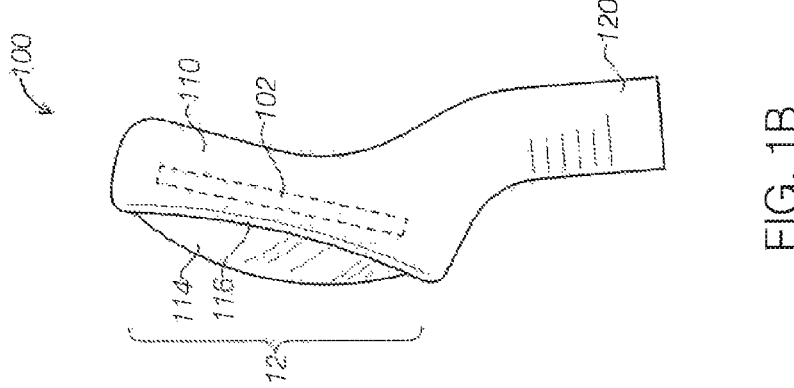
Figure 1A:
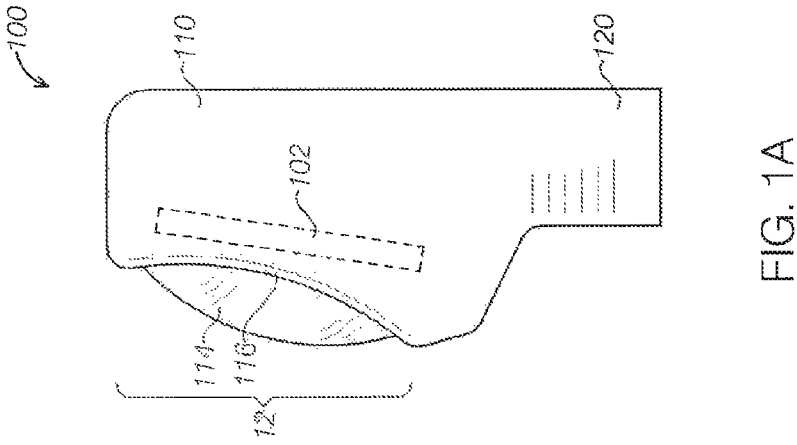

Described herein are ultrasonic devices and methods used in medical applications. In some cases, the ultrasonic devices includes features designed to promote rejuvenation of a women's vulvovaginal area. The term "vulvovaginal rejuvenation" used herein refers to improving the overall function of the vulvovaginal area that may have suffered from decrease in lubrication, loss of elasticity and resilience, and/or decreased blood flow. Thus, vulvovaginal rejuvenation can refer to any one or a combination of alleviating vaginal dryness, increasing vaginal lubrication, increasing elasticity and/or resilience, and increasing blood flow.
Handheld Ultrasound Devices In general, the devices described herein are handheld ultrasound devices that provide ultrasound energy. Ultrasound energy is a form of energy that is created by vibrating or moving particles within a medium, where the medium in needed to conduct and propagate its energy. Ultrasound energy is defined by vibrations with a frequency greater than 20 kHz. As shown in FIGS. 1A-1C, a handheld ultrasound device 100 includes a device body 110 having an energy delivery element 112 and a handle 120. The handheld ultrasound devices disclosed here also include an ultrasound energy source 102 providing ultrasound energy to the energy delivery element. The ultrasound energy source 102 is typically located within the device body 110, but it may alternatively be contained within the energy delivery element 112. In those latter instances, the device body 110 may have a thickness suitable for accommodating the ultrasound energy source 102 and/or circuitry, and the handle 120 may vary in length and circumference, based upon components and circuitry integrated into these elements. In other examples, the circuitry and necessary components may be separate from the handheld ultrasound device but able to electrically couple to the handheld ultrasound device using standard electrical connectors and cords.

The energy delivery element 112 may include an acoustic coupler 114 or coupling pad and an attachment mechanism 116. Because the acoustic coupler 114 is intended to contact a user's tissue, it is deformable enough to be able to conform readily to the user's anatomy while still having enough structure such that it is able to maintain its overall shape. The acoustic coupler 114 may have a general size and shape that conforms to the female vulvovaginal region (i.e., vulva, labia majora, labia minora, and introitus). The acoustic coupler 114 may be formed of one or more compartments or one or more regions of material or combination of materials. A more detailed discussion on the types of materials useful in forming the acoustic coupler 114 may be found in the sections below. The acoustic coupler 114 may be permanently or releasably attached to the attachment mechanism 116. The acoustic coupler 114 and the attachment mechanism 116 may be mated through any suitable means not limited to hooks and loops, snaps, clasps, magnets, glue, stitching and so forth. The attachment mechanism 116 may be formed of one or more than one layer of semi-rigid material (e.g., foam, rubber) configured to maintain contact with the acoustic coupler 114. The attachment mechanism 116 is also configured to provide acoustic contact with the ultrasound energy source 102 in the device body 110. An example of this is found in FIG. 3B, where the attachment mechanism includes couplers 118 to acoustically couple the energy delivery element 112 with the energy source (not shown) in device body 110. In this example, the device body 110 may also include slots (not shown) that aid with holding the entire energy delivery element 112. In other examples, the attachment mechanism 116 may attach and acoustically couple to the ultrasound energy source 102 through an arrangement including but not limited to a key and slot arrangement, a pin and hole arrangement and so forth.

Figures 2A, 2B, 2C:
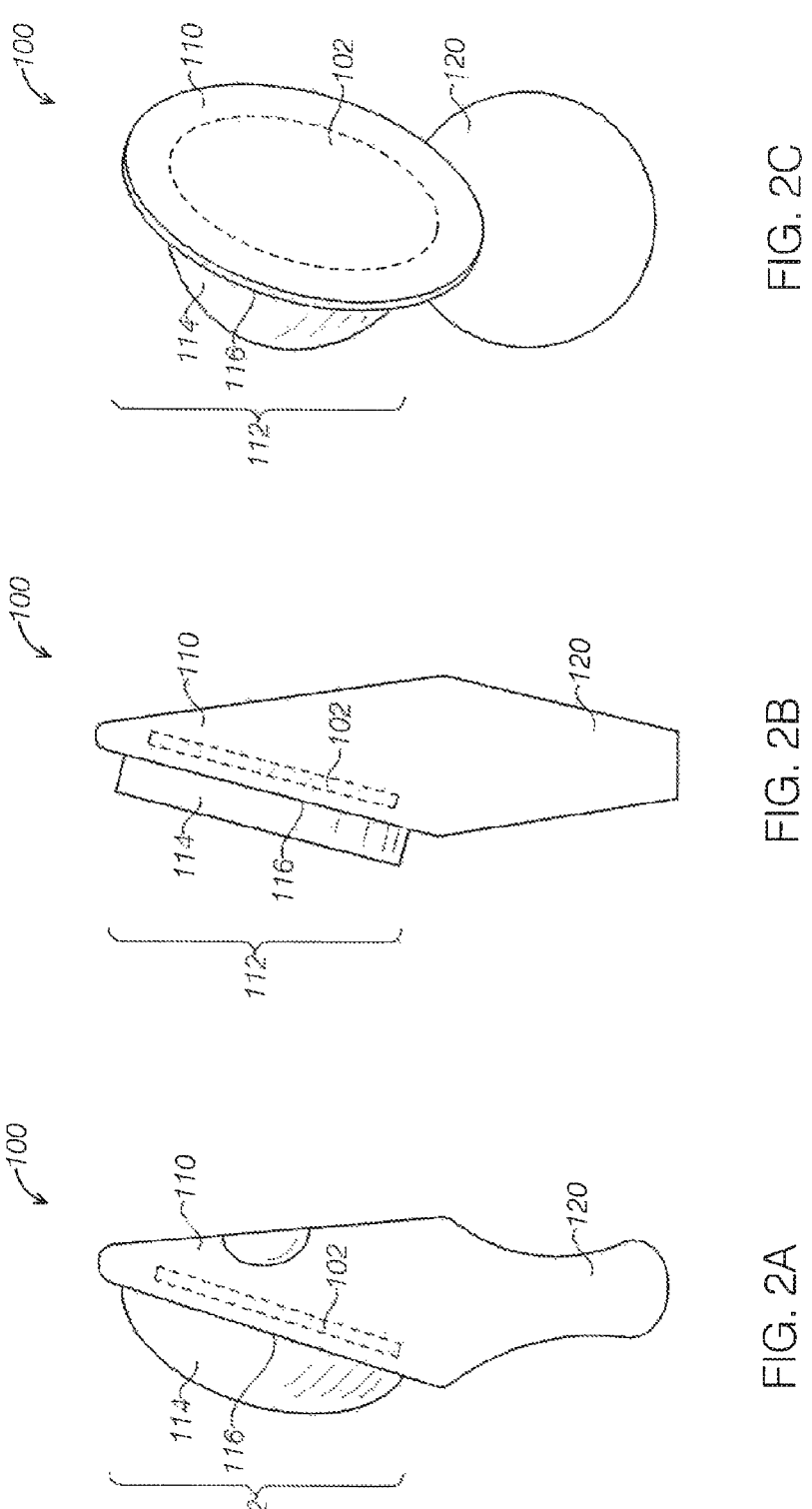
FIGS. 2A-2C show three different possible embodiments for the handheld ultrasound device.

Variations on the handheld ultrasound device are shown in FIGS. 2A-2C. The handheld ultrasound device shown in FIG. 2A includes an acoustic coupler 114 of the energy delivery element 112 that is convex in shape. In another variation, the acoustic coupler 114 of the energy delivery element 112 shown in FIG. 2B has largely uniform thickness throughout. In both of these variations, the acoustic coupler 114 of the energy delivery element 112 may be deformable such that when it is pressed against the user's external genitalia, it is able to more easily conform to the changing topography of the external genitalia tissue. In some variations, the acoustic coupler 114 may be shaped to conform to the general outer vaginal structure. FIG. 2C shows another variation of the handheld ultrasound device where the handle has a semispherical shape. In some other variations, no actual handle is present and the user would hold onto the device body 110 itself instead of holding onto a handle.

The ultrasound energy source 102 may be a piezoelectric ceramic or electromagnetic transducer and wave generator disposed within device 100 and in acoustic communication with the acoustic coupler 114 of energy delivery element 112. The ultrasound source may be constructed from piezoelectric materials such as lead zirconate titanate, potassium niobate, sodium tungstate, etc. The transducer assembly may consist of either one or an array of piezo-ceramic ultrasound transducers. The transducer assembly may also be Capacitive Micro-machined Ultrasound Transducers (CMUT) to appropriately apply diffuse ultrasound or provide constructive ultrasound wave interference and focus the ultrasound energy to the target tissue and appropriate vascular bed. The target of the ultrasound energy (unfocused or focused) may be further tuned to cover the mucosal layers of the vaginal canal. In some instances, the ultrasound transducer may have an effective radiating area between 0.1 cm² and 10 cm². In some instances, the effective radiating area may follow the general outline of the outer female genitalia. In some embodiments, the ultrasound may be preferentially focused on the introitus and/or vestibule only, the bottom third of the vagina, the bottom half of the vagina, or cover the entire vaginal canal.

The energy delivery element 112 of the handheld ultrasound delivery device 100 is configured to engage tissue around the subject's vagina as well as the outer genitalia. As mentioned earlier, the energy delivery element 112 may include an acoustic coupler 114 or coupling pad that aids with delivering ultrasound energy to the tissue. The acoustic coupler 114 may be in the form of a preformed gel (e.g., polyethylene glycol-based polymer hydrogel, agar, pectin, carrageenan, etc.), malleable solid or porous pad (e.g., silicone rubber, low durometer polymer, fabrics or flexible foams) or acoustic conducting gel (e.g., ultrasound gel) or fluid-filled bag or compartments, wherein the fluid is water (e.g., deionized, distilled), oil (e.g., mineral), gel, gelatin or other sonolucent and biocompatible fluid. The bag or compartments may be constructed of silicone rubber, low durometer polymer such as poly tetra fluoroethylene (PTFE), Nylon, Latex, low or high density polyethylene (LDPE, HDPE), nitrile, polyisoprene, polyurethane, or urethane; a fabric or a natural (organic) material such as animal skin, agar, pectin of carrageenan. In some instances, acoustic coupler 114 may be biocompatible, non-allergenic, bacteriostatic, and/or antimicrobial. In general, the bag or compartment walls of the acoustic coupler 114 are approximately 0.001 mm to approximately 10 mm in thickness.

The acoustic medium within the acoustic coupler 114 or coupling pad is able to transmit, with minimal loss of acoustic power, ultrasonic energy from the surface of the ultrasonic energy transducer to the target tissue of one or more of the vaginal vestibule, vaginal canal, introitus, vulva, labia minora, labia majora, clitoris, or surrounding area to the genitalia (e.g., perineum, rectum, etc.). The acoustic coupler 114 may also function to collimate and/or focus ultrasonic energy from the ultrasonic energy transducer surface to specific targeted regions within the vaginal canal, introitus, vulva, and/or external genitalia regions. The malleability of the acoustic coupler 114 allows it to fill the spaces of air between the transducer and user's variably shaped genital tissues, but it does not extend beyond the introitus and hence does not penetrate the vaginal canal. In some embodiments, it may penetrate the vaginal canal. The acoustic coupler 114 may act as a safety feature by preventing the occurrence of hot spots from converging waves of incident and reflected ultrasound energy (i.e., standing waves), which may otherwise occur at the interface between the surface of the ultrasound transducer and the genital tissue. It may also prevent surface heating and pain due to inadequate coupling (acoustic impedance mismatch) between the device and the user's tissue. The acoustic coupler 114 may also control the feedback to an open- or closed-loop treatment and/or safety algorithm.

The acoustic coupler 114 or coupling pad may be covered with acoustic coupling gel where it interfaces with the person's tissue, which will most often be the vulva and/or introitus. The gel layer may be pre-applied to the acoustic coupler 114 at the time of manufacture and require the removal of a covering strip or protective, containing layer upon use. The gel layer may also be applied by the user at time of use.

The acoustic coupler 114 or coupling pad may be convex in its profile and elliptical, ovoid or otherwise shaped for roughly conforming to the shape of the vulva and introitus of the vagina (FIGS. 1A, 1B, 2A, 2B, and 2C). The shaped contours of the acoustic coupler 114 may also function to focus the ultrasonic energy to the target areas within the vaginal canal, vascular bed, or more superficially to the external genitalia. The shaped contours of the acoustic coupler 114 may also function to provide tactile or contact feedback to the user so that the user knows the device is being held in the correct location and position. The acoustic coupler 114 may be between 1 mm and 50 mm in thickness or 1-5 mm, 1-10 mm, 1-20 mm, 25-50 mm, between 10 mm and 200 mm in length, 10-20 mm, 15-50 mm, 50-75 mm, 75-150 mm, 100-150 mm, 150-200 mm and between 10 mm and 50 mm in width, 10-20 mm, 20-40 mm, or 25-50 mm. In some variations, the acoustic coupler 114 may be approximately 10 mm to approximately 200 mm in length and approximately 10 mm to approximately 50 mm in width. The acoustic coupler 114 may be one size, have multiple size options or may be custom fit to each user. The orientation of the acoustic coupler 114 relative to the target tissue areas may also be adjusted by the user based on her anatomy, with feedback from the system.

Figure 3A:
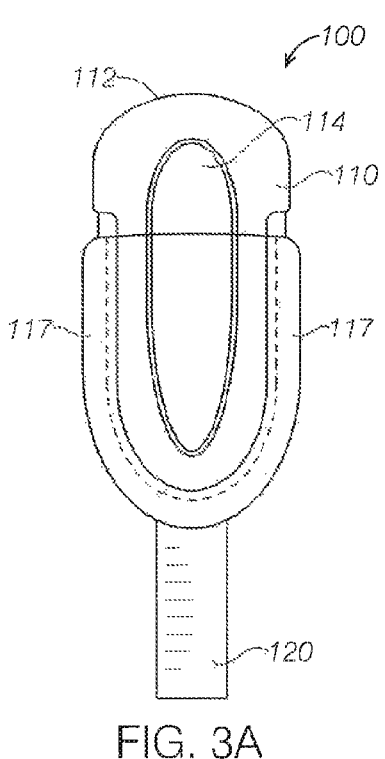
FIGS. 3A-3D show variations of acoustic coupler.
Figure 3B:
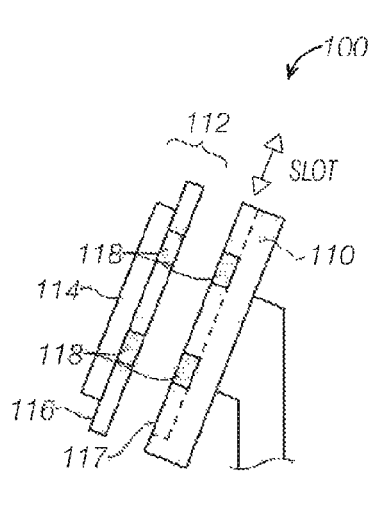
Figure 3C:
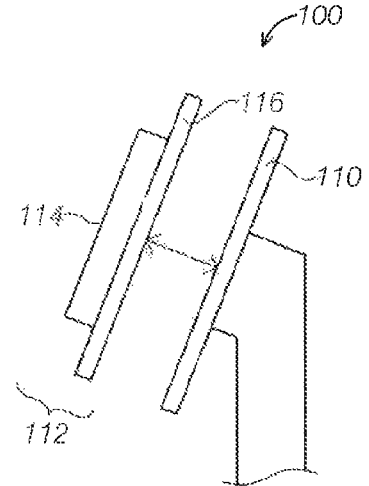
Figure 3D:
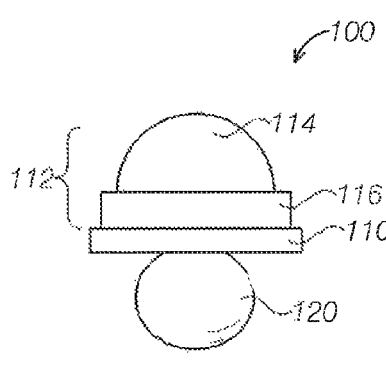

The acoustic coupler 114 may be reusable and capable of being disinfected after use. Alternatively, the acoustic coupler 114 or coupling pad may be disposable and discarded after each individual use or several uses of the device. FIGS. 3A and 3B show one example of how the energy delivery element 112 (and its acoustic coupler 114) may be detachably connected to the device body 110. In this example, the device body 110 includes side slots 117 into which the sides of the attachment mechanism 116 may slide into and couple to the device body 110.

Figures 4A, 4B:
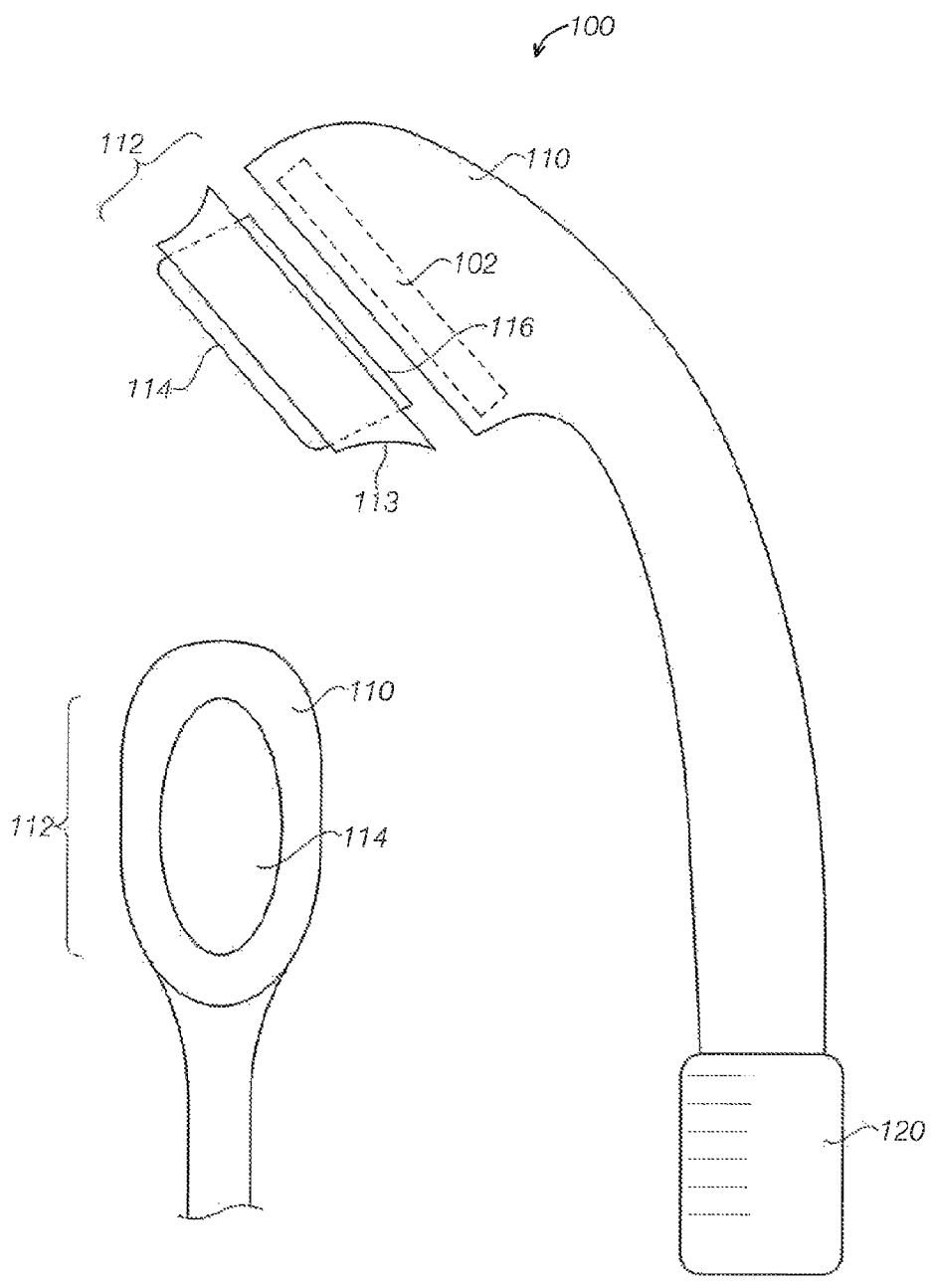
FIGS. 4A and 4B show a side and front view of yet another example of a handheld ultrasound device.

FIGS. 4A and 4B show another variation of the energy delivery element 112 where a rim 113 further aids with maintaining coupling of the energy delivery element 112 with the device body 110. The rim 113 may connect to the device body 110 via corresponding threads, snaps, adhesives, clasps, magnets, buttons, and so forth.

In the case where only the acoustic coupler 114 portion of the energy delivery element 112 may be disposable, the energy delivery element 112 may be attached to the device body 110 in a multitude of ways. The coupling mechanism may include, but is not limited, to an open slot feature whereby the acoustic coupler 114 may slide into place (e.g., as shown in FIGS. 26E-26I), a hinged or movable clasping feature that secures the acoustic coupler 114 into place, an adhesive area on which the acoustic coupler 114 may be affixed, an internally threaded feature into which the acoustic coupler 114 may be threaded down into contact with the attachment mechanism 116, or some geometric feature on the distal end of the handle that secures the acoustic coupler 114 to the surface of the attachment mechanism 116. In some instances, the acoustic coupler 114 may be permanently attached to an attachment mechanism 116 which then may mate with the device body 110 through corresponding magnets arranged about the energy delivery element and the device body 110. Additionally, the acoustic coupler 114 may be connected to the attachment mechanism 116 via elastic or Velcro® straps, by features on the reusable portion of the device that penetrate into the coupling feature medium (e.g., pins, barbs or hooks), or by vacuum or suction attachment.

The relative orientation of the ultrasound energy source 102 and the energy delivery element 112 may be achieved using couplers 118 that mate between the ultrasound energy source 102 and the attachment mechanism 116 (see FIG. 3B). More focused ultrasound output may be achieved through arranging the ultrasound energy source 102 in a particular orientation or through automatic adjustments to the ultrasound energy source 102 based on closed-loop feedback during use.

As mentioned above, the device has features that provide feedback to the user to inform whether or not contact between the transducer face and the coupling pad or the contact between the coupling pad and the user's tissue is non-optimal (for safety to the user, for the integrity of the device, and for efficacy of treatment). These feedback mechanisms include simple feature locks that may provide "snap" sounds to inform the user the part is seated; pressure, impedance or other sensors between the transducer and the coupling pad that provide direct feedback to the user; or alarms (e.g., vibrating alarm) on the ultrasound generator that are based on sensor feedback. Such feedback can reflect inadequate coupling between the transducer and the acoustic coupler 114, or inadequate coupling between the acoustic coupler 114 and the user's tissue. The device may have a closed-loop algorithm to automatically shut off ultrasound delivery if inadequate coupling has been detected for a period of time.

The feedback may be based on reflected ultrasound energy, ultrasound electronics voltage, current or phase or on some other parameter, such as tissue temperature measured by a temperature sensor or electrical power delivered to the transducer. The contact feedback information can be displayed to assist in adjustment of the acoustic coupler 114 to the user's tissue or the attachment mechanism 116 to the device body 110. This display may include blinking lights of different colors similar to a tuning instrument, audible cues, mechanical/vibratory cues, and so forth. The surface-to-surface contact between the transducer face and the acoustic coupler 114, and/or the interface between the acoustic coupler 114 and the user's anatomy may be adjusted just before and/or during ultrasound treatment administration to maintain good acoustic coupling between the surfaces. This adjustment can be achieved by spring-loaded features, magnetic or mechanical snap fits, elastic materials (e.g., silicone or elastic bands) that wrap around the back of the transducer, adhesives, or visual, audio, or other types of cues to alert the user to move the device slightly and/or apply more force herself.

In some instances, the handheld ultrasound device may have several sensors embedded within the acoustic coupler 114 that allows for measurement of various physiologic parameters. Physiological parameters may include mucosal/dermal blood flow, possibly measured with Doppler ultrasound, Doppler laser imaging, temperature measurement (thermometer), infrared imaging, thermography, or photoplethysmography. Parameters may include vaginal lubrication measured for example utilizing humidity sensors, absorbent materials, or other methods for detecting lubrication and/or secretion. Parameters may include tissue temperature, measured for example utilizing thermometers or thermocouples, or other methods for detecting temperature changes. Additional physiologic parameters relating to vulvovaginal health and sexual function may also be measured utilizing the appropriate sensor setup. Parameters may include tissue impedance and other various markers of vulvovaginal tissue health such as: tissue elasticity, type and amount of vulvovaginal fluid present, vulvovaginal pH, friability of vulvovaginal mucosa, amount of vaginal moisture present, degree of inflammation present, and percentage of parabasal, intermediate, and/or superficial squamous cell types present in the vulvovaginal epithelium. Parameters may also include cellular calcium uptake, cellular activity and metabolism, protein synthesis by fibroblasts, collagen synthesis and deposition, cell proliferation, cell degranulation, synthesis of non-collagenous protein (NCP), production and signaling of Vascular Endothelial Growth Factor (VEGF), formation of endothelial cells, release of endothelial growth factors, angiogenesis, release of angiogenesis-related chemokines or cytokines (e.g., Interleukin 8, IL-8, or basic Fibroblast Growth Factor, bFGF, or TNF-alpha). The parameters measured may also include biomarkers of negative side effects of ultrasound treatment, such as markers of inflammation and histamine production.

Figure 7:
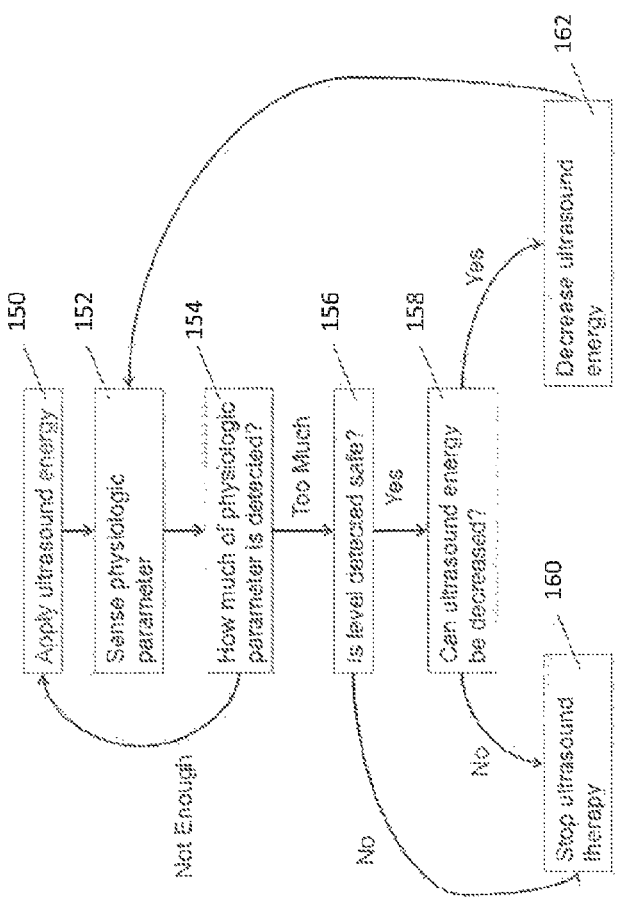
FIG. 7 is a diagram showing a closed loop therapy algorithm.

The sensors embedded within the device may allow for closed-loop feedback control of ultrasound application, as shown by the flow chart shown in FIG. 7. In general, the feedback control will be able to sense a physiological parameter 152 after ultrasound energy is applied 150. Once the physiological parameter is detected 154, the algorithm will query whether the detected physiological parameter level is safe 156. If the detected physiological parameter level is not safe, then the ultrasound therapy stops 160. If the ultrasound level is at an unsafe level, the algorithm will also determine if the ultrasound energy may be decreased 158. If the ultrasound energy cannot be decreased, the algorithm will halt the ultrasound therapy 160. If a decrease in ultrasound energy is possible 162, the device 100 controls will decrease the ultrasound energy output. At a later time during the ultrasound therapy, the algorithm will again sense the physiological control to determine if the ultrasound energy output is at a safe level. On the other hand, if the physiological parameter detected is too low or below a threshold value, the controls may send signals to the transducer to increase ultrasound energy output.

In one example, vulvar tissue temperature may be measured by a sensor in the coupling pad. If the temperature rises to a level that could potentially cause damage to the user, the feedback loop automatically adjusts the energy delivery parameters or turns off the energy delivery altogether. In another example, the device increases energy delivery if the temperature of the user's vaginal or external genitalia tissue is not high enough. In another example, the device measures physiologic outcome parameters (e.g., vaginal blood flow and/or lubrication) and automatically increases or decreases ultrasound delivery to achieve the desired outcome (e.g., more or less vaginal blood flow and/or lubrication). In another example, the device may monitor for adverse treatment effects and automatically titrates the ultrasound energy delivery to minimize side effects while still achieving the desired treatment outcome.

In general, the handle 120 allows the user to comfortably position and maintain the ultrasound device against her vaginal or external genitalia tissue. In some variations, the handle 120 of the handheld ultrasound device may also include a variety of components. In some instances, the handle 120 may include an ultrasonic waveform generator, an ultrasound transducer, accompanying electronics, or any combination of these elements inside. Alternatively, the handle 120 may merely support the structure that generates and delivers ultrasound treatment, but lacks any other parts required for ultrasound generation and ultrasound treatment administration. In the latter case, the handle would physically connect to the ultrasound transducer, and also be connected via a cord or wirelessly to another device that houses the electronics needed to supply the power and generate the ultrasound energy through the ultrasound transducer. In yet other examples, the handle may include a display for showing various parameters such as session time, adequate/inadequate contact, and so forth.

Figure 8A:
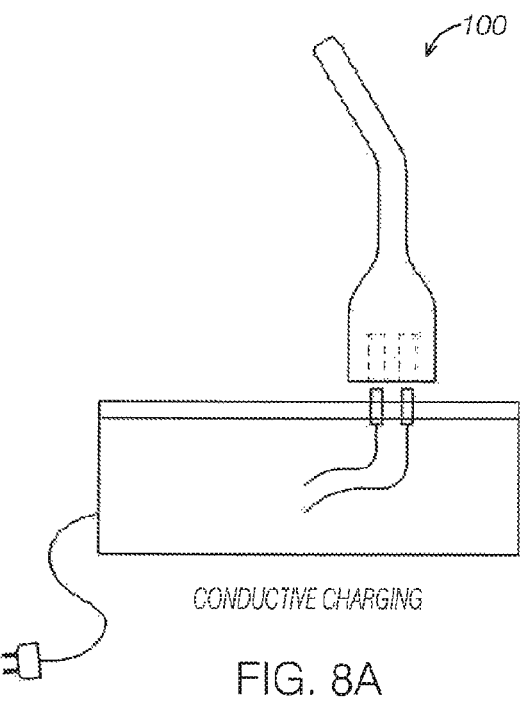
FIGS. 8A and 8B are illustrations of two embodiments of a charging station for the handheld embodiment of the device.
Figure 8B:
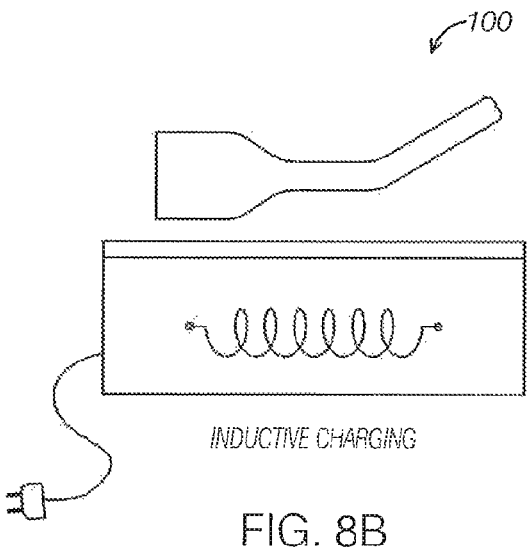

The handheld ultrasound device may also include a power source that is rechargeable and can be recharged with an external recharging station, or that is disposable and consists of replaceable lithium-ion or other sources of direct current (i.e., batteries). The device may also be powered by alternating current from an external source (e.g., an electrical outlet). Where the device is rechargeable, the recharging station may physically couple to the ultrasound handle. A portable recharging component may be coupled to the handle through corresponding geometric features on the handle and the recharging component. (FIG. 8A). The recharging station may be electronically coupled to the rechargeable device via conductive recharging pins in the handheld and corresponding pins in the recharging station, or by proximity via inductance between the device and recharging station (FIG. 8B). The rechargeable transducer handle ultrasound device may hold a charge allowing for one or more treatments before requiring recharging. As alluded to earlier, the rechargeable transducer or ultrasound device may also include feedback for alerting the user as to when the treatment duration is finished and/or when there is too high a temperature at the ultrasound transducer surface (for safety) including but not limited to visual indicators (light emitting diodes or electric lamps), vibratory motors which pulse for a short duration of time or auditory or vibratory signals. Additional signals may also be provided to notify the user that the handheld ultrasound device requires recharging.

Figure 5:
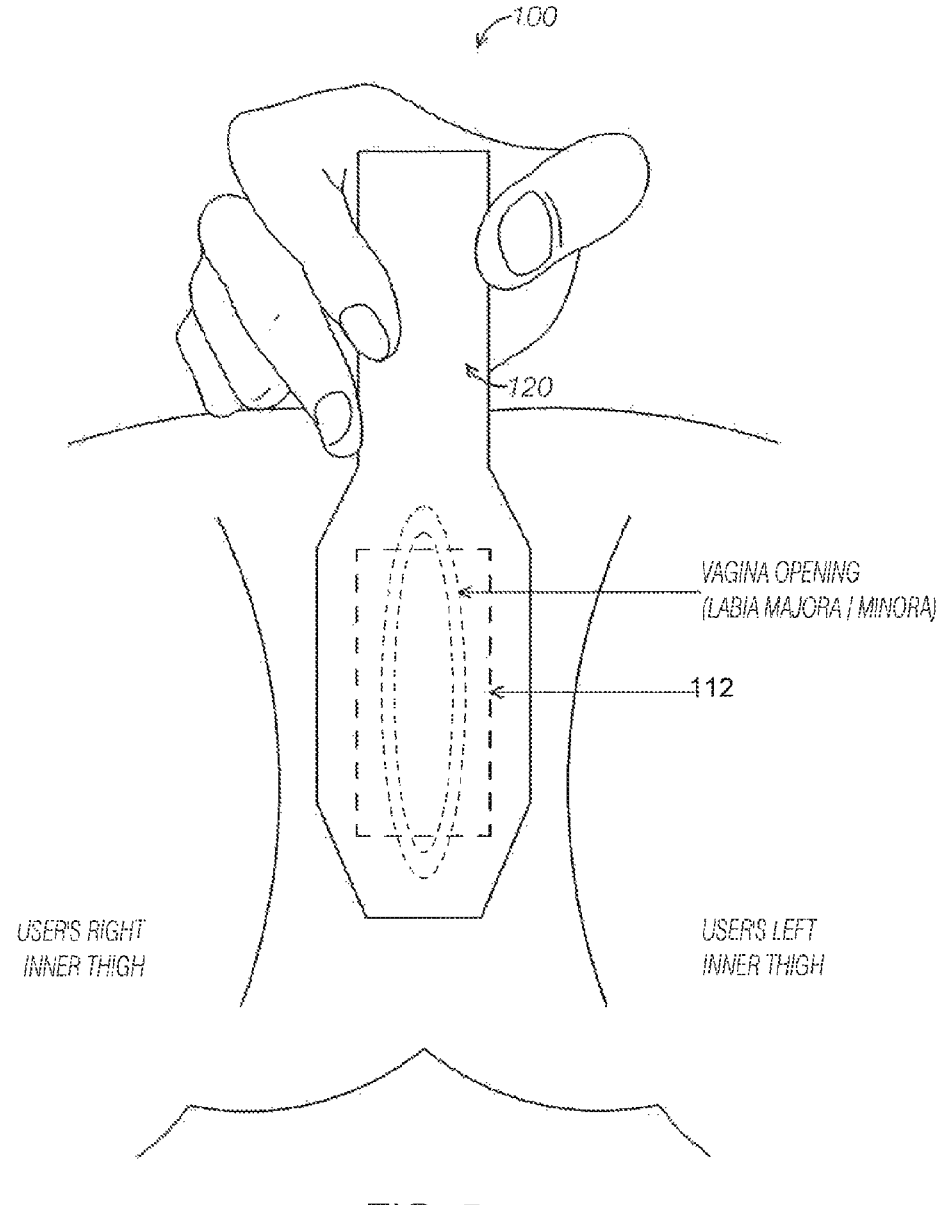
FIG. 5 is an illustration of placement location and orientation of a handheld embodiment.
Figure 6:
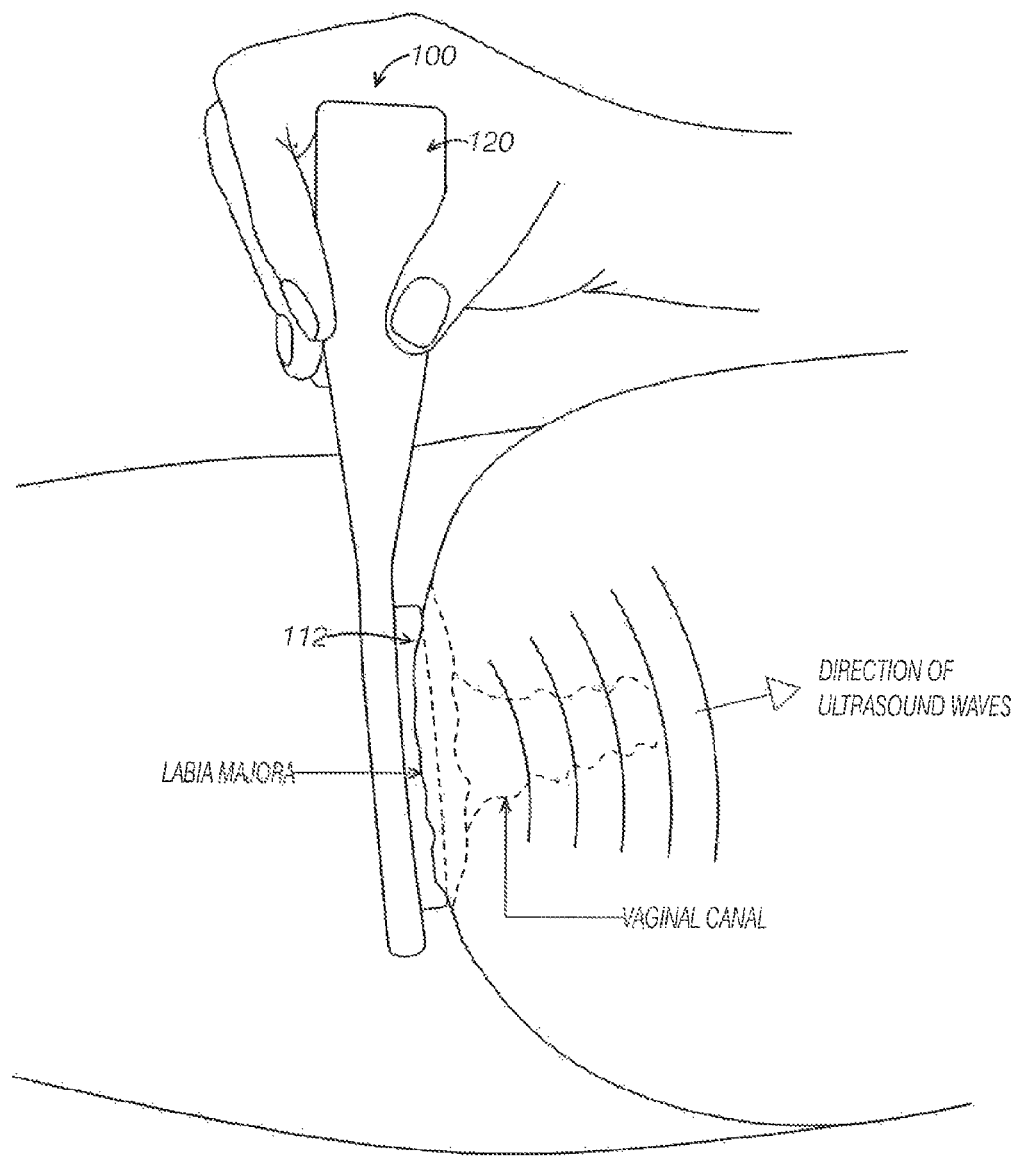
FIG. 6 is an illustration of placement location and orientation of a handheld embodiment including direction of ultrasonic wave propagation in relation to the vaginal canal (side view).

The device body 110 of the handheld ultrasound device may be any suitable size and shape. In some instances, the device body 110 may be elliptical in shape (FIGS. 1C, 3A, and 4B). In other examples, the handheld ultrasound device may have a more elongated shape such that the user may grip the handle (FIGS. 5 and 6). In some examples, the handheld ultrasound device may not include a handle, and where the device rests in the palm of the user's hand. In other examples, the ultrasound device may attach to (as opposed to being held by) the user's hand such as in a glove-based device that may be worn by the user, and where the ultrasound components are encompassed within the glove (e.g., palm portion). In yet other examples, the ultrasound device may be a ring-type design that may be worn on one or multiple fingers.

In general, the handheld ultrasound device may be used at home or in a clinical setting. If used at home, the user may be able to apply the ultrasound treatment herself. The device may be designed in such a way to be conducive to one-hand self-application (FIG. 5). Alternatively, the device and ultrasound treatment may be administered by a partner. In other embodiments, the device may be entirely hands-free, while still maintaining proper tissue contact, orientation, and treatment efficacy. If used in a clinic setting, the device and ultrasound treatment may be administered by a trained professional. Or in some instances, the user may be able to treat oneself after being trained by a professional.

Figure 10A:
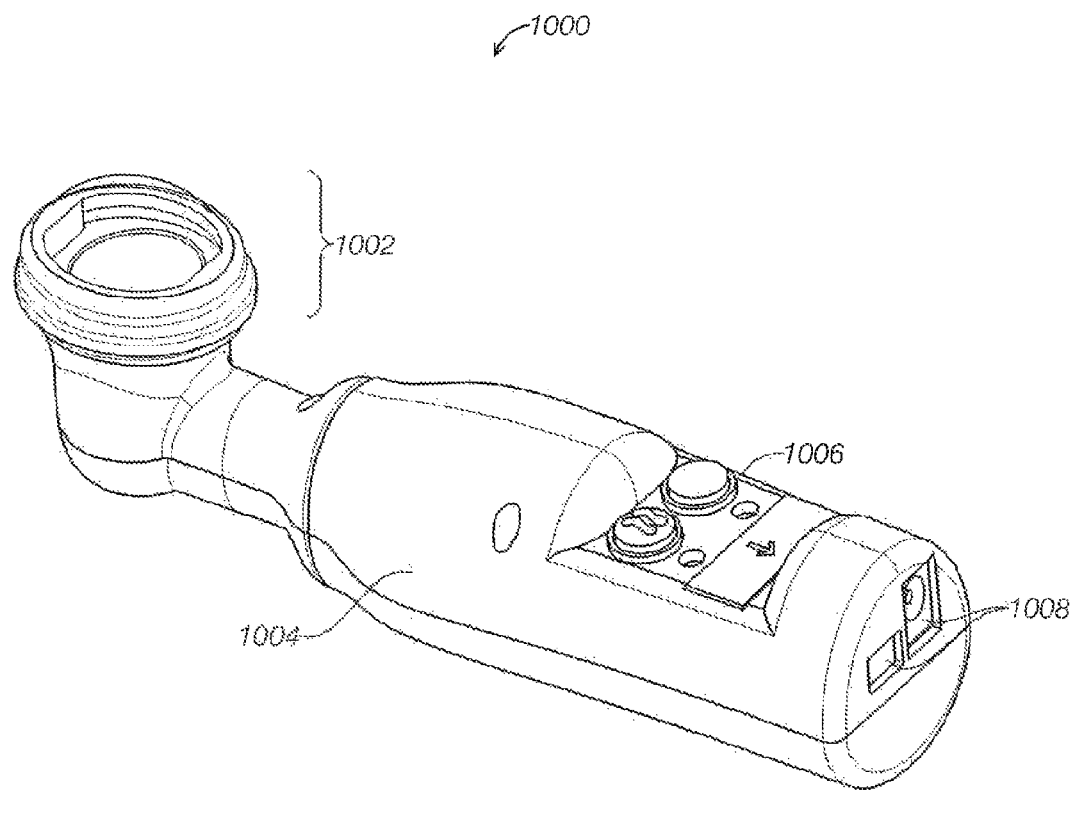
FIGS. 10A and 10B show another example of a handheld ultrasound device.
Figure 10B:
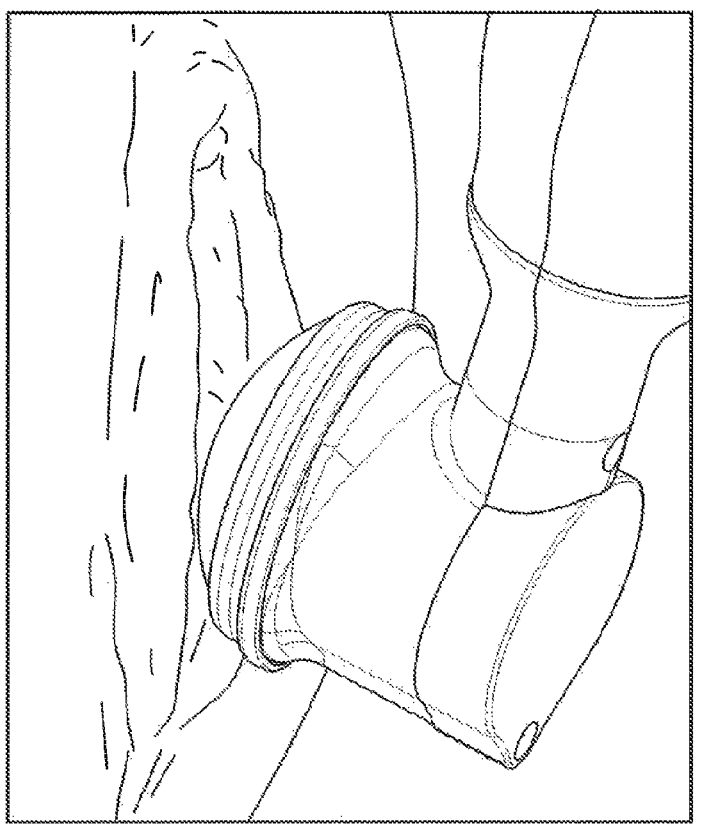

FIG. 10A shows another example of the handheld ultrasound device 1000 previously shown and described. As can be seen, this handheld ultrasound device includes a disposable coupling pad 1002 configured to couple to a woman's vulvovaginal region and an ultrasound device 1004 configured to deliver energy to the coupling pad 1002. The handheld device includes electronic components for generating the ultrasound energy to be delivered through the coupling pad. In this example of the handheld ultrasound device, the controls 1006 for the handheld device are located on a lower surface of the device. In other examples, the controls may be on an alternative surface of the handheld device (e.g., along a side surface or on a top surface). In yet other examples, the controls may not all be located on one surface of the device, but instead, may be disposed on multiple surfaces of the handheld device. The handheld device shown in FIG. 10A and in the prior figures may also include connection ports 1008 for recharging the device as well as ports for transferring data from the handheld ultrasound device to other communication devices (e.g., laptop, desktop, smart phone, tablets). In some instances, there may be applications for a smart phone or tablet associated with using and controlling the handheld ultrasound device. FIG. 10B shows the device of FIG. 10A during use, placed at the introitus, between the labia.

Methods and Parameters for Using the Handheld Ultrasound Devices

The methods for using the handheld ultrasound devices described herein may be used to improve vulvovaginal and vulvar tissue health. A device may be used on an as-needed basis, for example, prior to sexual intercourse to increase blood-flow and induce lubrication. The overall health of the vaginal and vulvar tissue may be improved by use of the device multiple (more than one), times a day, daily, weekly, multiple (two, three, four, five, or more than five) times a week, or monthly as a periodic treatment. The actual length of time for each session may be on the order of seconds to tens of minutes. In practice, the ultrasound sessions may be a few minutes to ten minutes. During such sessions, increases in blood flow to vulvovaginal tissue and vulvovaginal lubrication may be measurable. In some aspects, the device may be used a single time prior to a sexual encounter. In other aspects, the device may be used repeatedly unrelated to sexual activity. In both regimens, periodic use may revitalize vulvovaginal lubrication and/or tissue and improve vulvovaginal health.

In other instances, methods for using the handheld ultrasound devices may be used as a preventative measure. The output from the handheld ultrasound device may improve mucosal vascularity, restore tissue elasticity, promote angiogenesis, encourage collagen growth/regrowth, improve muscle tone, promote the repair of soft tissue, and/or to increase constitutive lubrication.

The devices and methods described herein for rejuvenating the user's vulvovaginal area and external genitalia may be used in the privacy of her own home although application of the ultrasound therapy may also be performed in a medical office setting.

In general, the handheld ultrasound devices described herein may be placed external to the vagina and locally apply ultrasound energy to all or a portion of the vaginal vestibule, vaginal canal, introitus, vulva, labia minora, labia majora, clitoris, or surrounding area to the genitalia (e.g., perineum, rectum, etc.) as shown in FIGS. 5 and 6. The device may also sit adjacent to the external genitalia, such as in the region of the mons pubis or proximal thighs. The handheld ultrasound device may cover some of the vulva or the clitoris, much like a feminine hygiene pad, but is completely non-penetrating of the vaginal canal. In some embodiments, the device may enter a small portion of the vaginal canal, while also residing outside the vaginal canal. Optionally, the device may be completely encased within the vaginal canal.

In general, the devices described herein are configured to provide ultrasound energy. While typically ultrasound energy may range anywhere between 20 kHz and 20 MHz, the ultrasound energy delivered from the handheld ultrasound device is approximately between 80 kHz and 3 MHz. At the range of 1 MHz and 3 MHz, optimal energy deposition occurs at more shallow tissue depths. In some instances, the user may vary the handheld ultrasound device's output for optimal energy deposition at more shallow tissue depths. The device may include features that provide for optimal energy deposition to all or a portion of the vaginal vestibule, vaginal canal, introitus, vulva, labia minora, labia majora, clitoris, or surrounding area to the genitalia (e.g., perineum, rectum, etc.).

In some instances, the ultrasound energy may be delivered at an intensity range of 0.1 $W/cm^2$ to 5.0 $W/cm^2$. More practically, the handheld ultrasound device is adapted to provide ultrasound intensity between approximately 0.25 $W/cm^2$ to approximately 3.0 $W/cm^2$. The intensity of the ultrasound energy is the acoustic ultrasound power over the area of the transducer.

The ultrasound output from the handheld devices may increase the temperature of the tissue being treated. In some instances, the ultrasound output may be designed to heat tissue to a minimum of 37° C., but no greater than 44° C., so as not to cause damage to the target or surrounding tissue. The increase in temperature from 37° C. to its upper limit may be increased stepwise or ramped up in a continuous fashion. Where the duty cycle of the ultrasound output is less than 100%, the increase in temperature may be coordinated with when the ultrasound beam is on or off. In other instances, the ultrasound output may be designed not to heat the tissue at all above the average core body temperature of 37° C. in order to induce only non-thermal effects in the tissue from ultrasound.

In some instances, the handheld ultrasound device may include an automatic duty cycle adjustment feature. The automatic duty cycle feature may be an open-loop (requiring action by the user) or closed-loop (not requiring action by the user) treatment algorithm. An automatic duty cycle adjustment feature is useful to ensure appropriate overall energy delivery to the tissue while maintaining user safety thereby providing optimal treatment for desired outcome. In some examples, the device may be highly customizable by the user to modify the treatment (e.g., delivery method, duration, and quantity of ultrasonic energy delivered to the vulvovaginal or surrounding tissue).

The handheld ultrasound device may have a duty cycle of anywhere between 10% and 100%. The term duty cycle refers to the percentage of time that a pulsed ultrasound wave is on (e.g., a 50% duty cycle means that a pulsed wave is on 50% of the time). At a duty cycle of 100% (also called a continuous duty cycle), the pulsed wave is on 100% of the time. The intensity and duty cycle can either be individually set for each treatment or set once for all subsequent treatments. In some embodiments, the intensity and duty cycle can be set by a trained physician, the user, or an advocate for the user. The intensity and duty cycle may be automatically set as a feature pre-programmed into the device and may or may not change. In some embodiments, the intensity and duty cycle settings are changed based on previous treatment duration and results. In some cases, the ultrasound parameters (e.g., intensity and duty cycle) can be stored in a code (e.g., optical code) on the disposable component and that can be read by the ultrasound device to inform the ultrasound device operating parameters. This can allow a single ultrasound device to provide multiple therapeutic regimens depending on the disposable component that is used. For example, the disposable component may be specified by the patient or prescribed by a healthcare professional. Detailed aspects regarding readable codes are described with reference to FIGS. 56A-56D and 57.

The methods disclosed herein for using the handheld ultrasound devices may improve one or more indicators of vulvovaginal tissue health including: elasticity, type and amount of vaginal fluid present at rest (unaroused state), type and amount of vaginal fluid present during arousal, vaginal pH, friability of vaginal mucosa, amount of vaginal moisture present, and degree of inflammation. In some instances, the amount of vaginal fluid may also be measured during an aroused state. These parameters may be measured by the Vaginal Health Index (VHI) (e.g., by trained observer, by computer imaging). The device may also improve the distribution of cell types present in the vaginal epithelium, as measured by the Vaginal Maturation Index (VMI) and reflective of the maturity and health of the vaginal epithelium. The cell types measured in this index are parabasal, intermediate, and superficial squamous cells. The methods and devices may improve the distribution of each of these types of epithelial cells towards a healthier tissue state.

More specifically, the methods associated with the handheld ultrasound devices may result in one or more of the following effects on vulvovaginal tissue: increase cellular calcium uptake, increase cellular activity, increase cell metabolism, increase protein synthesis by fibroblasts, promote collagen synthesis and deposition, promote cell proliferation, promote cell degranulation, increase synthesis of non-collagenous protein (NCP), increase production and signaling of Vascular Endothelial Growth Factor (VEGF), stimulate the formation of endothelial cells, stimulate the release of endothelial growth factors, promote angiogenesis, increase in angiogenesis-related chemokines or cytokines (e.g., Interleukin 8, IL-8, or basic Fibroblast Growth Factor, bFGF, or TNF-alpha).

Example 1

Figure 9:
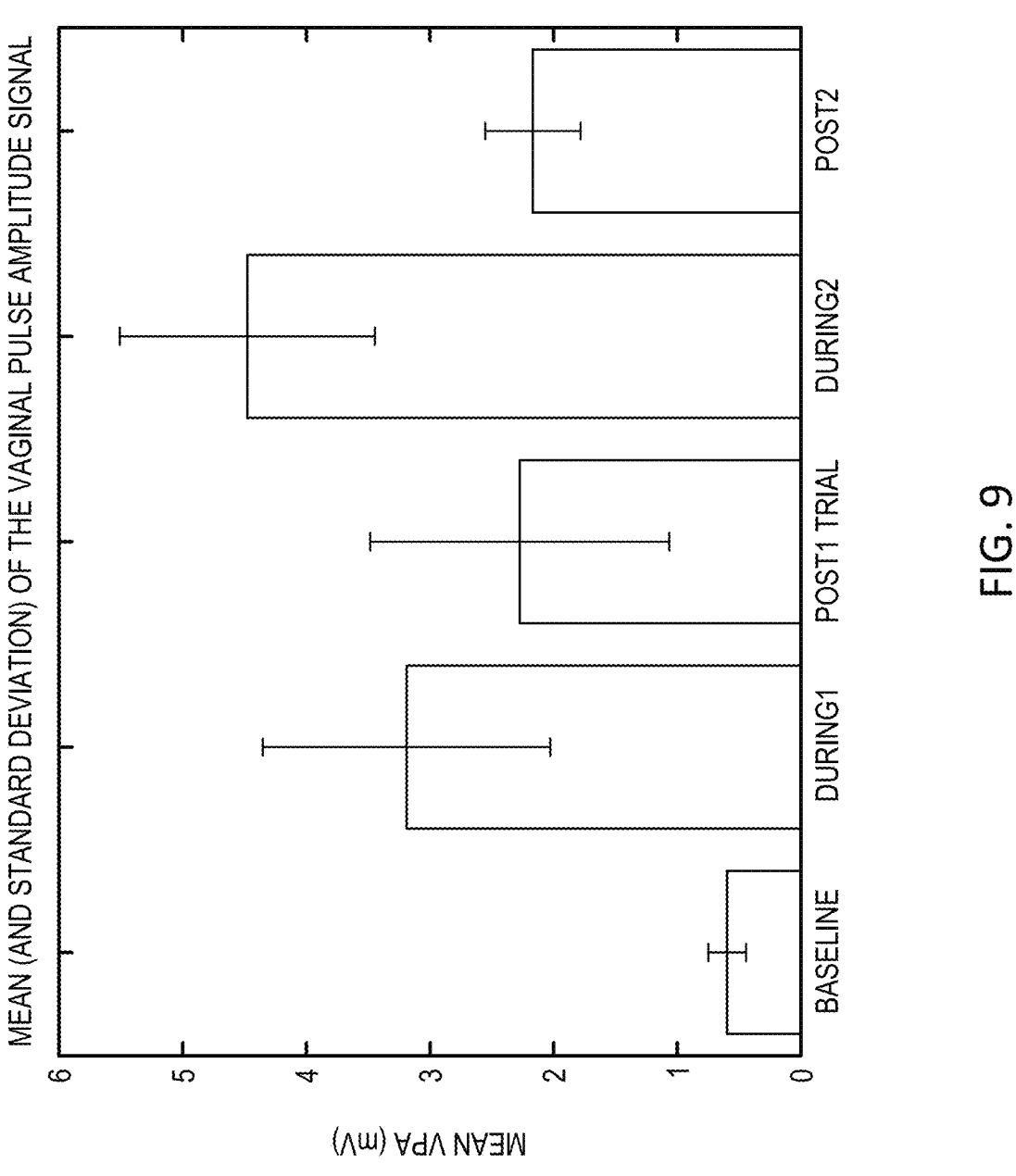
FIG. 9 is a bar graph showing clinical trial data showing an increase in the vaginal blood flow after treatments via the method and device described, herein.

A study was conducted with 9 subjects to evaluate the ultrasound devices and methods. The results indicate that there is a local increase in blood flow and temperature, as described in PCT Publication No. WO2015/116512, expressly incorporated by reference herein. FIG. 9 shows, for nine patients, the average increase in vaginal blood-flow during and after two subsequent treatments with an embodiment of the device and method described herein.

Coupling Component

As described herein, the acoustic coupler or coupling pad is a sonolucent, deformable pad (e.g., gel pad) that physiologically conforms to the introitus (vaginal opening) and surrounding structures while gently ensuring consistent, safe therapy delivery. In order to ensure safe and effective energy delivery to the appropriate anatomical target, the coupling pad has several performance goals. First, it should ensure solid contact between the ultrasound device and the user's tissue to encourage loss-free ultrasound energy transmission. Second, to achieve intimate, consistent contact with a variety of anatomies, the coupling pad should be deformable. Finally, to maintain safety, the coupling pad can prevent burns by serving as a buffer between the ultrasound transducer and the user's skin.

In some embodiments, the coupling pad comprises a combination of one or more of agarose, glycerin, water and cetylpyridinium chloride (CPC). Other materials are also possible (e.g., silicone rubber, elastomeric polyurethane, hydrogels, elastomeric acrylates). Agarose can advantageously provide good conformal and lubricious properties while still maintaining ultrasound intensity. Glycerin can advantageously provide lubricity to the coupling pad. The glycerin can migrate to the surface, creating a comfortable, lubricated surface for tissue coupling. CPC can advantageously provide antimicrobial properties to the coupling pad, reducing or eliminating the need for sterile packaging.

Figure 11:
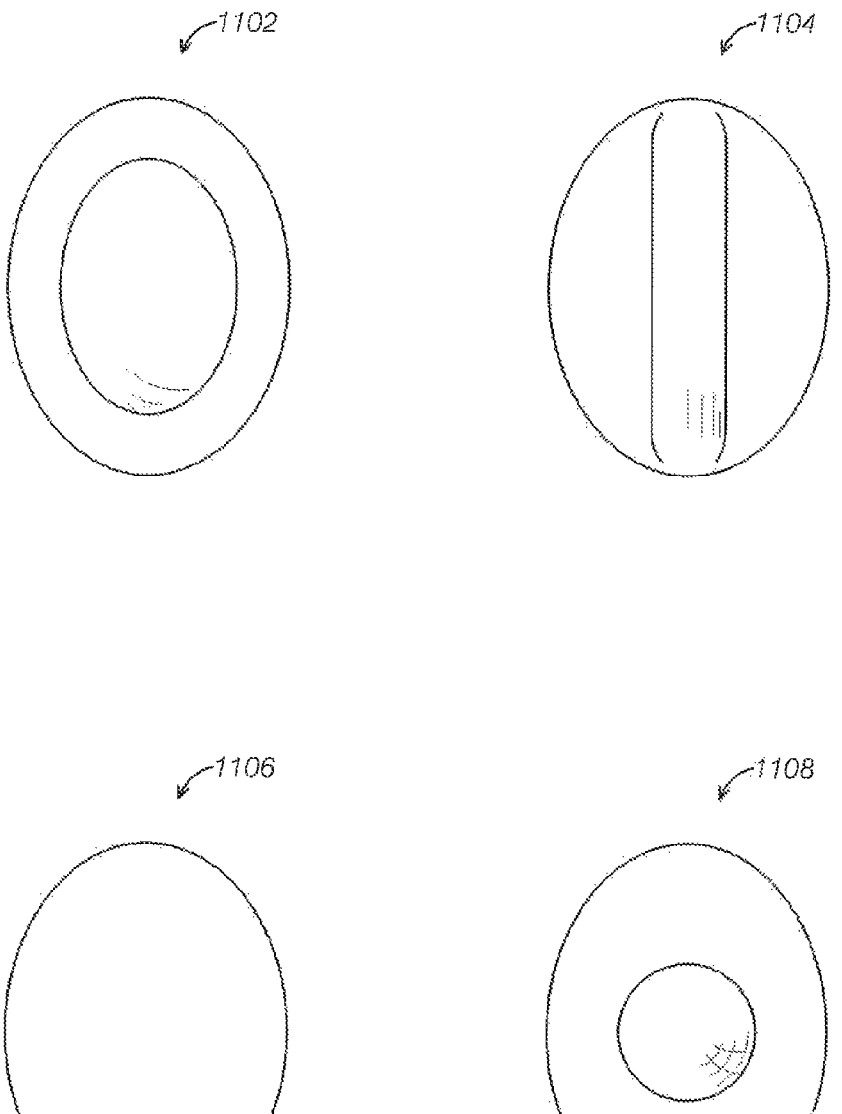
FIG. 11 illustrates perspective views of various embodiments of coupling pads.

The coupling pad can comprise a dome shape in profile. FIGS. 12A-D shows various possible shapes of the coupling pad, including a short dome in FIG. 12A, a high dome in FIG. 12B, a flat top in FIG. 12C, and a nub (e.g., oval nub, circular nub) in FIG. 12D. Other shapes and configurations are also possible (e.g., as shown in FIG. 11: Oval Num 1102, Ridge 1004, Dome 1106, and Round Nub 1108). Testing of the various configurations has shown that the short dome shape is comfortable for users.

Ultrasound Settings

There are four parameters that constitute the ultrasound settings. These are: treatment duration (in minutes), ultrasound frequency (in MHz), duty cycle (in % on-time) and acoustic intensity (in Watts/cm$^2$). These settings have been informed by literature review, clinical studies, numerical simulation, and bench testing. Prior devices were not used to provide therapeutic ultrasound at this location. The combination of ultrasound parameters disclosed herein can achieve the desired result while minimizing risk. For example, the parameters can provide the appropriate temperature rise while avoiding an overly high range.

Treatment Duration

Treatment duration was initially set to about 5-10 minutes or about 8 minutes, based on literature review demonstrating 5-10 minutes of ultrasound could have a profound impact on tissue blood-flow. Further, clinical work has demonstrated this is a sufficient length of time to promote increases in vaginal blood-flow. This duration also meets therapy use requirements (generated through prospective user interviews) to balance benefit and total time required in order to promote user compliance.

Ultrasound Frequency

The frequency of the ultrasound waveform delivered by the device can be about 0.5-2 MHz, or about 1 MHz, as this frequency has been shown to penetrate tissue to a depth of 3-5 cm before attenuation.

Duty Cycle

Duty cycle is the proportion of "on-time" of the ultrasound signal. (For example, a duty cycle of 50% means the ultrasound is pulsed and 'on' only 50% of the time.) Pulsed ultrasound therapy (i.e. duty cycles of 20% and 50%) may have a greater effect on tissue healing than continuous wave ultrasound (duty cycle=100%), as a duty cycle less than 100% may heighten the non-thermal biological effects.

Duty cycles of both 50% and 100% were initially tested in clinical studies. A 50% duty cycle can be preferred as numerical simulations, bench testing in tissue surrogates, and patient comments demonstrated that duty cycles greater than 50% could lead to adverse temperature effects if the device were used incorrectly.

Acoustic Intensity

The goal of the ultrasound therapy is to increase local vaginal blood flow 3-5 cm deep in the vaginal canal. Thus, the initial intensities to be tested were chosen based on those shown to increase blood flow at tissue depths greater than 3 cm. In some embodiments, the intensity is about 3.4 W/cm$^2$. Other intensities are also possible (e.g., about 1-4, about 1-3, about 2-3, about 1-2, about 1.3-1.9, about 0.5-2.5 etc.). In some embodiments, the power is about 2.6 Watts. The area of the coupling surface can be about 2 cm$^2$. Thus, the average intensity can be about 1.3 W/cm$^2$.

Transducer Shape

The shape of the ultrasound transducer dictates the form of the emitted ultrasound beam The clinical work has demonstrated that a diffuse application of ultrasound can, in some embodiments, provide better therapy by vasodilating as much of the vascular bed of the vaginal canal as possible.

Flat, disc-type transducers were considered and proved appropriate for the therapy application, as they can achieve the desired therapy effect and are cost-effective. Flat transducers are characterized by a 'natural focal length,' which is a function of the transducer size and ultrasound frequency. At this focal length acoustic intensity reaches a global maximum as the ultrasound beam transitions from a near-field signal (characterized by intensity turbulence) to a far-field, smooth and predictable signal. As the therapy can be a fixed frequency (e.g., 1 MHz) in some embodiments, the natural focal length for the transducer can be tuned by adjusting the transducer size. Thus, a flat, disc-type ultrasound transducer can be used.

A skilled artisan will understand that other transducer types (e.g., curved, transducer array, etc.) are also possible.

Development of a Coupling Pad Mold

Clear propagation of ultrasonic energy from the surface of the transducer through the coupling pad medium and into the target tissue can be dependent on the ultrasound waves encountering a minimized number of air gaps, bubbles, or defects, along the direction of travel. Each air gap or defect can cause incident energy to attenuate from scattering or absorption; thereby weakening the ultimate dose to the intended area.

Ported Cover

Figure 13:
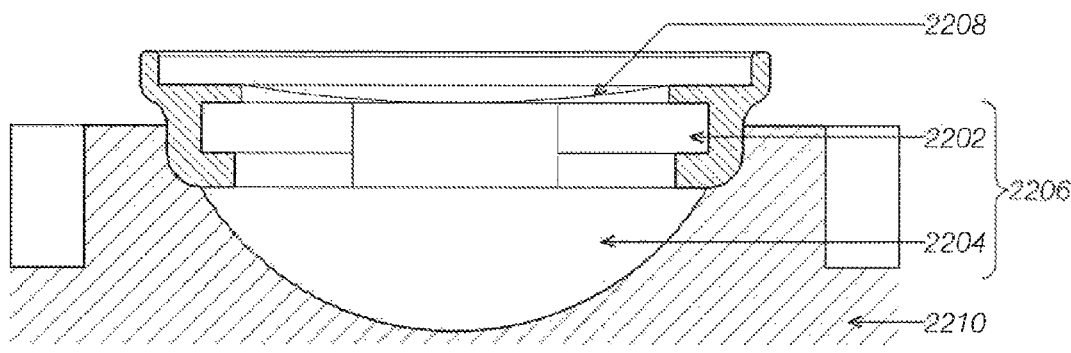
FIG. 13 shows a meniscus formed during curing of an embodiment of a coupling pad.

The coupling pad can be molded onto a support ring configured to provide structure to the coupling pad component. The support ring and coupling pad can together form the disposable component of the handheld device. Early efforts at molding the coupling pad into the support ring produced a significant meniscus in the coupling pad, which resulted in an air gap at the interface of the assembled transducer and coupling pad. Liquid coupling pad material can be cured in a mold (e.g., 3D printed mold). FIG. 13 shows the problematic meniscus 2208 formed in the curing coupling pad 2206, formed by the support ring 2202 and the liquid coupling material 2204 sitting in the mold 2210. In addition, curing of the coupling pad material 2204 in these molds 2210 frequently lead to trapped air bubbles within the coupling pad.

In order to minimize these deleterious effects, the following three molds were designed and fabricated.

Figure 14:
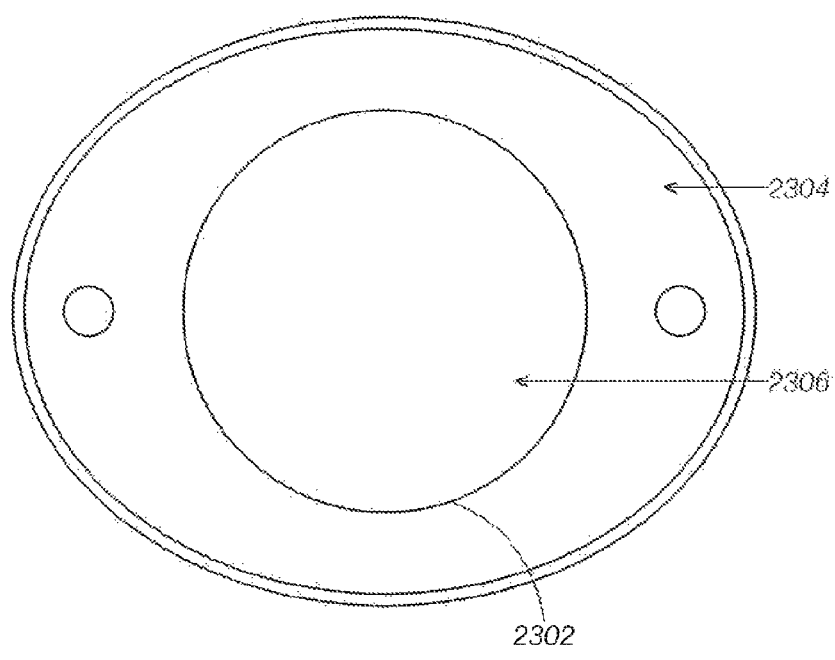
FIG. 14 depicts an embodiment of a coupling pad component.
Figure 15:
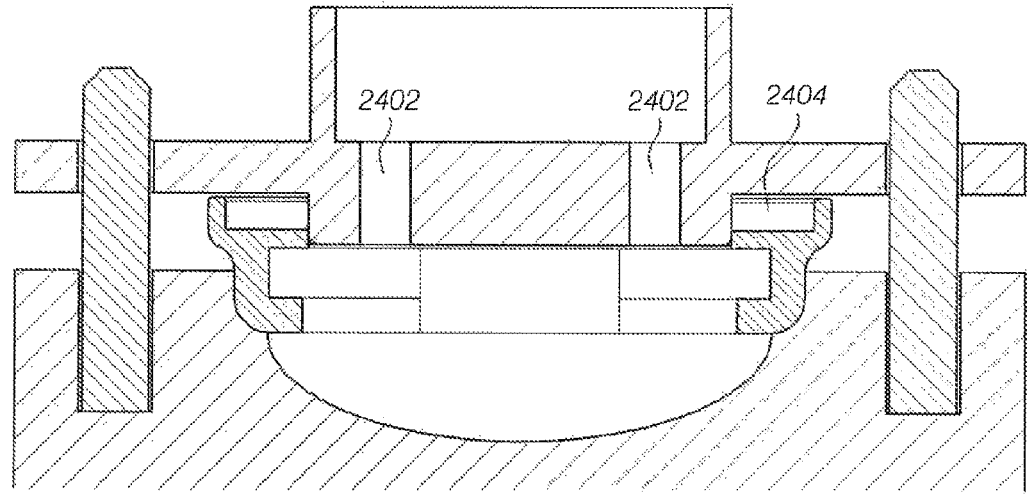
FIG. 15 illustrates an embodiment of an embodiment of a mold for forming a coupling pad.

To prevent the wall surface tension from forming a problem meniscus in an open-cavity mold, a top plate was added to the mold assembly. As shown in FIG. 14, this plate covers the hole 2302 in the support ring 2304 forming the transducer interface 2306 where the ultrasound transducer will subsequently seat against the coupling pad. FIG. 15 illustrates an embodiment of this mold cover design. Two ports holes 2402 are added to the plate 2404, so air and excess materials can flow out of the mold freely. Once hardened, the two port plugs, now full of material, can be sheared off, revealing a flat, even surface.

Figure 16:
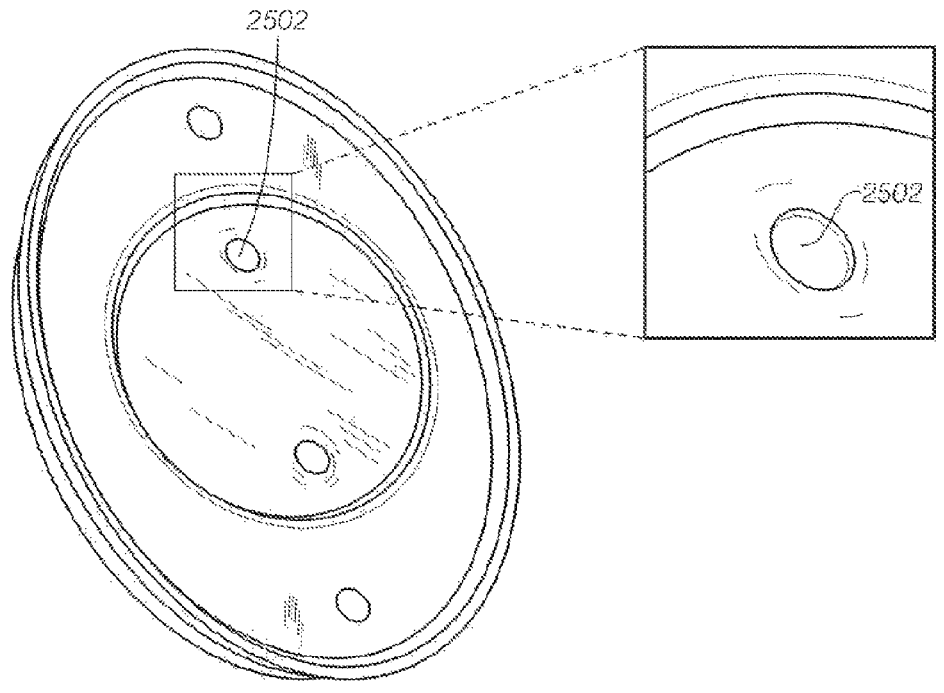
FIG. 16 shows an embodiment of a coupling pad component.

Although the Ported Cover design effectively eliminated the problem meniscus, the two ports can leave small blemishes on the surface of the cured agarose that contacts the transducer face, as shown in FIG. 16. These "rough spots" 2502 are undesirable, as they can cause a non-uniform seating of the transducer face to the agarose coupling pad and hence, a possible reduction in the ultrasound transmission through the coupling pad.

Ported Support Ring

Figure 17:
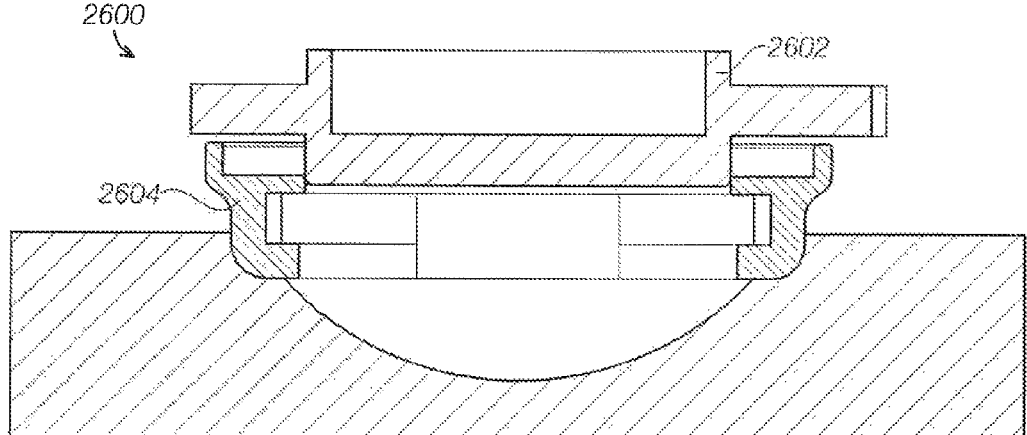
FIG. 17 depicts an embodiment of a mold for forming a coupling pad.
Figure 18:
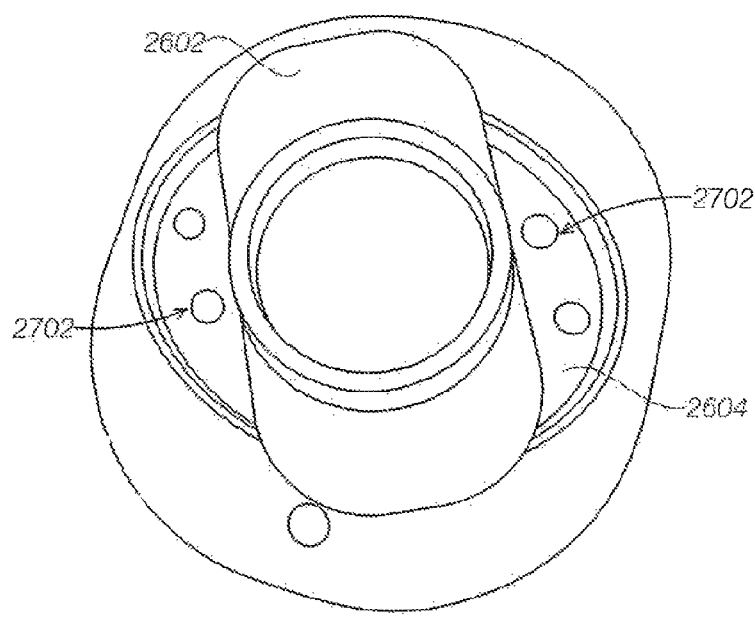
FIG. 18 illustrates an embodiment of a coupling pad component.

In the embodiment shown in FIGS. 17 and 18, the mold 2600 uses the same top plate 2602 that is used in mold 2400 of FIG. 15 in order to prevent the meniscus. The key difference in mold 2600 is that the port holes 2702 are now placed into the support ring 2604, itself, shown in FIG. 18. This change of port placement minimizes the problems that were encountered in mold 2400, and ensures a smooth transducer coupling surface.

Figure 19A:
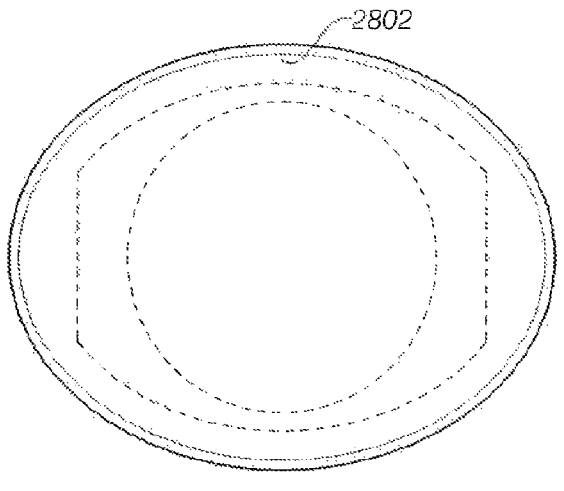
FIGS. 19A and 19B show various views of a coupling pad component.
Figure 19B:
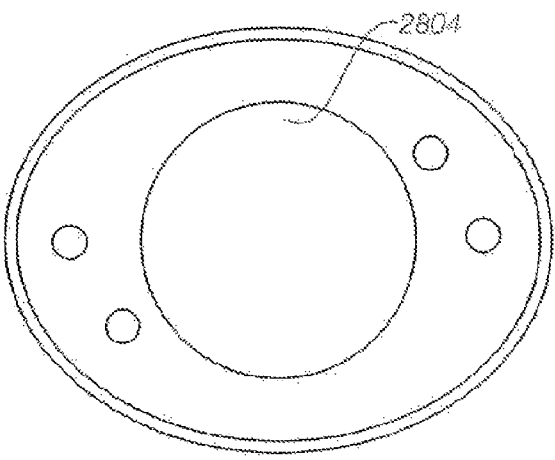

In mold 2600, the liquid coupling medium flows in through one port in the support ring 2604, fills the mold 2600, and flows out through the second vent hole when the mold cavity is full. This flow helps prevent air bubbles from being trapped in the cured coupling pad. This design consistently created bubble-free coupling pads more often than any previous mold design. A finished coupling pad/support ring assembly 2802 made using mold 2400 shown in FIGS. 19A and 19B. Note the planar, smooth rear surface 2804 of the coupling pad where the transducer face seats on assembly.

Top Fill

Figure 20:
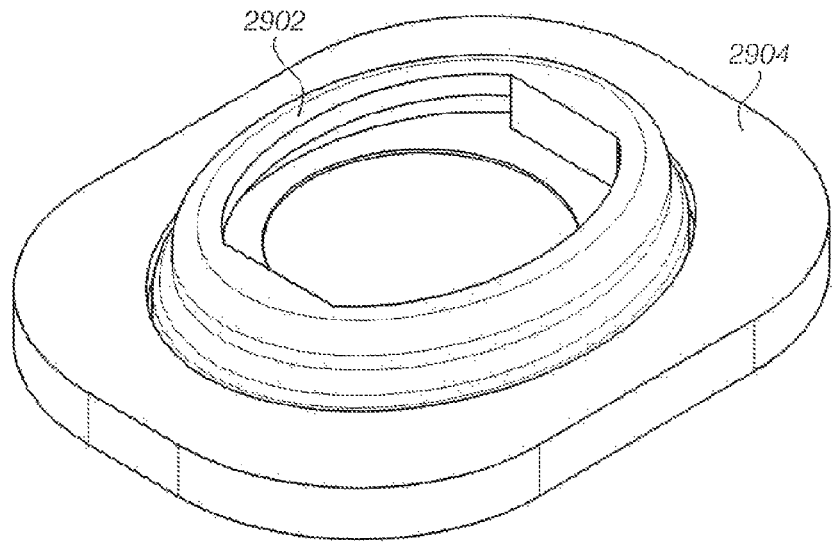
FIG. 20 depicts part of an embodiment of a mold for forming a coupling pad.
Figure 21:
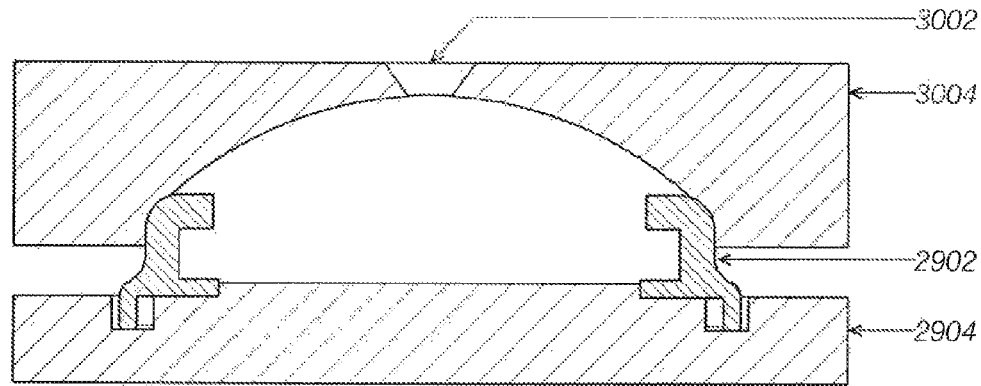
FIG. 21 illustrates an embodiment of a mold for forming a coupling pad.
Figure 22A:
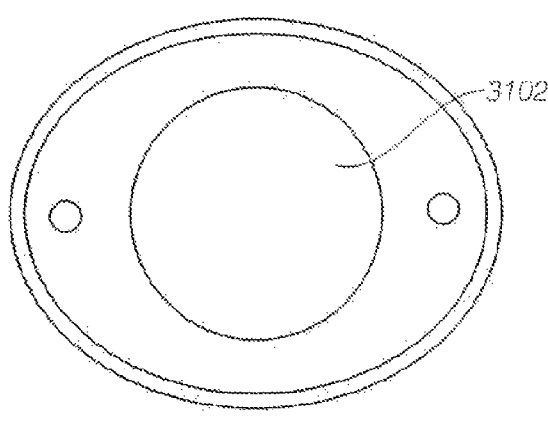
FIGS. 22A-22C show various embodiments of coupling pad components.
Figure 22B:
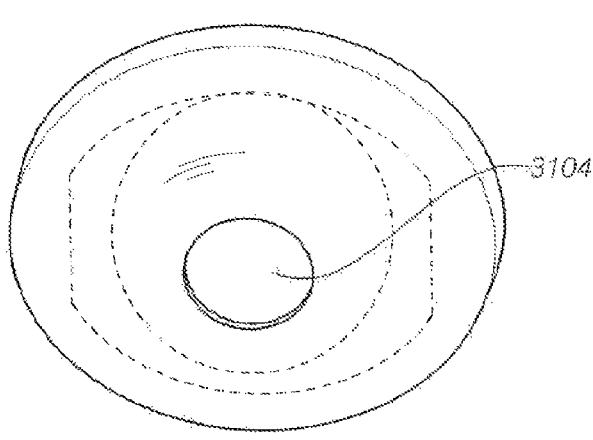
Figure 22C:
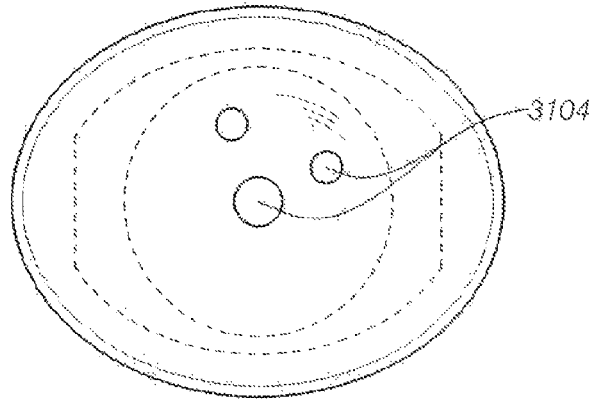

The top fill mold 3000 design, shown in FIGS. 20 and 21, takes the original mold design and flips the fill location 180 degrees. In this design, the ring 2902 snaps into a bottom plate 2904 or mold base, shown in FIG. 20. The liquid coupling medium 3004 flows in through a hole 3002 in the mold top 3003 leading to the top surface of the coupling pad and support ring assembly (FIG. 21). As shown in FIG. 22A, the top fill mold 3000 design can produce a perfectly flat and smooth surface 3102 that interfaces with the transducer. A potential downside to this design is that voids 3104 can form during curing, as shown in FIGS. 22B and 22C.

Figure 23:
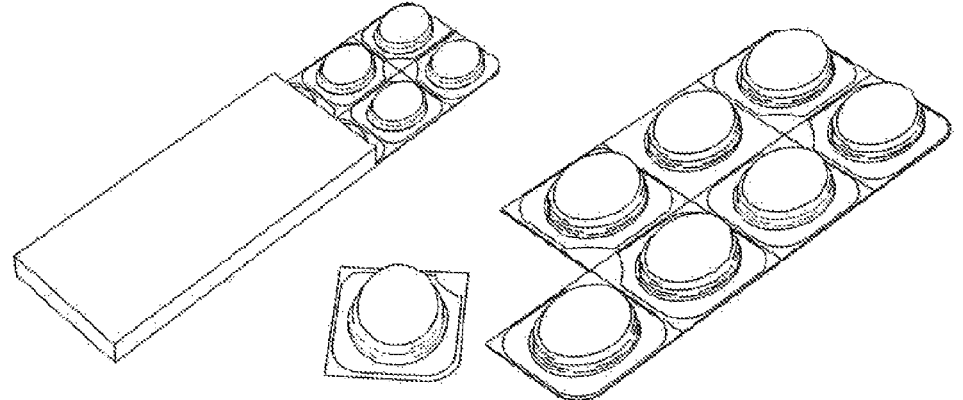
FIG. 23 depicts an embodiment of coupling pad component packaging.

FIG. 23 depicts an embodiment of coupling pad component packaging. The packaging can include a blister pack tray for holding the coupling pad components.

Figure 24:
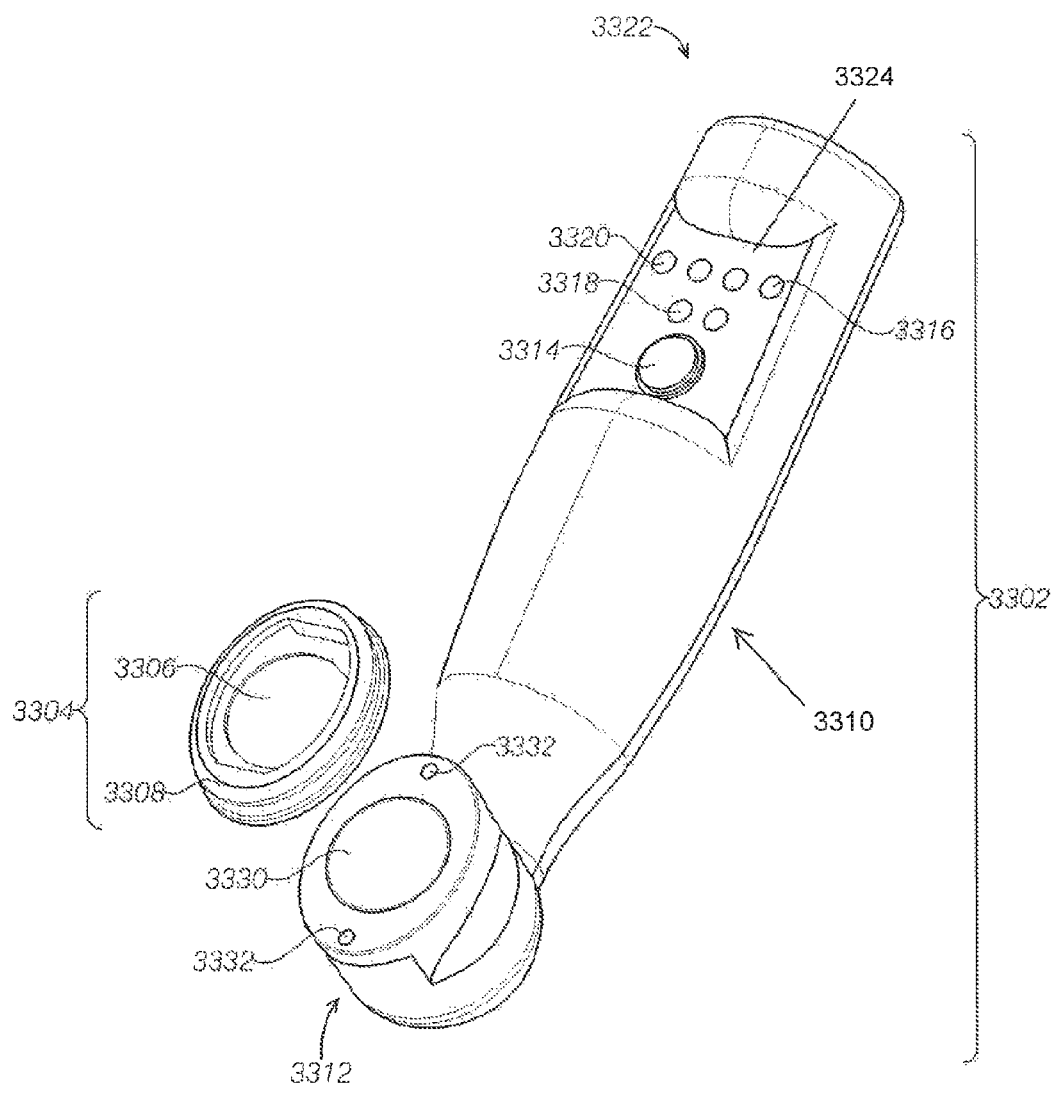
FIG. 24 illustrates another embodiment of an ultrasound device.

FIG. 24 illustrates another embodiment of an ultrasound therapy device 3300. The device 3300 comprises a main device portion 3302 and a coupling pad component 3304. Unless described otherwise, the device 3300 can comprise features or combinations of features of other ultrasound therapy devices described herein.

The coupling pad component 3304 comprises a coupling pad 3306 and a support ring 3308. As described herein, the coupling pad 3306 can be formed from a coupling pad material (e.g., liquid medium). The support ring 3308 can provide structure to the coupling pad and aid in its formation. In some embodiments, the coupling pad component is disposable.

The main device portion 3302 comprises a handle portion 3310 and a head portion 3312. The handle portion 3310 can be configured to fit in a patient's hand. The handle portion 3310 may comprise one or more controls or buttons.

Additional Embodiments

Additional embodiments of ultrasound devices are provided below. It will be appreciated that the various embodiments devices can comprise features or combinations of features described herein with respect to other embodiments of devices.

As shown in FIG. 24, the handle portion 3310 comprises a single button 3314. In some embodiments, the device 3300 can be activated by pressing button 3314. The device can be turned on and off by pressing button 3314. Turning on the device can initiate energy delivery at pre-set conditions and for a pre-set duration. In some embodiments, the device can be paused by pressing button 3314. For example, holding down button 3314 for a period of time (e.g., 1 second, 2 seconds, 3 seconds) can cause the device to be turned on and/or off. Simply pressing the button 3314 can pause ongoing energy delivery. Pressing the button 3314 again can resume treatment at the point at which it was paused.

The handle portion 3310 can comprise one or more indicator lights. As shown in FIG. 24, the handle portion 3310 can comprise a power indicator light 3316 configured to be illuminated when the device is on. The handle portion 3310 can comprise a battery indicator light 3318 configured to indicate battery status. The battery indicator light 3318 can change color to indicate battery status. For example, green can indicate a full charge. Yellow can indicate the device needs to be charged soon. Red can indicate the device does not have sufficient power to complete a therapy session. The handle portion 3310 can also comprise one or more 'therapy remaining' lights 3320 to indicate time left in treatment. The lights 3320 can all be illuminated at the start of treatment, and can shut off, one at a time, to indicate the amount of time that has passed. For example, given an 8 minute treatment time, all four lights 3320 are illuminated at the start of treatment. Every 2 minutes, one of the lights 3320 shuts off until they are all off at the end of the treatment. In some embodiments, the handle portion 3310 comprises 1, 2, 3, 4, 5, or 6 therapy remaining indicator lights.

As noted above, the handle portion 3302 can be configured to be held in a patient's hand during treatment. As such, the handle portion 3302 would be held near the front of the groin area. The controls and/or indicator lights can be positioned towards an end 3322 of the handle portion away from the head portion in order to provide a better view and easier access to the patient.

The control and/or indicator lights can be positioned in a recessed area 3324, as shown in FIG. 24. Such positioning can help a user easily maneuver their fingers to the area. A single button control can also allow the user to manage functionality of the device without needing a clear view of the controls.

In some embodiments, the controls or indicators can comprise a user interface for user input of treatment parameters. In some embodiments, the device can be remotely controlled by a smartphone, dedicated device controller, computer, tablet, or the like. In some embodiments, the device comprises digital displays indicating battery status, therapy remaining status, or device status.

In some embodiments, the head portion 3312 of the device 3300 comprises an ultrasound head 3330, as shown in FIG. 24. The ultrasound head 3330 can comprise an ultrasound transducer. The ultrasound transducer can be a flat, disc-type transducer. Other configurations (e.g., curved) are also possible. In some embodiments, the ultrasound transducer is a ceramic piezoelectric crystal. Other transducers are also possible. The transducer can have a diameter of about 15-25 mm, about 15 mm, about 20 mm, or about 25 mm. Other transducer sizes are also contemplated. The effective radiating area (Aer) of the transducer can be about 1.5-12 cm$^2$, 1.5-8 cm$^2$, 1.5-6 cm$^2$, 1.5-4 cm$^2$, or about 2 cm$^2$. In some embodiments, the ERA is about 2.0 cm$^2$. The beam non-uniformity ratio (Rbn) of the transducer can be about 7:1. In some embodiments, the natural focal length is about 30-100 mm, about 40-90 mm, about 40-80 mm, about 45-65 mm, about 40-600 mm, or about 50 mm.

The head portion 3312 also comprises attachment means for connecting to the coupling pad portion 3304. As shown in FIG. 24, the attachment means can comprise magnets on the head portion 3312 configured to engage with magnets 3332 (not shown) on the coupling pad portion 3304. Magnet attachment means can be easy to use and easy to clean as they may have a low profile. Other attachment means (e.g., hook and loop, snaps, straps, etc.) are also possible. For example, in some embodiments, the attachment means comprises a threaded connection between the head portion 3312 and the coupling pad portion 3304. The threaded connection can require a small turn to engage the two components. For example, ¼ turn or ½ turn can be used to engage the two components and put the coupling pad 3306 in acoustic connection with the ultrasound transducer 3330.

FIGS. 25A-E illustrate various views of an embodiment of a main device portion 3400 without the coupling pad portion 3304. FIG. 34A is a top view of the main device portion 3400 comprising a head portion 3402 and a handle portion 3404. The head portion 3402 comprises attachment means (e.g., magnets) 3406 for attaching head portion 3402 and coupling pad portion. The head portion 3402 also comprises an ultrasound head comprising an ultrasound transducer face 3408 for contacting a coupling pad. An outer portion of the head portion 3402 around the transducer face 3408 contacts the support ring when the coupling pad portion is attached to the head portion 3402. In some cases, the attachment means (e.g., magnet-based) 3406 is integrated into the device so that it is sealed (e.g., water tight sealed and/or hermetically sealed). Such sealing can protect the attachment means from damage when exposed to moisture, for example, during use and/or during cleaning of the device.

Figures 25A, 25B, 25C, 25D, 25E:
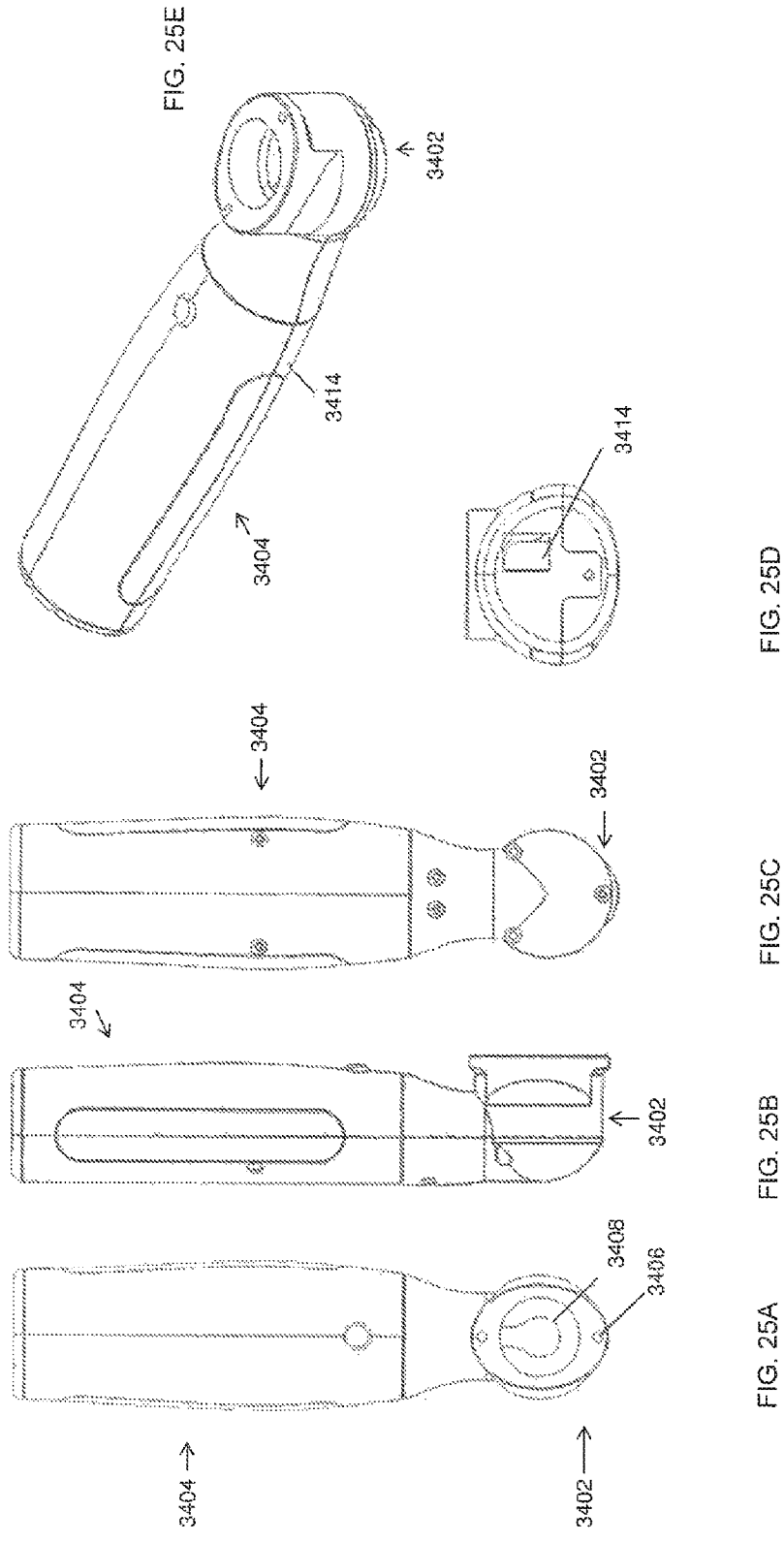
FIGS. 25A-25E depicts various views of an embodiment of a main device portion of an ultrasound device.

FIG. 25B is a side view of the main device portion. The main device 3400 can comprise plastic (e.g., Polyethylene, Polypropylene, Polystyrene, Polyester, Polycarbonate, Polyvinyl Chloride, Polymethylmethacrylate (PMMA), Polyetheretherketone (PEEK), etc.) with or without a silicone overmold 3410, shown in FIG. 25B, over certain portions of the handle portion 3404 for ease and comfort during use. FIG. 25C shows a back view of the main device 3400, showing the head portion 3402, handle portion 3404 and silicone overmold 3410. The device can have a length of about 200-300 mm, 225-275 mm, about 200 mm, 210 mm, 220 mm, 230 mm, 240, mm, or 250 mm. The device can have a width of about 20-60 mm, 30-40 mm, or about 37 mm. The device handle can have a thickness of about 20-60 mm, 30-40 mm or about 33 mm.

As shown in FIG. 25C, the base of the head portion 3402 comprises a greater surface area or diameter than a top part of the head portion, near the transducer face 3408. This greater area at the base of the head portion 3402 can allow for ultrasound transducer components and circuitry while still allowing a more compact shape for the portion of the head portion 3402 that will be near the treatment area. It will be appreciated that, in some embodiments, ultrasound circuitry is provided external to the device.

FIG. 25D depicts an end or back view of the main device 3400, looking towards the handle portion 3404. The bottom surface 3414 of the device 3400 can comprise a port 3412 that can be used for charging the device. The port 3412 can be used to charge a rechargeable battery in the device via a corded connection. A standard outlet or USB can be used the charge the device. In some embodiments, the device can be used when plugged in. In some embodiments, the device cannot be used when plugged in.

FIG. 25E shows a top perspective view of device 3404 showing handle portion 3404 and head portion 3402. Control or button 3406 is shown on handle portion 3402. Control 3406 is shown closer to head portion 3402 than in the embodiment of FIG. 24. Handle portion can also comprise indicator lights, which are not shown in FIG. 25E. Handle portion 3404 extends towards the head portion and tapers at a neck portion 3414 of the device 3400. The smaller diameter of the neck portion 3414 can allow for ease of positioning the head portion at the treatment area. In some embodiments, the neck portion or another portion of the device comprises a strain gauge or pressure sensor to inform the user if the head portion is being placed into sufficient contact with the treatment area. For example, the device 3404 can be configured to inform the user whether not enough and/or too much pressure is applied by the device 3404 (i.e., head portion 3402) to the treatment area. In some embodiments, the strain gauge and/or pressure sensor is configured to provide feedback to the user regarding a quality and/or sufficiency of contact between the coupling pad and the user's tissue. In some cases, the strain gauge and/or pressure sensor may be operationally coupled to a processor(s) of the device 3404 such that the processor(s) receives feedback from the strain gauge, determines whether there is sufficient contact (e.g., as dictated by software instructions), and sends one or more signals to one or more indicators (e.g., visual, audible and/or tactile indicators) of the device 3404 to inform the user.

FIGS. 26A-26D show various views of an embodiment of a support ring 3500 before coupling pad material has been molded into the support ring. FIG. 26A shows a top view of the support ring 3500. The ring 3500 comprises an ovular shape in FIG. 26A, but other shapes (e.g., circular, rectangular, square, etc.) are also contemplated. A length of the support ring 3500 can be about 30-60 mm, about 40-50 mm, about 45 mm, about 46 mm, or about 47 mm. In some embodiments, the length of the support ring 3500 is about 46.6 mm. A width of the support ring 3500 can be about 20-50 mm, about 30-40 mm, about 35 mm, about 36 mm, or about 37 mm. In some embodiments, the width of the support ring 3500 is about 37 mm. The opening 3502 in support ring 3500 will be filled in by coupling pad material and, thus, represents the area of the coupling pad that will engage the transducer face. Other support ring designs may comprise plates or other features obscuring a portion of window 3502. By not having such a feature, better coupling between the transducer and coupling pad is enabled. Additionally, not having such a feature improves manufacturability as injection molding can be used and material cost decreases. In some embodiments, not having a backing plate or other similar feature in the support ring can cause the coupling pad to fall out of the support ring if handled too often or too rigorously. In single use embodiments, this can be a nice feature to prevent re-use of the coupling pad. The support ring can comprise a plastic material (e.g., HDPE, Polyethylene, Polypropylene, Polystyrene, Polyester, Polycarbonate, Polyvinyl Chloride, Polymethylmethacrylate (PMMA), Polyetheretherketone (PEEK), etc.).

FIG. 26B shows a bottom view of the support ring 3500. The bottom surface 3504 can be configured to mate with the head portion of the main device. The bottom surface 3504 comprises attachment means 3506, such as magnets, configured to engage attachment means of the head portion of the main device. As noted above, other attachment means, such as a threaded connection, are also possible.

FIG. 26C depicts a top perspective view of the support ring 3500. The support ring 3500 can have rounded edges along a perimeter of the device to improve user comfort. FIG. 26D depicts a side view of the device. FIG. 26D shows a slight taper to the shape of the device as it extends from the bottom surface towards the top surface. This shape can allow for good connection to the head portion while maintaining comfort for the user.

Figures 26E, 26F:
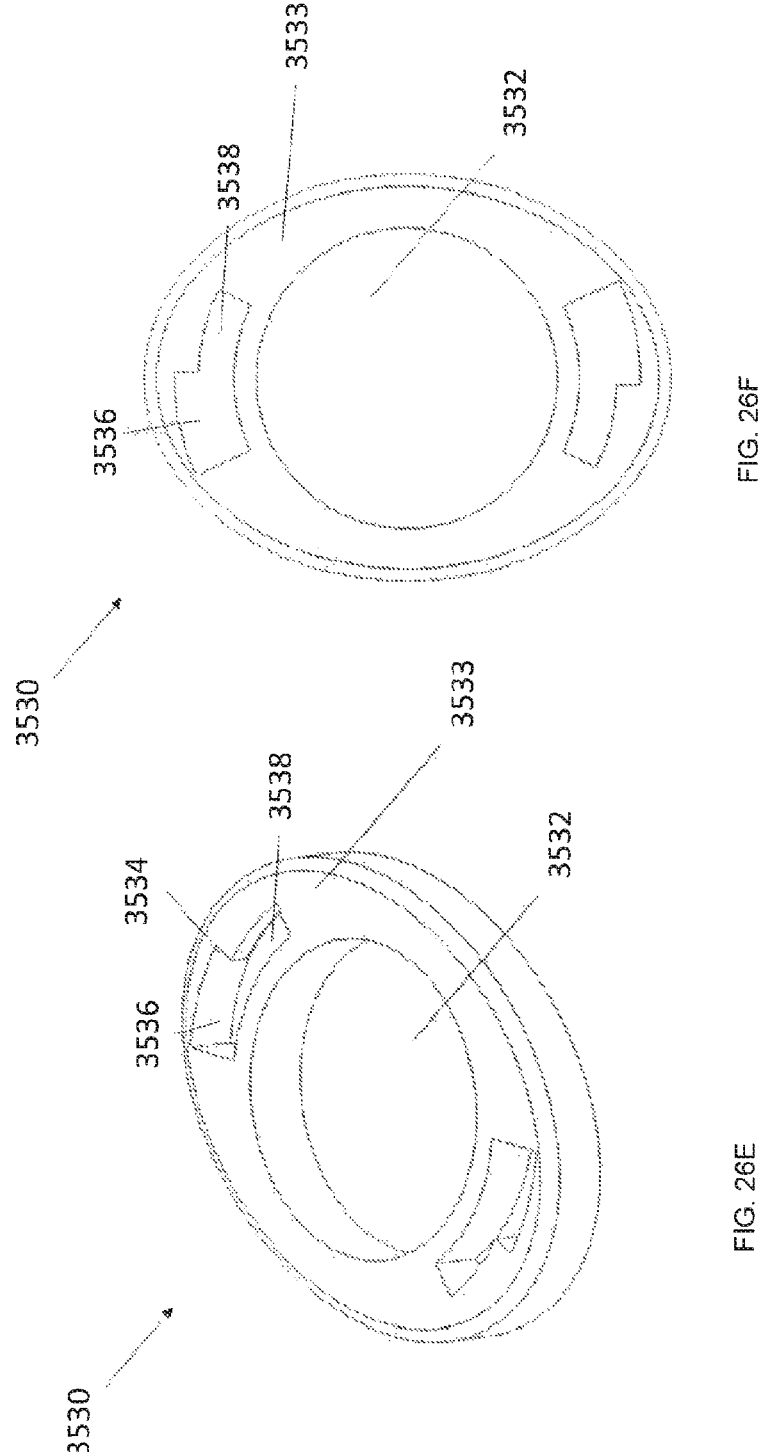

FIGS. 26E-26I illustrate another embodiment of an attachment means for attaching a support ring and coupling pad to an ultrasound transducer head. FIGS. 26E and 26F depicts various views of an ultrasound device transducer support 3530. FIG. 26E shows a top perspective view of the transducer support 3530; and FIG. 26F shows a top view of the transducer support 3530. The device transducer support 3530 is the portion of the ultrasound device that will connect to the coupling pad component creating the acoustic coupling between the transducer and the coupling pad. The transducer support 3530 includes an opening 3532 in the center, in which the transducer will be positioned. Thus, the dimensions of the opening 3532 can correspond to the dimensions of the transducer face. The inner surface of the opening 3532 can also be configured to correspond to the shape of the transducer. The transducer support 3530 extends from the opening 3532 in a radial direction from the center of the opening to create a ring around the opening 3532. This surface 3533 can comprise an ovular shape as shown in FIGS. 26E and 26F. Other shapes (e.g., rectangular, square, circular, etc.) are also possible. The transducer support 3530 comprises two slots 3534 comprising a wide portion 3536 and a narrow portion 3538. The slots 3534 are configured to engage tabs 3542 on the support ring embodiment shown in FIGS. 26G-26I.

Figures 26G, 26H, 26I:
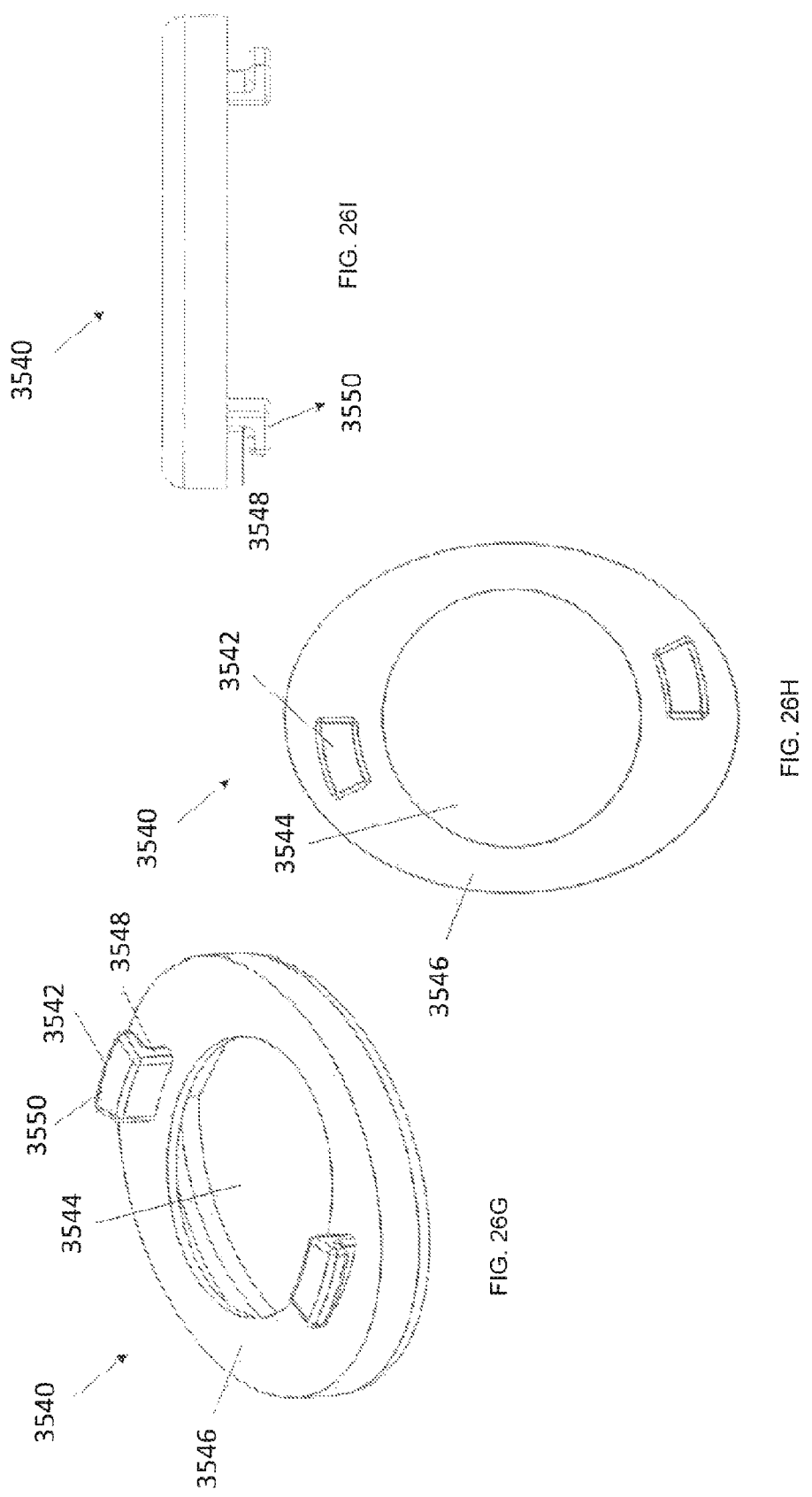

FIGS. 26G-26I illustrate various views of an embodiment of a support ring 3540. FIG. 26G shows a top perspective view of the support ring; FIG. 26H shows a top view of the support ring; and FIG. 26I shows a side view of the support ring. The support ring 3540 comprises an opening 3544 configured to receive a coupling pad. This area represents the area of the coupling pad that will interface with the transducer. The support ring 3540 extends outwardly from the opening 3544 in a radial direction from the center of the opening 3544. This surface 3546 of the support ring 3540 will interface with the transducer support, for example shown in FIGS. 26E and 26F. The support ring 3540 comprises an ovular shape in FIGS. 26G-26I, but other shapes are also possible, as described above. In some embodiments, the shape of the support ring and the transducer face are configured to correspond such that one doesn't extend much past the other. This correspondence can create a more comfortable experience for the user as the device will have a sleek exterior. The support ring 3540 comprises tabs 3542 configure to interact with slots 3534 on the transducer face. A narrow portion 3548 of the tab extends from support ring surface 3546 and widens to form a wide portion 3550 of the tab. The wide portion 3550 of the tab can be configured to be inserted into the wide portion 3536 of a slot on the transducer support. Rotating the support ring 3540 relative to the transducer support (e.g., ¼ turn, ½ turn, ¾ turn, 1 turn) can slide narrow portion 3548 of the tab into the narrow portion 3538 of the slot, locking the support ring and transducer support in place relative to one another. The tabs 3542 are shown with a shape resembling a portion of an annulus. Other shapes are also possible.

Figures 27A, 27B, 27C, 27D:
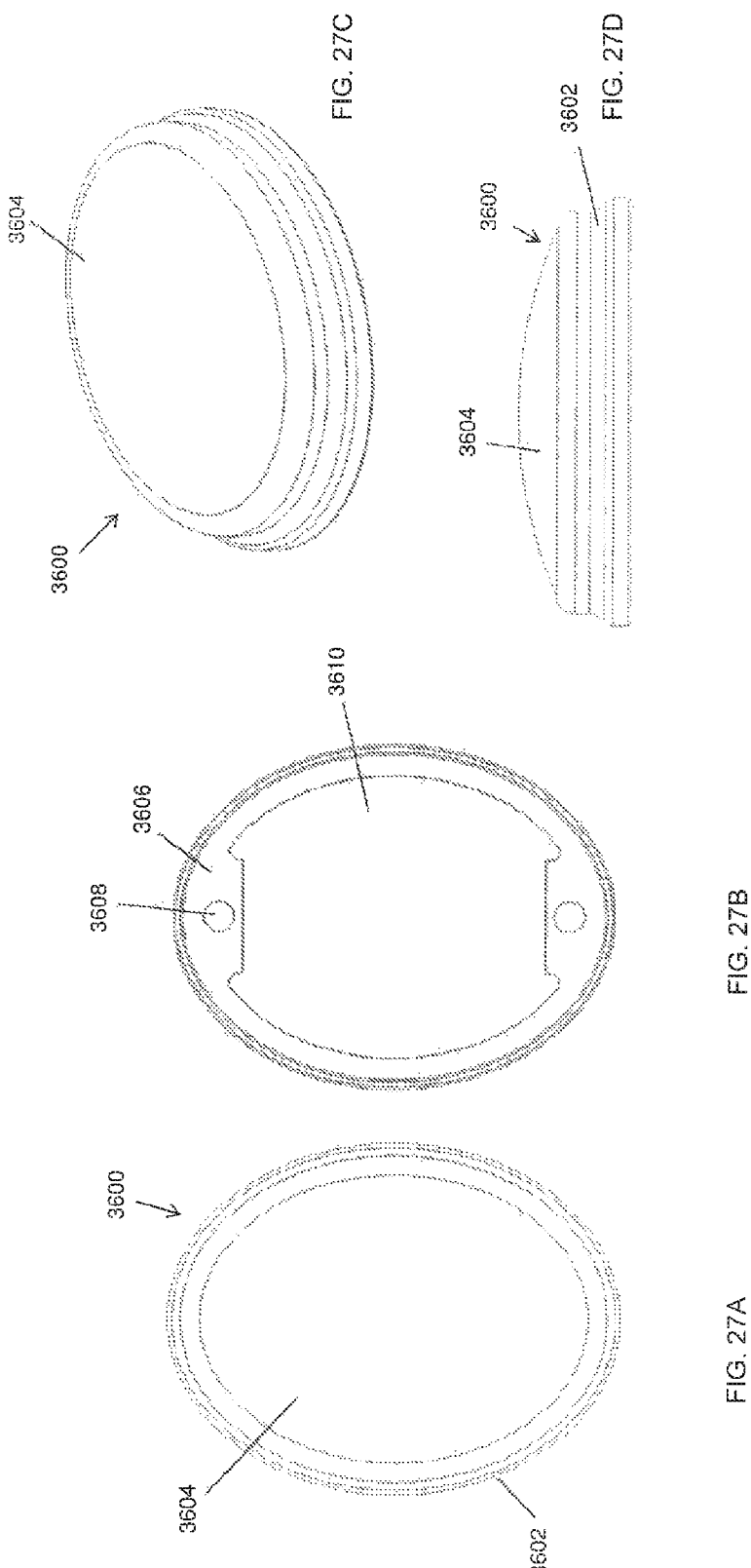
FIGS. 27A-27D illustrate various views of an embodiment of a coupling pad component.

FIGS. 27A-D depict various views of a coupling pad portion comprising a support ring 3602 with a coupling pad 3604 molded into the support ring. FIG. 27A illustrates a top view of the coupling pad portion 3600 comprising the coupling pad 3604 and the support ring 3602. The coupling pad can have a length of about 30-50 mm, about 35-55 mm, or about 47 mm. The coupling pad can have a width of about 20-40 mm, about 25-35 mm, or about 36 mm. The top surface of the coupling pad shown in FIG. 27A is the portion configured to engage the treatment area of the patient. The coupling pad can be molded from a liquid coupling material which can comprise one or a combination of agarose (e.g., 2-3% agarose, 1-2% agarose, 3-4% agarose or 2.5% agarose), silicone (e.g., with a Shore 00-20, Shore 10A, Shore 20A, or Shore 30A hardness), and water. Other materials are also possible, as described above (e.g., glycerin, CPC, etc.). In some embodiments, the coupling pad comprises 2% agarose with a lower concentration agarose coating the top and bottom surface to increase their lubricity.

FIG. 27B illustrates a bottom view of the coupling pad portion 3600. FIG. 27B shows a bottom surface 3606 of the support ring. The bottom surface 3606 comprises attachment means, such as magnets 3608, configured to engage with corresponding attachment means on a head portion of the main device. The bottom surface 3610 of the coupling pad represents that area that will interface with the ultrasound transducer. In some embodiments, a surface area of the coupling pad that interfaces with the ultrasound transducer is about 3-7 cm$^2$, 4-6 cm$^2$, 5 cm$^2$. In some embodiments, the surface area is about 4.9 cm$^2$.

FIG. 27C shows a top perspective view of the coupling pad portion 3600 comprising coupling pad 3604 and support ring 3602. FIG. 27D depicts a side view of the coupling pad portion 3600 comprising coupling pad 3605 and the support ring 3602. The coupling pad can have a convex, rounded, dome shape. The coupling pad can have a height (above support ring) of about 1-8 mm, about 3-8 mm, about 4-7 mm, or about 6.5 mm. The shape of the coupling pad can allow the user to self-navigate the device to the proper position near the vagina, at the introitus. In some embodiments, the user navigates to the proper positioning based solely on touch; thus, intuitive positioning can be useful for ensuring proper device use. Other coupling pad configurations are also possible (e.g., taller or shorter dome, central nub, flat top dome, ridge, etc.)

Figure 28:
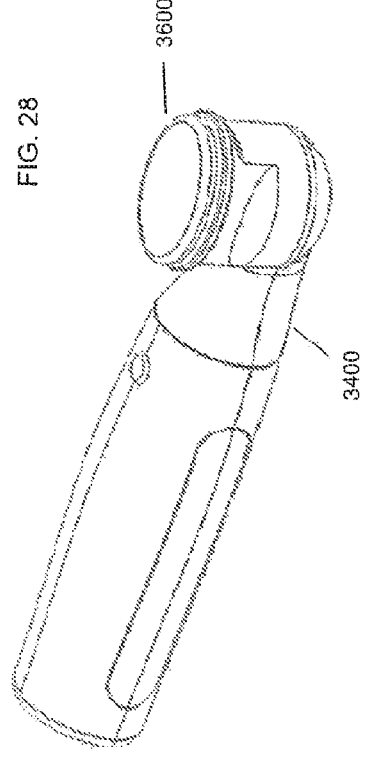
FIG. 28 depicts an embodiment of an ultrasound device.

FIG. 28 illustrates a top perspective view of an assembled ultrasound device comprising coupling pad portion 3600 attached to main device portion 3400.

The following figures depict further embodiments of a coupling pad. It can be important for the coupling pad to maintain self-lubrication throughout the duration of the treatment. Maintained lubrication can prevent hot spots caused by ultrasound standing waves and can promote better acoustic coupling to the patient's tissue.

Figure 29:
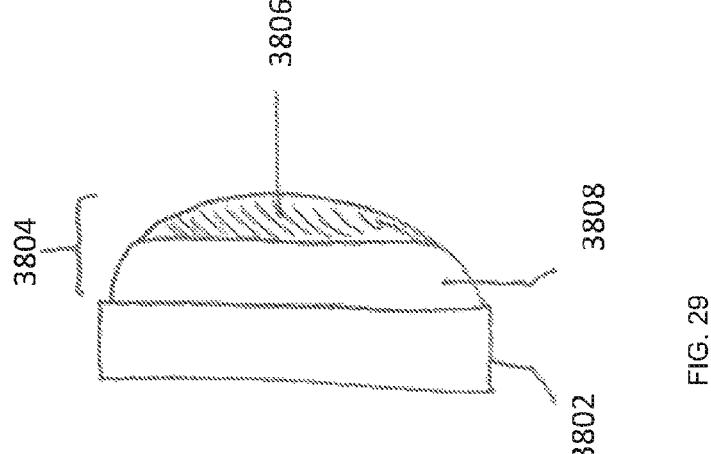
FIG. 29 shows an embodiment of a coupling pad component.

FIG. 29 shows an embodiment of a coupling pad component 3800 comprising a support ring 3802 and a coupling pad 3804. The coupling pad 3804 comprises an outer portion 3806 and an inner portion 3808. The outer portion 3806 is configured to interface with the patient's tissue. The inner portion 3808 is positioned closer to the support ring and the device. The outer portion 3806 can comprise a different material from that of the inner portion 3808. In some embodiments, the outer portion 3806 is configured to change phase from solid to liquid at or around (e.g., just above) body temperature. For example, the material can be solid phase at around 70°-85° F. The material can melt at about 85° F. This phase change to liquid can provide a layer of lubrication between the inner portion 3808 and the patient's tissue. In some embodiments, the colors of the two materials are different so a user can quickly see that a pad has been used. For example, in some embodiments, the inner portion 3808 can comprise agarose and the outer portion 3806 can comprise coconut oil. Generally, coconut fats belong to the unique group of vegetable oils called lauric oil about 44-51%. Laurie acid ($CH_3(CH_2)_{10}COOH$) is known as small molecule fatty acid (<14:0) which contains short or medium chain of saturated fatty acid. Other chemical compositions of coconut oil belong to myristic acid (16-19%), caprylic acid (9.0-9.5%), palmitic acid (8.0-9.5%), oleic acid (5-6%), capric acid (5-10%), steric acid (3.0-3.5%) and linoleic acid (1.0-1.5%), respectively. Other materials for the inner portion 3808 are also possible, such as those described above with respect to coupling pad materials.

Figures 30A, 30B:
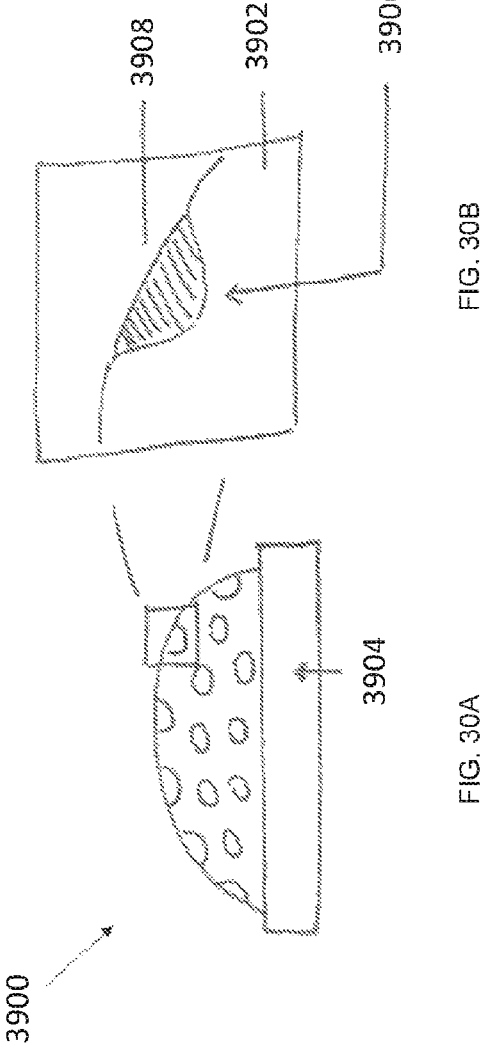
FIGS. 30A and 30B show another embodiment of a coupling pad component.

FIGS. 30A and 30B illustrate another embodiment of a coupling pad component 3900 comprising a coupling pad 3902 and a support ring 3904. The coupling pad 3904 comprises pockets 3906 pre-formed in the coupling pad. FIG. 30B shows an expanded view of pocket 3906. The pockets 3906 can be filled with an ultrasound conductive medium 3908 (e.g., ultrasound gel, mineral oil, or other sonolucent and viscous material). Including the ultrasound conductive material in pre formed pockets can prevent lubrication from an ultrasound conductive material (e.g., ultrasound gel) from rubbing off at first contact with the patient's tissue, which can thereby enhance acoustic coupling during treatment. The pockets can be shaped as circles, spheres, ellipsoids, ellipses, or have other configurations. The pockets can be about 0.5-3 mm in diameter.

FIGS. 31A and 31B show another embodiment of a coupling pad component 4000 comprising a coupling pad 4002 and a support ring 4004. The coupling pad 4000 comprises an additive 4006 (e.g., a lubricant). The additive can be driven to an outer surface of the coupling pad when the ultrasound is active via the mechanism of sonophoresis. This action is shown in FIG. 31B. An ultrasound wave 4008 is shown propagating towards the outer surface of the coupling pad. Arrows 4010 indicate the movement of the additive causing a layer of lubrication 4012 at the patient's tissue. The sonophoresis of the additive can allow the coupling pad to maintain a layer of lubrication between the outer surface of the coupling pad and the patient's tissue over the course of the treatment, which can maintain and/or enhance acoustic coupling.

Figure 32B:
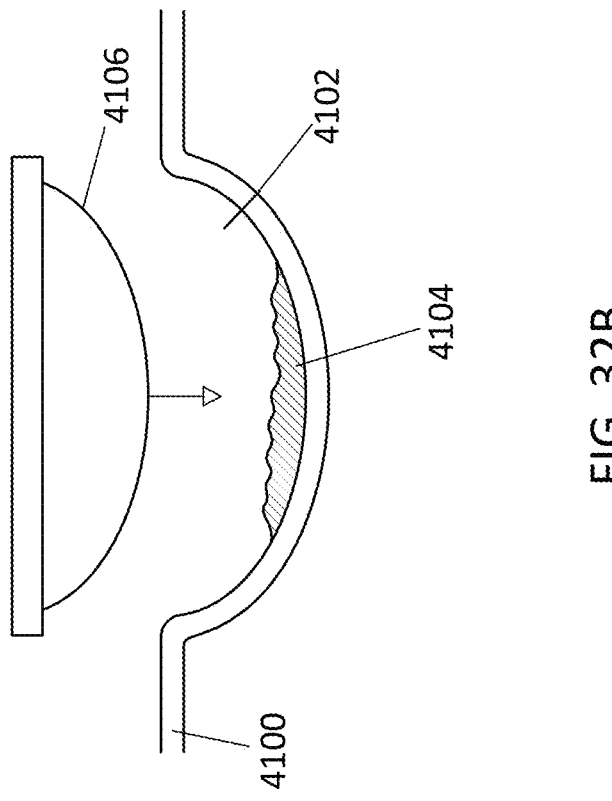
FIGS. 32A and 32B depicts embodiments of coupling pad component packaging.
Figure 32A:
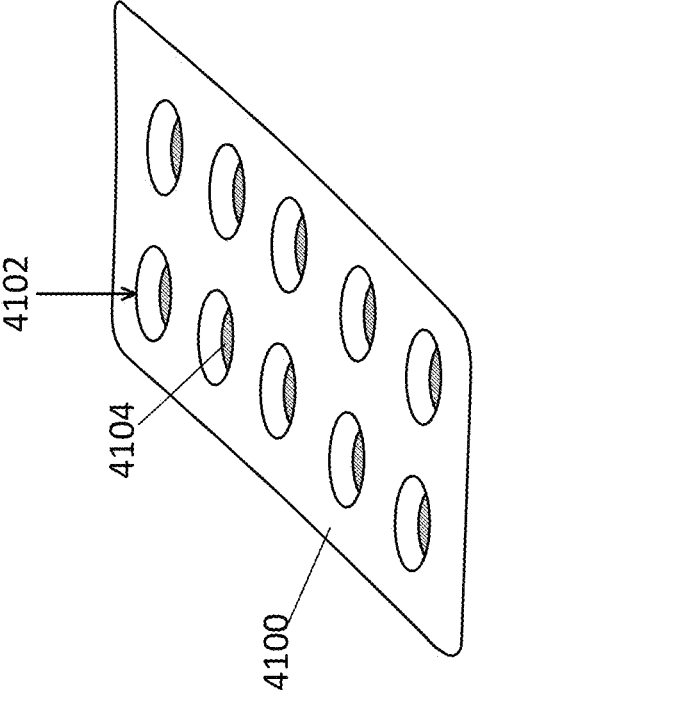

FIGS. 32A and 32B show an embodiment of coupling pad component packaging that can aid in lubrication of the coupling pad. As shown in FIG. 32A, a blister pack tray 4100 for holding the coupling pad component is provided. Each depression 3202 in the tray if filled with an ultrasound conductive material 4104 (e.g., ultrasound gel, mineral oil, etc.). FIG. 32B shows how the coupling pad component is placed in the blister pack tray 4100. The outer surface of the coupling pad 4106 is placed into the ultrasound conductive material 4104 in the depression 4102. This type of storage can 'prime' the coupling pad by adding a thin film of lubricant to the outer surface, which can enhance acoustic coupling between the coupling pad component and the patient's tissue.

Figures 33A, 33B:
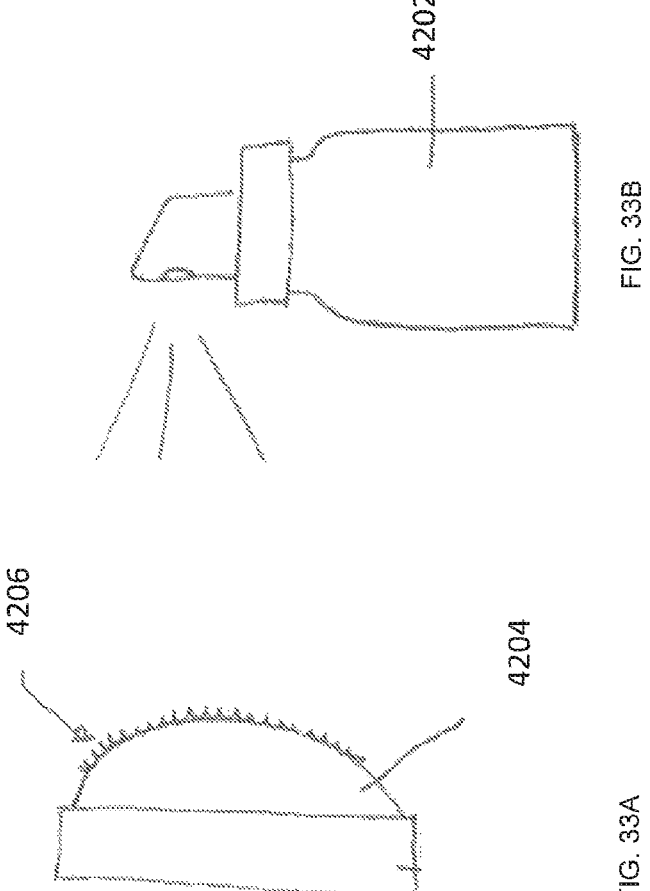
FIGS. 33A and 33B show embodiments of coupling pad component lubrication.

FIGS. 33A and 33B illustrate an embodiment in which a spray bottle of lubricant 4202, shown in FIG. 33B, is used to spray lubricant onto a surface of the coupling pad 4204.

Adding lubricant can add a layer of lubricant 4206 to an outer surface of the coupling pad, shown in FIG. 33A. Other means for adding a layer of lubricant are also possible (e.g., squirt bottle, pre-lubricated wipes or pads, etc.).

Figure 34:
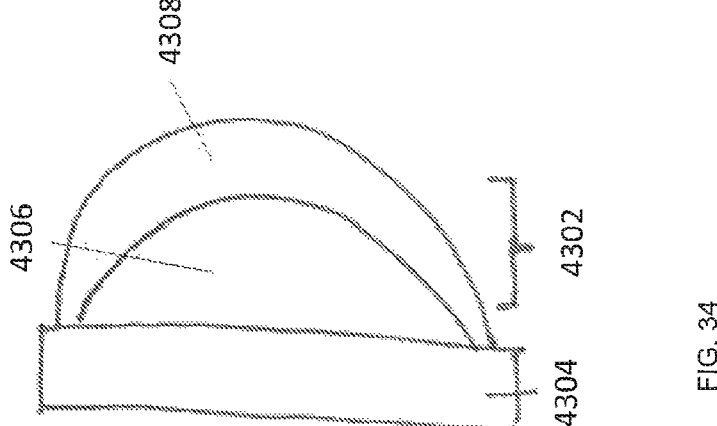
FIG. 34 illustrates another embodiment of a coupling pad component.

FIG. 34 illustrates an embodiment of a coupling pad component 4300 comprising a support ring 4304 and a coupling pad 4302. In this embodiment, the coupling pad comprises two different materials, as described above. A first portion 4306 of the coupling pad comprises a first material, and a second portion 4308 of the coupling pad comprises a second material, different from the first. The different materials can comprise different concentrations of the same material. For example, the first portion 4306 can comprise 2% agarose; and the second portion can comprise 0.5% agarose. The second portion 4308, which contacts the patient's tissue, can comprise a more lubricious material than the first portion 4306, which can provide enhanced acoustic coupling.

Alternative Coupling Pad Component Embodiments

The following figures depict an additional coupling pad component embodiments. The coupling pad components shown below can allow for attachment to any ultrasound transducer head. Unless otherwise described, the coupling pad component can comprise one or a combination of features of other coupling pads and related coupling pad components described herein.

Figures 35A, 35B, 35C, 35D:
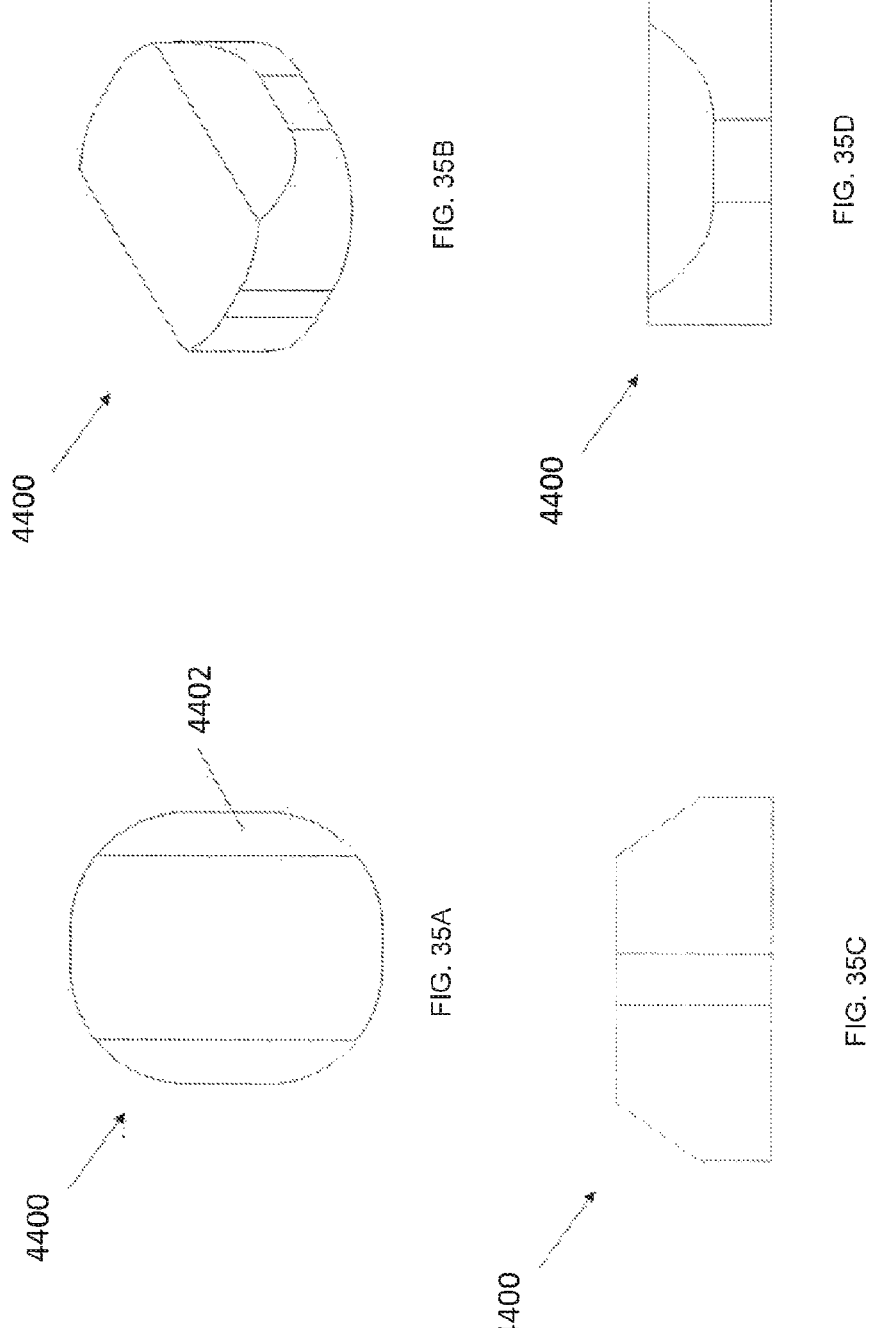
FIGS. 35A-35D depicts various views of an embodiment of a coupling pad.

FIGS. 35A-35D illustrate various views of a coupling pad 4400. FIG. 35A shows a top view of the coupling pad 4400. The coupling pad 4400 comprises a generally rectangular shape with rounded corners. This shape can provide a large surface area to interface with patient tissue and with an ultrasound transducer while still maintaining a smooth exterior. Other shapes (e.g., ovular, square, rectangular) are also possible. The coupling pad 4400 can comprise chamfered edges 4402 which can help secure the device in a coupling pad holder. FIG. 35B shows a top perspective view of the coupling pad. The top surface of the coupling pad is the portion configured to interface with the patient's tissue. The coupling pad can have a thickness of about 5-25 mm, about 10-20 mm, or about 15 mm. The coupling pad can have a length of about 25-55 mm, about 30-50 mm, about 35-45 mm, or about 40 mm. The coupling pad can have a width of about 15-45 mm, about 20-40 mm, about 25-35 mm, or about 30 mm. A length less than about 40 mm can help prevent ultrasound application to the urethra or clitoris and can help with self-navigation. FIG. 35C shows a front view of the coupling pad, showing the chamfered edge 4402. The edge 4402 can be chamfered at an angle of about 35-55 degrees or about 45 degrees. FIG. 35D shows a side view of the coupling pad 4400.

FIGS. 36A-36D illustrate various views of an embodiment of a top portion 4500 of a coupling pad holder. FIG. 36A shows a top view of the top portion 4500. The top surface includes opening 4502 through which the top surface of the coupling pad is to be inserted. The opening 4502 is about 25-55 mm, about 30-50 mm, about 35-45 mm, or about 40 mm long. The opening 4502 is about 15-45 mm, about 20-40 mm, about 25-35 mm, or about 30 mm wide. FIG. 36B shows a bottom view of the top portion 4500. The bottom surface comprises opening 4504 within which a bottom surface of the coupling pad will sit. In some embodiments, the bottom surface 4506 of the coupling pad is configured to be flush with the bottom surface 4506 of the top portion 4500. The opening 4504 represents the portion of the coupling pad that will interface with the ultrasound transducer. The bottom surface 4506 can comprise an attachment mechanism, such as magnets 4508, configured to interact with a corresponding mechanism on a bottom portion of the coupling pad holder. The bottom view of FIG. 36B also shows that the bottom opening 4504 is greater than the top opening 4502. This smaller top opening allows the chamfered edges of the coupling pad to seat in the top opening 4502. FIG. 36C shows a top perspective view of the top portion 4500. The top portion 4500 can generally have rounded surfaces and edges, providing comfort to the user during use of the device. FIG. 36D illustrates a front view of the device; and FIG. 36E illustrates a side view of the device, also showing the rounded surfaces and edges.

Figures 37A, 37B, 37C, 37D, 37E:
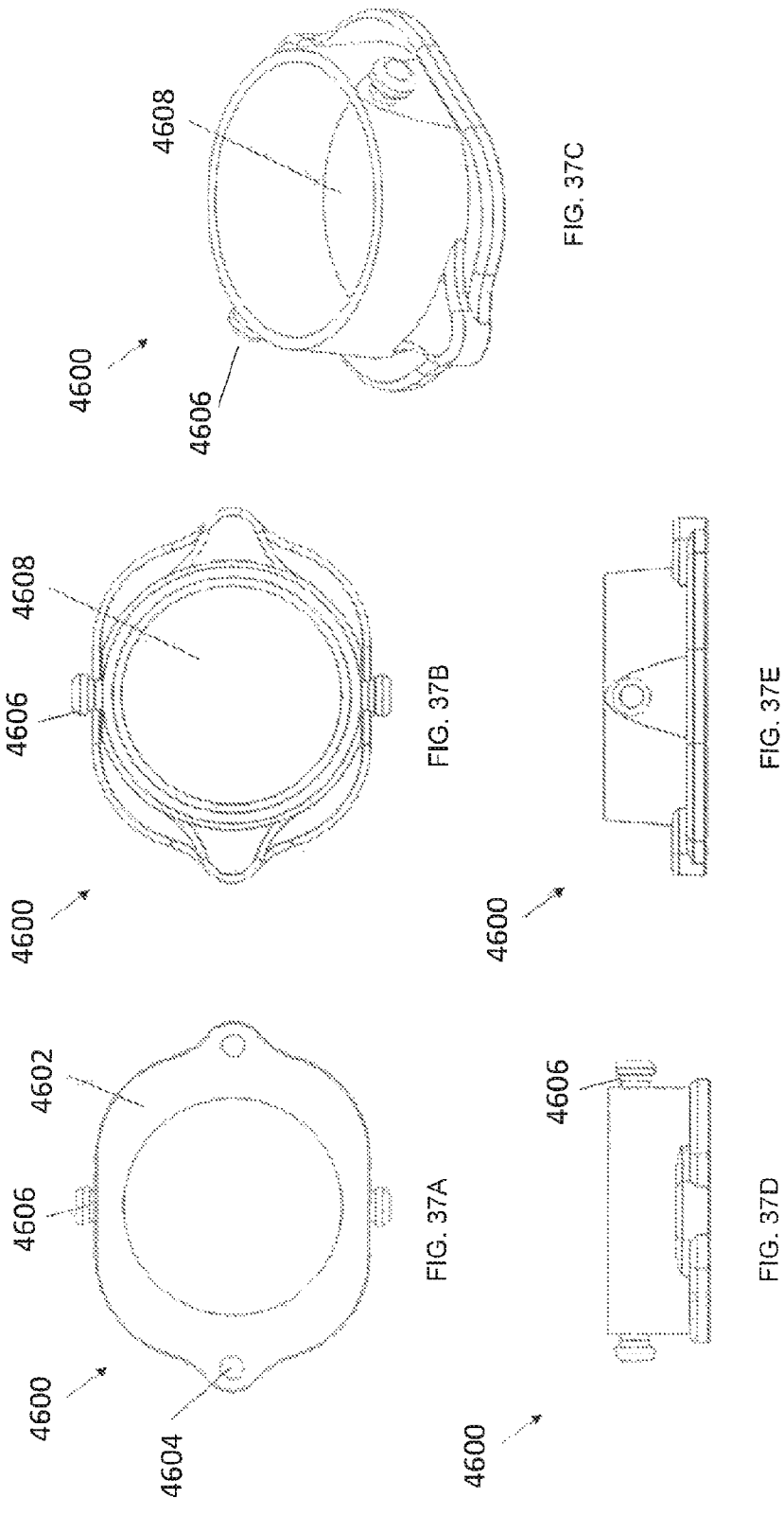
FIGS. 37A-37E illustrate various views of an embodiment of a bottom portion of a coupling pad holder.

FIGS. 37A-46E show various views of an embodiment of a bottom portion 4600 of a coupling pad holder. FIG. 37A shows a top view of the bottom portion 4600. A top surface 4602 of the bottom portion 4600 is configured to interact with a bottom surface 4506 of the top portion 4500. An attachment mechanism, such as magnets 4604 are configured to interact with a corresponding attachment mechanism on the bottom surface of the top portion of the holder. Other attachment mechanisms, such as side tabs or those described elsewhere herein, are also possible. Protrusions or knobs 4606 are provided on either side of the bottom portion 4600. These knobs 4606 can be configured to hold or attach to a strap that is used to secure the coupling pad holder to an ultrasound transducer device. FIG. 37B shows a bottom view of the bottom portion 4600. Opening 4608 is configured to receive an ultrasound transducer portion (e.g., head) of an ultrasound device (e.g., ultrasound wand). FIG. 37C shows a bottom perspective view of the bottom portion 4600. The opening 4608 is shown as round, but other configurations (ovular, square, rectangular) are also possible. FIGS. 37D and 37E show front and side views, respectively, of the bottom portion.

Figure 38:
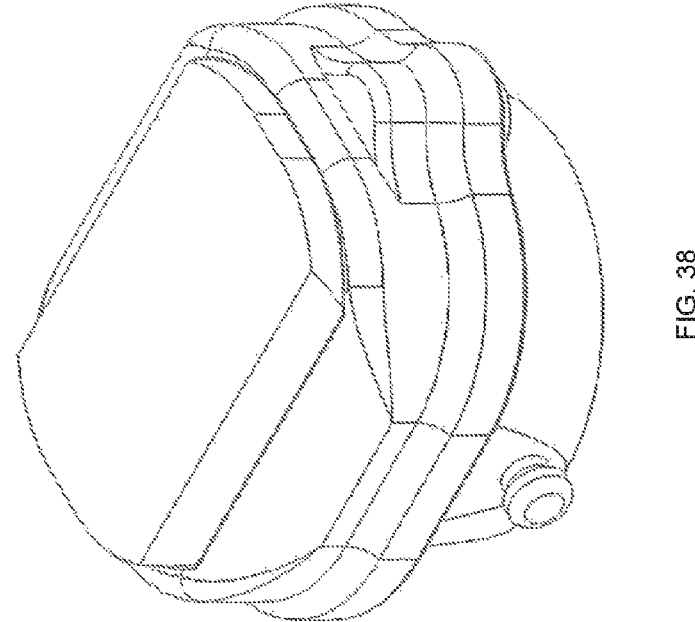
FIG. 38 depicts an embodiment of an assembled coupling pad component.

FIG. 38 depicts top perspective view of an embodiment of a coupling pad component 4700 comprising a coupling pad 4400 positioned within assembled coupling pad holder 4702 comprising top and bottom portions. A top surface of the coupling pad, including a portion of chamfered edges 4402 is shown protruding through the opening 4502 in the top portion of the coupling pad holder. As described above, the coupling pad component comprises rounded edges and surfaces providing comfort to the user during use.

To assemble the coupling pad component, a user can place a top surface of a coupling pad through a top opening of a top portion of the coupling pad holder. The bottom surface of the coupling pad should be flush with the bottom edge of the top portion of the holder. This positioning can ensure good contact with the ultrasound transducer. The user can then connect the bottom portion of the holder to the top portion using an attachment mechanism, such as magnets shown in FIGS. 36B and 37A. In some embodiments, the user can then place an ultrasound conductive material, such as ultrasound gel through the bottom opening of the bottom holder onto the bottom surface of the coupling pad. The user can then insert an ultrasound transducer portion of an ultrasound device through the bottom opening of the bottom holder so that it contacts a bottom surface of the coupling pad. A strap attached to knobs on the bottom portion of the holder can be used to secure the coupling pad component to the ultrasound device.

Figure 39:
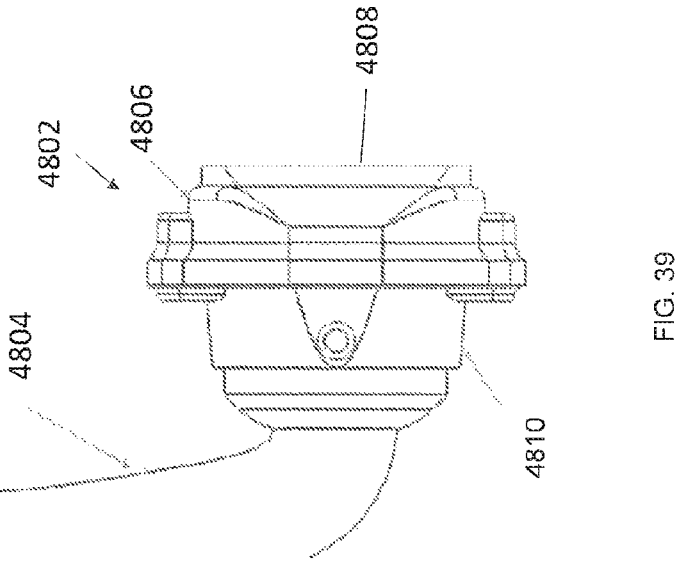
FIG. 39 shows an embodiment of a coupling pad component attached to an ultrasound transducer device.

FIG. 39 illustrates an embodiment of an assembled coupling pad component 4802, including top portion 4806 and bottom portion 4810 of the holder and coupling pad 4808, attached to an ultrasound transducer device 4804.

A method of using a device as described herein follows. A user ensures the device is sufficiently charged to initiate a therapy session. The user can remove a coupling pad portion from its packaging and attach it to the head portion of the device. Attaching can be performed using magnets, a threaded connection, or as otherwise described herein. Once the device is assembled, the user holds the handle portion and positions the device so the coupling pad is in contact with her introitus (vaginal opening). The user then activates the device. Activating the device can comprise pressing down a button on the handle portion. In some embodiments, the button is held down to turn the device on or off. For example, the button can be depressed for about 1, 2, 3, or more seconds. During treatment pressing the same button can pause and resume treatment. Pressing the button can activate the device for the desired duration and at the desired settings.

In some embodiments, the ultrasound settings comprise a frequency of about 1 MHz. The intensity can be about 1.7 W/cm$^2$. The duty cycle can be about 50%. In some embodiments, the frequency can be 0.5 MHz-3 MHz, 1.5 MHz, 2 MHz, or 2.5 MHz. In some embodiments, the intensity can be bout 1-2.5 W/cm$^2$, 1 W/cm$^2$, 1.5 W/cm$^2$, 2 W/cm$^2$, 2.2 W/cm$^2$, or 2.5 W/cm$^2$. In some embodiments, the duty cycle can be between about 20%-80%, about 30%, about 40%, about 60%, about 70%, about 80%, about 90%, or about 100%.

In some embodiments, the device is used daily for eight minutes per day. As described herein, in other embodiments, the device can be used multiple times a day, weekly, bi-weekly, monthly, etc. The device can be used for different durations. For example, durations of 5, 6, 7, 9, 10, or 10-15 minutes are contemplated.

Two acute and one chronic IRB-approved clinical studies have been conducted at Stanford University Hospital. The goal of the first study (Acute Study #1) was to determine therapy safety, as therapeutic ultrasound had never been used in this part of the body for this purpose with this patient population.

Safety was demonstrated by Acute Study #1. The results showed that the energy used may be too low and therefore attenuated before reaching the target depth of 3 cm to 6 cm. Hence, a second acute clinical study (Acute Study #2) was conducted at increased ultrasound intensities (See Table 6), still deemed to be safe based on numerical and benchtop temperature simulations (not shown). The data from this study showed a significant (3×) increase in vaginal tissue blood flow and temperature (about 2.5°) (data not shown), demonstrating the current device mechanism of action. Results from Acute Study #1 are partly shown in FIG. 9.

TABLE 6

| Summary of Ultrasound Settings in the clinical studies | | | | | |
|---|---|---|---|---|---|
| Trial | No. pts treated | Frequency | Intensity | Duty Cycle | Duration |
| Acute Study #1 | 10 | 1 MHz | 1.5 W/cm$^2$ | 50% | 8 min. |
| Acute Study #2 | 9 | 1 MHz | 2.2 W/cm$^2$ | 100% | 8 min. |
| Chronic Study | 7 | 1 MHz | 1.5 W/cm$^2$ | 50% | 8 min., daily |
| | 8 to 20 | 1 MHz | 2.0 W/cm$^2$ | 50% | 8 min., daily |

Patient symptoms, as recorded by surveys, also showed improvements in both Acute Study #1 and #2. 68% of participants reported an increased level of vulvovaginal lubrication after treatment for 24 hours or more after the study visit.

Figure 40A:
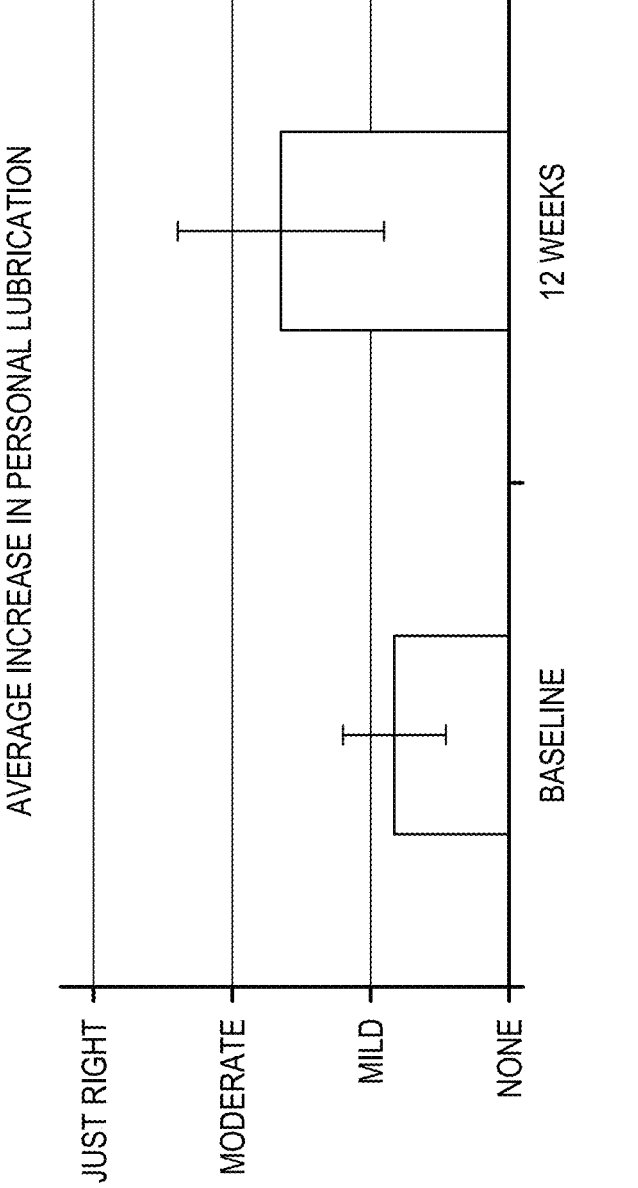
FIGS. 40A-40D are bar graphs showing results from clinical trials showing the effectiveness of an ultrasound device as described herein.
Figure 40B:
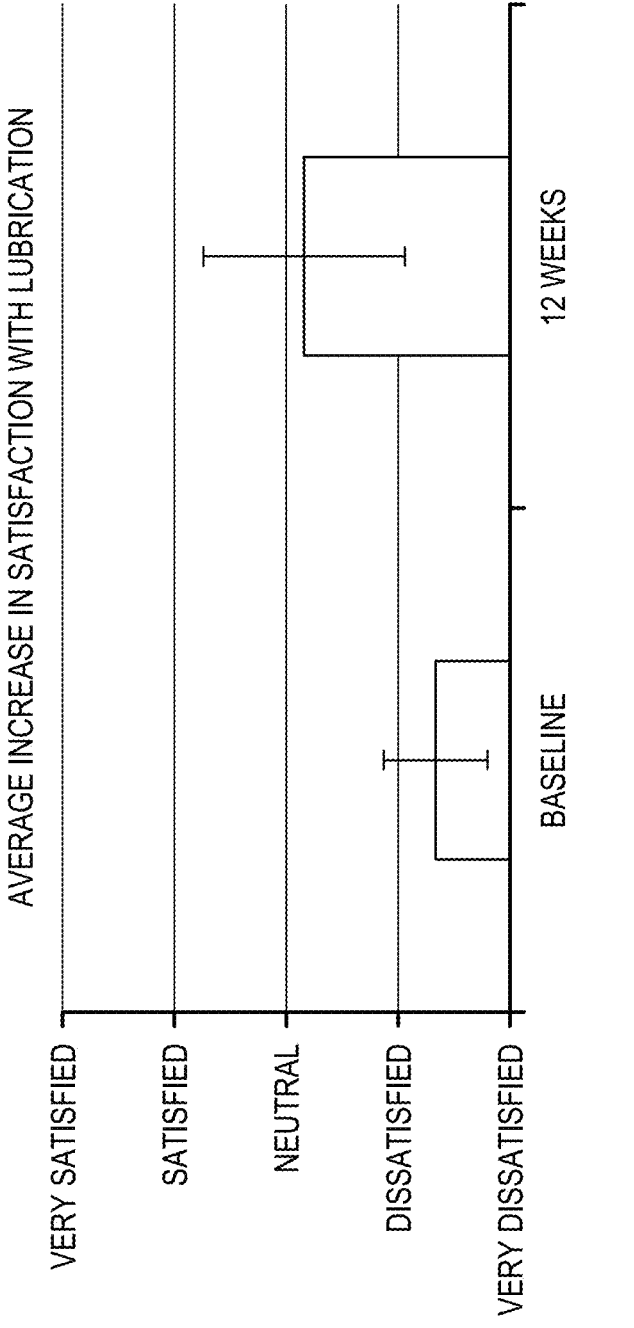
Figure 40C:
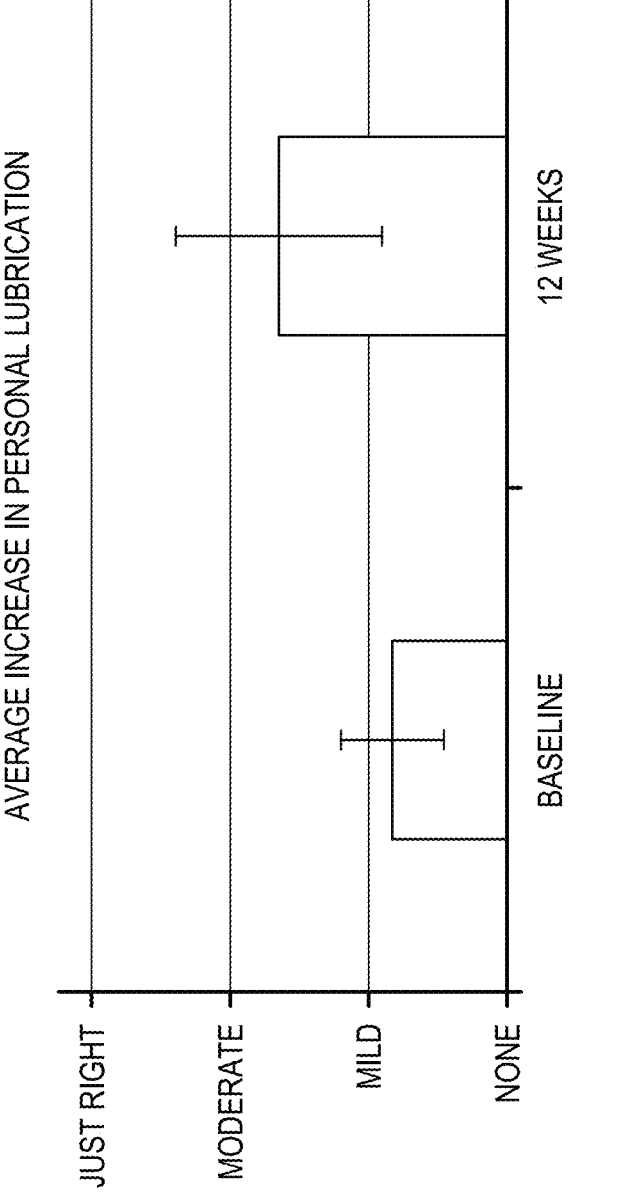
Figure 40D:
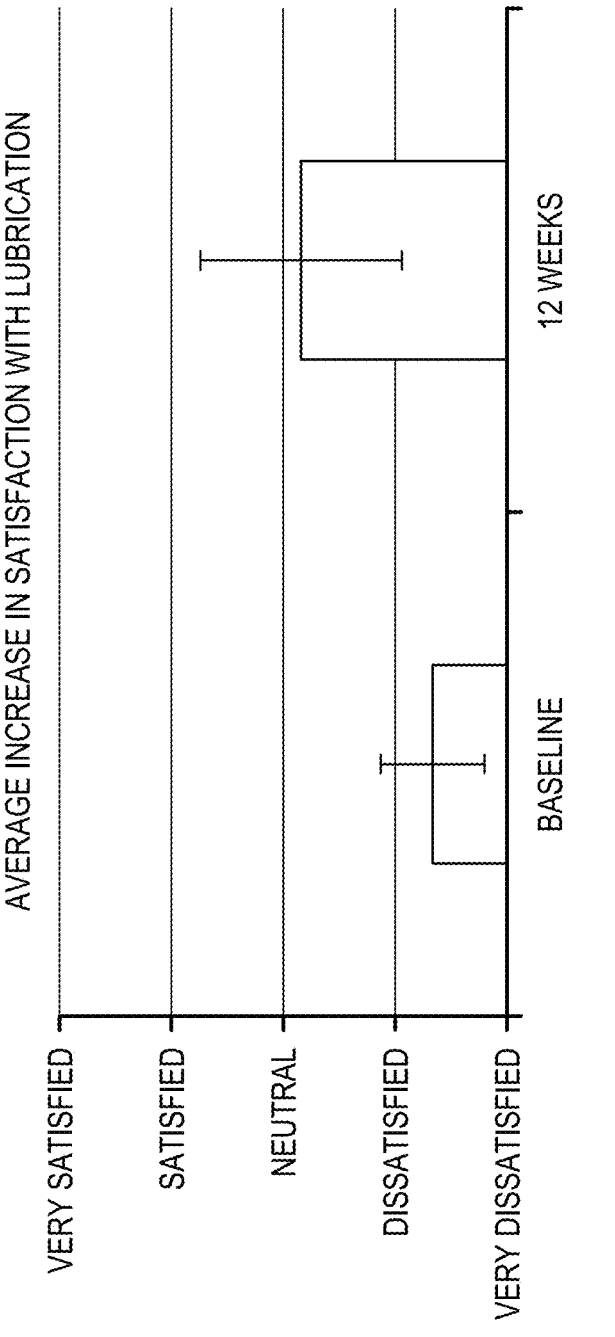

To determine if repeated use of the current ultrasound therapy will lead to improvements in VVA, a third clinical study (Chronic Study, Table 6) was conducted. In this investigation, participants use an ultrasound treatment prototype at home, daily for 8 minutes a day. For this study, the Ultrasound Settings were modified slightly from Acute Study #2. Duty cycle was reduced from 100% to 50%. Intensity was decreased to 1.5 W/cm$^2$ for the first seven patients. After it was clear this energy level was well tolerated (no complaints or adverse events), the dose was escalated to 2.0 W/cm$^2$ for all subsequent pts. FIGS. 40A-40D show results from this study. The error bars in the tables represent the standard deviation. FIG. 40A shows the mean change in temperature after 8 minutes of ultrasound therapy. FIG. 40B depicts an average decrease in vaginal dryness for patients who have completed the study to date. As shown, the patients' generally report vaginal dryness has clearly decreased over 12 weeks. FIG. 40C shows an average increase in personal lubrication for patients who have completed the study to date. As shown, patients generally report an increase in personal lubrication after 12 weeks. FIG. 40D depicts an average increase in satisfaction with lubrication for patients who have completed the study to date. As shown, patients are generally more satisfied with their lubrication after 12 weeks of therapy.

FIGS. 41A-42C show another embodiment of an ultrasound device comprising a main device and a coupling component. Unless other stated, the device 4110 comprises any combination of features described with respect to other embodiments described herein.

In some embodiments, the device 4110 can utilize ultrasound parameters as previously described. The ultrasound settings comprise a frequency of about 1 MHz. The average intensity can be about 1.7 W/cm$^2$. The duty cycle can be about 50%. In some embodiments, the frequency can be 0.5 MHz-3 MHz, 1.5 MHz, 2 MHz, or 2.5 MHz. In some embodiments, the intensity can be bout 1-2.5 W/cm$^2$, 1 W/cm$^2$, 1.5 W/cm$^2$, 2 W/cm$^2$, 2.2 W/cm$^2$, or 2.5 W/cm$^2$. In some embodiments, the duty cycle can be between about 20%-80%, about 30%, about 40%, about 60%, about 70%, about 80%, about 90%, or about 100%. Feasibility studies were performed to determine optimal settings that produced the proper. The combination of ultrasound parameters disclosed herein can achieve the desired result while minimizing risk. For example, the parameters can provide the appropriate temperature rise while avoiding an overly high range.

Figure 41A:
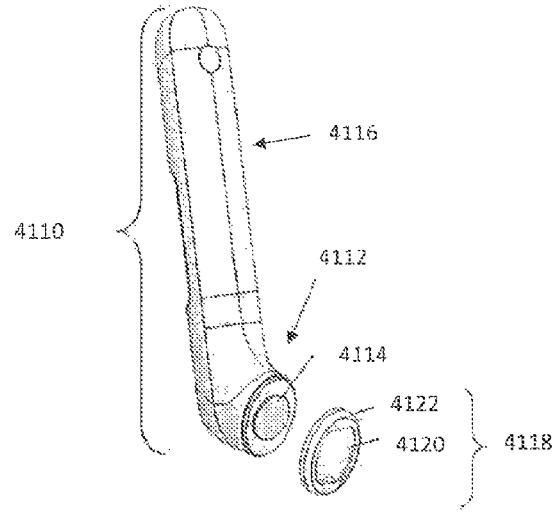
FIGS. 41A-41B show another embodiment of an ultrasound device.
Figure 41B:
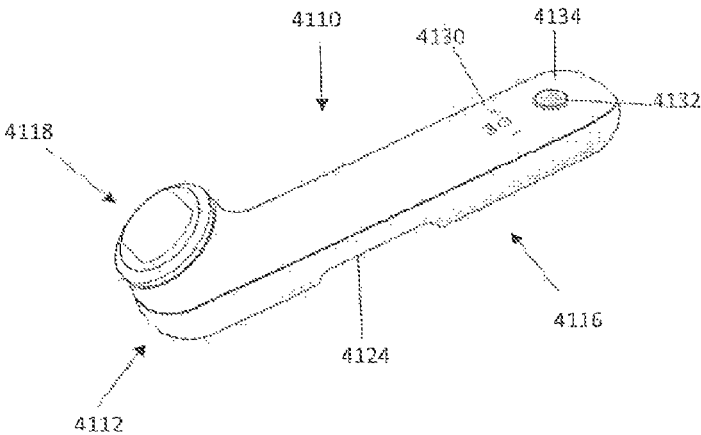

FIG. 41B shows a perspective view of the device 4110 without the coupling component attached. The main device 4110 comprises a handle portion 4116 and a head portion 4112. In some embodiments, the head portion 4112 of the device 4110 comprises an ultrasound transducer 4114. The ultrasound transducer can be a flat, disc-type transducer. Other configurations (e.g., curved) are also possible. In some embodiments, the ultrasound transducer is a ceramic piezo-electric crystal. Other transducers are also possible. The transducer can have a diameter of about 15-25 mm, about 15 mm, about 20 mm, or about 25 mm. Other transducer sizes are also contemplated. The effective radiating area (Aer) of the transducer can be about 2 cm$^2$. Other areas are also possible (e.g., 2-12 cm$^2$, 2-8 cm$^2$, 2-6 cm$^2$, 2-4 cm$^2$, or about 3 cm$^2$). In some embodiments, the Aer is about 2.0 cm$^2$. The beam non-uniformity ratio (Rbn) of the transducer can be about 7:1. In some embodiments, the natural focal length is about 30-100 mm, about 30-80 mm, about 40-70 mm, about 45-65 mm, about 45-55 mm, or about 50 mm. In some embodiments, the device comprises a temperature sensor (e.g., thermistor) on or near the ultrasound transducer.

The head portion 4112 also comprises attachment means for connecting to the coupling pad portion. The attachment means can comprise magnets on the head portion 4112 configured to engage with magnets on the coupling pad portion. Magnet attachment means can be easy to use and easy to clean as they may have a low profile. Other attachment means (e.g., hook and loop, snaps, straps, etc.) are also possible. For example, in some embodiments, the attachment means comprises a threaded connection between the head portion and the coupling pad portion, as described elsewhere herein.

The main device can comprise plastic (e.g., Polyethylene, Polypropylene, Polystyrene, Polyester, Polycarbonate, Polyvinyl Chloride, Polymethylmethacrylate (PMMA), Polyetheretherketone (PEEK), etc.) with or without a silicone overmold, over certain portions of the handle portion for ease and comfort during use.

The device can have a length of about 200-300 mm, 225-275 mm, about 200 mm, 210 mm, 220 mm, 230 mm, 240, mm, or 250 mm. The device can have a width of about 20-60 mm, 30-40 mm, or about 37 mm. The device handle can have a thickness of about 20-60 mm, 30-40 mm or about 33 mm.

The handle portion can comprise a cutout 4116 that is designed to aid in a user's grip of the device. User testing has shown that this cutout greatly improves user ease in holding the device and positioning it properly.

The handle can comprise one or more indicators to indicate at least one of: treatment in progress, pause, and disconnected coupling component. In some embodiments, a plurality of LEDs (e.g., arranged in a ring shape) are configured to indicate the progression of a treatment. For example, at the beginning of the treatment, all the LEDS are on. One by one, as the treatment progresses, the LEDs turn off to indicate that the treatment is progressing and the state of completion. A control button can be configured to start treatment, pause treatment, and turn off the device. In some embodiments, a short press can cause the device to pause, while a long press can cause the device to shut off. In some embodiments, the ring of indicator LEDs are arranged around the control button.

The device can comprise a data port configured to allow updating or fixing of software.

Figure 41C:
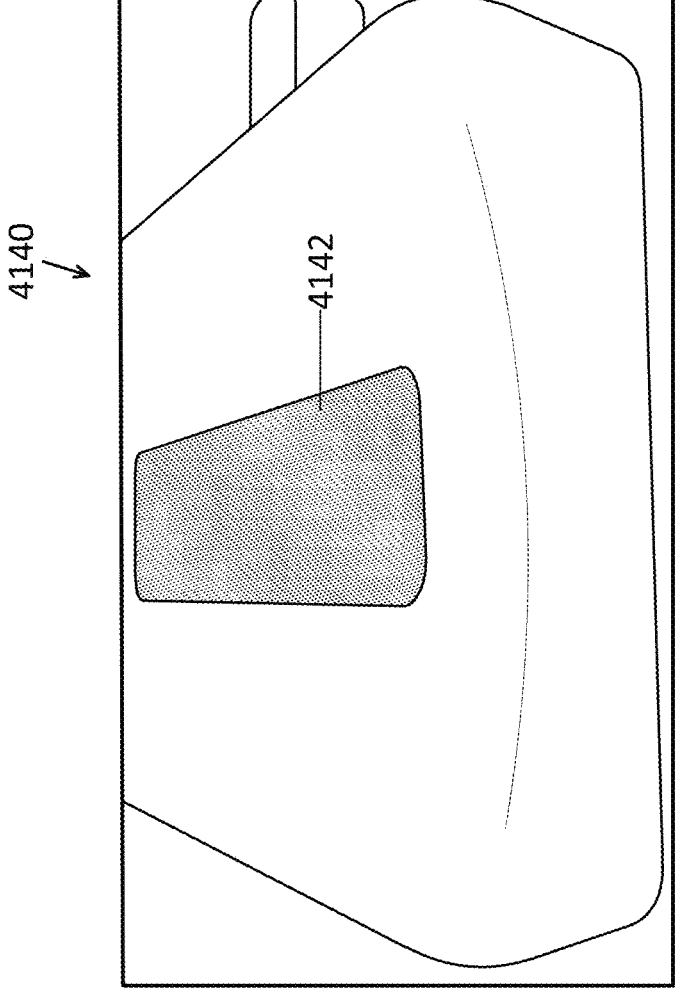
FIG. 41C shows an embodiment of a charger for an ultrasound device.

FIG. 41C shows an embodiment of a charger 4140 that can be used to recharge the device. The charger can be attached to a AC/DC Wall Mount Adapter and plugged into a standard outlet. The charger can be an inductive charger. The device can be configured to rest in the channel 4142 in the middle of the device. The charger can have a generally smooth profile, which can aid in keeping the charger clean and not accumulating dirt or dust.

In some embodiments, the device can be configured to restrict use while charging. This feature can advantageously prevent a user from using the device while it is connected to an outlet, adding an extra level of safety to the device.

In some embodiments, the device controller is configured to monitor voltage, current, and phase between the voltage and current to determine whether the device is coupled to the tissue correctly. If the device determines that it is improperly coupled, it can throw an error and/or shut off the device. The device can also use this monitoring to make sure these properties are not out of range and that the device is not delivering too much power.

In some embodiments, the device comprises a lockout feature to ensure that users cannot use the device for a lockout duration after treatment to confirm people are not over-treating themselves. The lockout duration can correspond to a period of time after a treatment dose (e.g., when the device last delivered an ultrasound therapy) in which the device will not deliver another treatment dose. In some examples, the lockout duration may from about 4 to 24 hours (e.g., 4, 6, 8, 9, 10, 20 or 24 hours) after treatment.

Figures 42A, 42B, 42C:
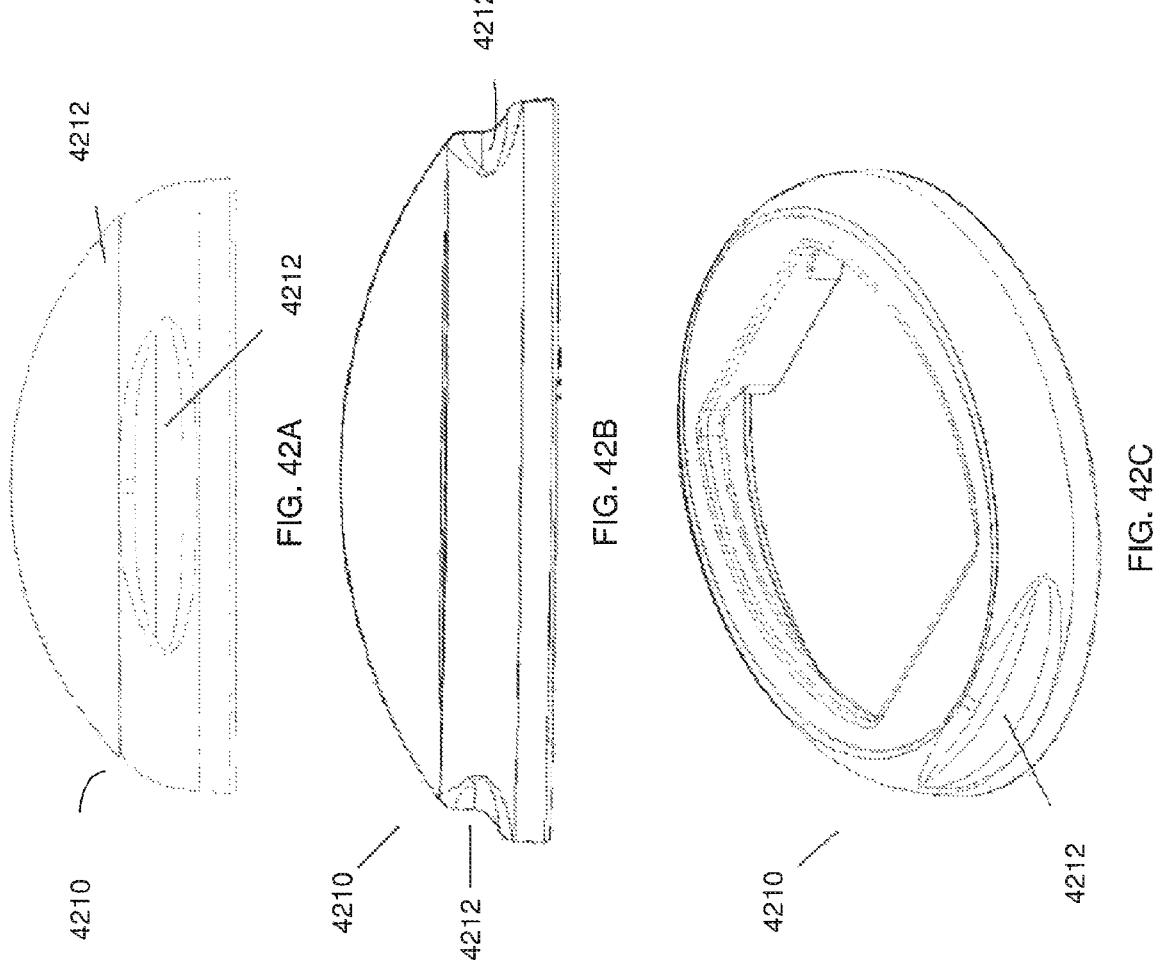
FIGS. 42A-42C show various views of an embodiment of a coupling component.

FIGS. 42A, 42B, and 42C show front, side, and perspective views, respectively, of a coupling pad 4210. The coupling pad can have a convex, rounded, dome shape. The coupling pad can have a height (above support ring) of about 2-8 mm, about 3-7 mm, about 5-7 mm, or about 6.5 mm. As described elsewhere herein, this configuration of the coupling pad can be most comfortable and intuitive to use for patients. The shape of the coupling pad can allow the user to self-navigate the device to the proper position near the vagina, at the introitus. In some embodiments, the user navigates to the proper positioning based solely on touch; thus, intuitive positioning can be useful for ensuring proper device use. Other coupling pad configurations are also possible (e.g., taller or shorter dome, central nub, flat top dome, ridge, etc.) The support ring can have depressions 4212 on the front and back sides. The depressions can be used to provide ease of handling the coupling pads. A user can place their fingers within the depressions to grip the coupling pad.

The coupling pad component can comprise a support ring 4212. The ring comprises an ovular shape. Other shapes (e.g., circular, rectangular, square, etc.) are also contemplated. A length of the support ring can be about 30-60 mm, about 40-50 mm, about 45 mm, about 46 mm, or about 47 mm. In some embodiments, the length of the support ring is about 46.6 mm. A width of the support ring can be about 20-50 mm, about 30-40 mm, about 35 mm, about 36 mm, or about 37 mm. In some embodiments, the width of the support ring is about 36 mm. The opening in support ring is filled in by coupling pad material and, thus, represents the area of the coupling pad that will engage the transducer face. Other support ring designs may comprise plates or other features obscuring a portion of window. By not having such a feature, better coupling between the transducer and coupling pad is enabled. Additionally, not having such a feature improves manufacturability as injection molding can be used and material cost decreases. In some embodiments, not having a backing plate or other similar feature in the support ring can cause the coupling pad to fall out of the support ring if handled too often or too rigorously. In single use embodiments, this can be a nice feature to prevent re-use of the coupling pad. The support ring can comprise a plastic material (e.g., HDPE, Polyethylene, Polypropylene, Polystyrene, Polyester, Polycarbonate, Polyvinyl Chloride, Polymethylmethacrylate (PMMA), Polyetheretherketone (PEEK), etc.).

The bottom surface of the support ring can be configured to mate with the head portion of the main device. The bottom surface comprises attachment means, such as magnets, configured to engage attachment means of the head portion of the main device. As noted above, other attachment means, such as a threaded connection, are also possible.

The bottom surface of the coupling pad is that area that will interface with the ultrasound transducer. In some embodiments, a surface area of the coupling pad that interfaces with the ultrasound transducer is about 3-7 cm$^2$, 4-6 cm$^2$, 5 cm$^2$. In some embodiments, the surface area is about 4.9 cm$^2$. In some embodiments, the coupling pad material comprises a material that can be configured to conform to the tissue (e.g., the area exterior to the vagina, the vulva and introitus). In some embodiments a hydrogel is used. The hydrogel can comprise a combination of any one of agarose, water, Cetylpyridinium chloride (CPC), and glycerin. In some embodiments, the coupling pad comprises about 2% agarose, about 20% glycerin, about 0.5% CPC, and the rest water. Other concentrations are also possible. For example, the coupling pad can comprise about 2-10% agarose. The coupling pad can comprise about 10-25% glycerin. In some embodiments, the coupling pad comprises about 1-5% CPC.

As described elsewhere herein, the coupling component can be disposable. In some embodiments, the coupling or disposable component is intended to be disposed of after each treatment site, and a new component is to be used with each treatment. In other embodiments, a coupling component can be reused between treatments.

Figure 43A:
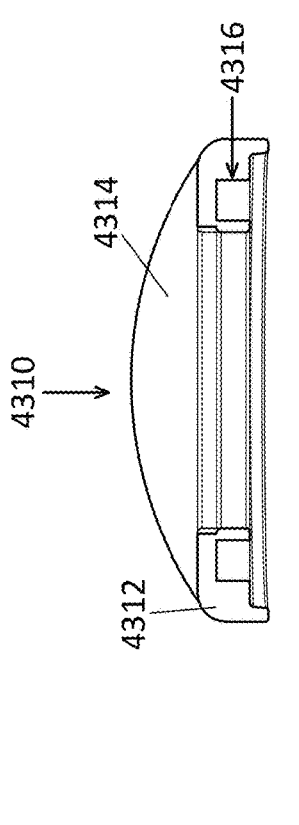
FIGS. 43A-43C depict embodiments of metallic components in the coupling component and the main device.
Figure 43B:
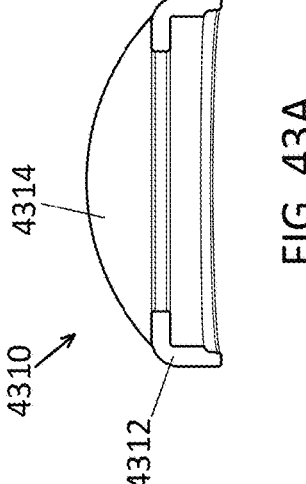
Figure 43C:
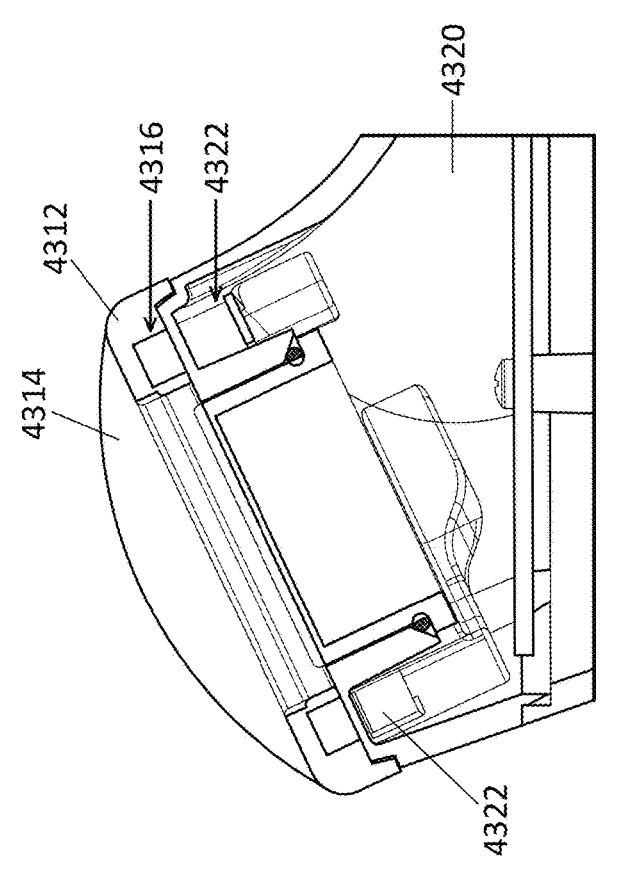

A magnetic connection between the coupling pad and main device achieves a secure mechanical connection (e.g., defined as a connection force of about 200-600 grams or 300-500 grams) between the transducer face of the main device and the face of the coupling pad, with minimal effort required from the user. This can be especially beneficial for users of impaired, deteriorated or otherwise limited dexterity (e.g. those having arthritis, etc.). A secure connection between the coupling pad and the main device can be critical in ensuring continuous and safe ultrasound communication to the tissue via no air gaps or bubbles. FIGS. 43A and 43B show front and side views, respectively, of an embodiment of a disposable component 4310. As shown, the disposable component 4310 comprises a support ring 4312 and a coupling pad 4314. One or more metallic components 4316 are positioned within the support ring 4312. As shown in FIGS. 43A-C, the metallic components 4316 are flush with a bottom surface of the disposable component at the interface of the coupling pad and main device (FIG. 43C). In some embodiments, the metallic components are not flush with the bottom surface of the disposable component at the interface of the coupling pad and main device, but are near enough to the bottom surface of the disposable component at the interface to form a strong magnetic connection. The magnetic connection between the disposable and reusable components is achieved via metallic components in the disposable component. The metallic components can comprise magnets or ferrous metals. In some embodiments, the metallic components are made from stainless steel to prevent corrosion. In other embodiments the metallic components are isolated from the environment to prevent corrosion during storage before use. Isolation can be accomplished by a thin layer coating the magnetic components. The thin layer can be a conformal layer forming hydrophilic or hydrophobic coatings. In some embodiments, the layer comprises Parylene. A thickness of the layer can be about 50 microns. Isolation can also be accomplished using methods such as insert molding the components into the Support Ring, itself. In some embodiments, the metallic components comprise low or medium-carbon steels, such as grades SAE 10xx, 11xx, 12xx or 15xx. Such materials can provide the advantage of a low Cost of Goods Sold (COGS) for the Disposable Component. For stainless steel the steel must be ferromagnetic such as cold-rolled 430 stainless.

FIG. 43C shows a section view of a coupling component 4310 attached to a reusable main device 4320. The coupling component 4310 comprises a coupling pad 4312 and a support ring 4312. The embodiment of FIG. 43 comprises two metallic components 4316 in support ring 4312. Fewer or more metallic components are also possible. For example, the coupling component can comprise 1, 3, 4, 5, 6, 7 or more metallic components. The main device 4320 comprises one or more sensors (e.g., a Hall effect magnetic field sensor or a magneto-resistive sensor) for detecting magnetic attachment of the metallic components 4316 of the coupling component 4310 to magnets 4322 in the main device 4320. Detecting magnetic attachment of the metallic components can, for example, comprise detecting the presence of metal the sensor's field. The magnets 4322 are positioned near an interface 4324 of the ultrasound transducer assembly and the coupling pad. The device 4320 will not activate ultrasound until confirmation of the attachment of the coupling component 4312 to device 4320, as determined by the deviation in the magnetic field of two magnets in the device 4320 when a metallic component in the coupling component is in close proximity to the mating surface, as measured by a Hall effect or magnetoresistive sensor.

FIGS. 44A-C illustrates a detailed view of an embodiment of the sensor assembly 4410 of the main device. As shown in FIG. 44B, the sensor assembly 4410 comprises a magnetoresistive sensor 4412 and magnets 4414 of the main device. The magnets 4414 are configured to interact with magnet 4413 of the coupling component (44A). A pair of magnets 4414 in the device, with opposite orientation of polarity, are on either side of a magnetoresistive sensor 4412. Attached to one side of the magnets is a metallic plate 4416 to form a continuous magnetic field between the magnets. The magnetoresistive sensor 4412 detects perturbations in this magnetic field when an additional metallic plate 4413 (or magnet or piece of metal) from a coupling component is within close proximity (e.g., during attachment).

As shown in FIG. 44C, the pair of magnets 4414, magnetoresistive sensor 4412 and metallic plate 4416 are affixed into a common assembly 4420, which locates the relative positions of these components. The common assembly 4420 can comprise a non-magnetic material such as an extruded non-magnetic polymer.

Figures 45A, 45B:
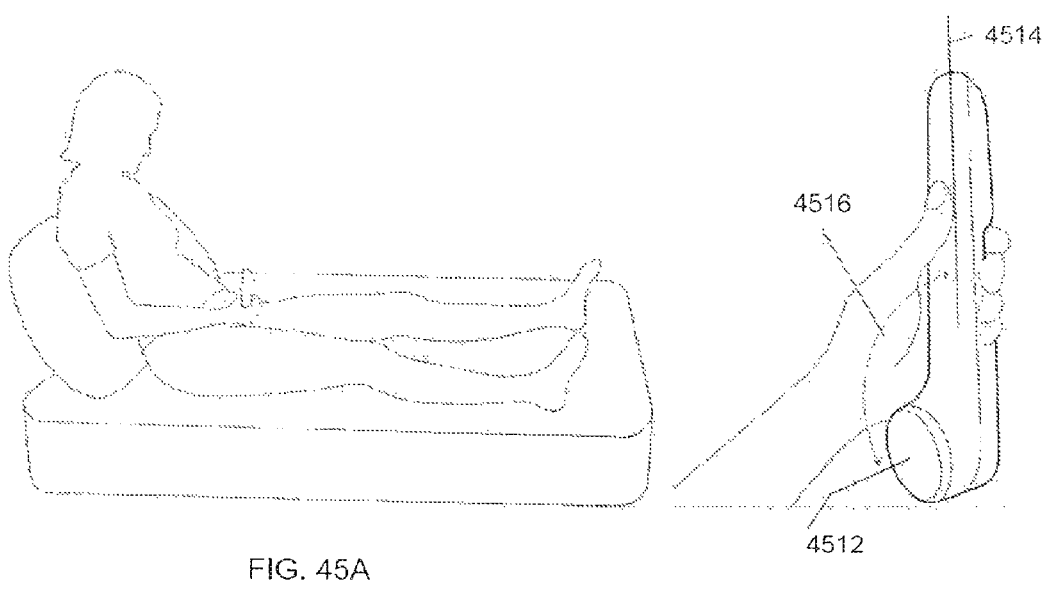
FIGS. 45A-45B show embodiments of features encouraging proper orientation of the device.

FIGS. 45A and B show a feature of the device which can enable and promote blind device placement and orientation from the user of the ultrasound beam along the vaginal canal (FIG. 45A). This feature is a specific angle 4516 of the ultrasound transducer face normal 4512 relative to the major axis 4514 of the device, which could be from about 90 to about 180 degrees, preferably about 115 degrees. This configuration can allow a user to blindly place the device as shown in FIG. 45A. In some embodiments, the user assumes a semi-reclined position and engages the coupling component of the device with the vulva. This feature can advantageously enable a user to properly position the device to effectively deliver the ultrasound treatment to the treatment site. In studies and interviews with user, this feature was found to be important in allowing a user to properly administer treatment.

Figure 46:
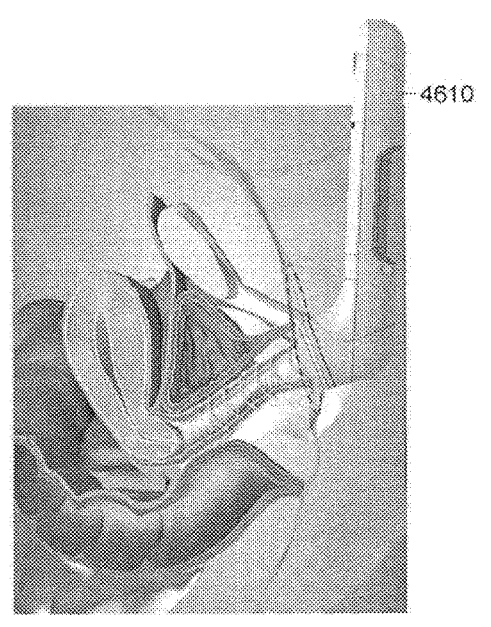
FIG. 46 depicts an embodiment of proper orientation of the device.

FIG. 46 depicts the proper orientation of the device 4610, which can be described as ultrasound coaxial to the axis of the vaginal canal. This proper positioning can be accomplished by the user without the benefit of direct visualization (due to the anatomical location) via markings or features along the long axis of the device in locations easily seen by the user, in combination with the angled distal end of the device. These features include visual markings such as labels or protrusions to indicate a desired vertical orientation of the long axis of the device. A user can use such markings to align the device to the desired orientation during use. For example, when the one or more visual markings or protrusions are aligned with one or more anatomical features of the female subject and the coupling pad is placed against the female subject's external genital tissue, the normal of the transducer face can be aligned within about 30 degrees of a longitudinal axis that extends through the female subjects vaginal canal. Proper orientation of the device can help ensure ultrasound conduction along the vaginal canal.

Component Packaging

In some embodiments, the component packaging comprises separate packaging for each disposable portion (e.g., support ring and coupling pad). The individualized packaging can hold the disposable portion in a liquid medium to keep the coupling pad hydrated as it may dry out if exposed to air. In some embodiments, the hydrating solution comprises a bacteriostatic solution (e.g., 0.9% benzyl alcohol solution). The support ring comprises plastic, in some embodiments, and will not degrade in the hydrating solution. The support ring can also provide a strong, rigid support for the coupling pad.

In some embodiments, the component packaging can comprise a blister pack formed to the shape of the coupling pad component. The shelf life can be about 1-3 years (e.g., 1 year, 2 years, 3 years). The blister pack can provide an easy to open component packaging sealed to lock in a hydrating solution. The blister pack can be rigid enough to support the shape of the coupling pad. The blister pack can comprise a medical grade plastic with a backing of foil or foil lined paper. A flexible backing can help with ease of opening for the user while still trapping the coupling pad moisture in the package.

In some embodiments, the coupling pad must be disinfected, but does not require sterilization. This feature can be promoted by an antimicrobial component (e.g., CPC) in the coupling component.

An embodiment of component packaging is provided by the Stephen Gould Corporation. The packaging consists of a thermoformed tray that holds 8 gel pads shown in FIG. 32, a box, and the easy to remove backing.

Figures 47A, 47B, 47C:
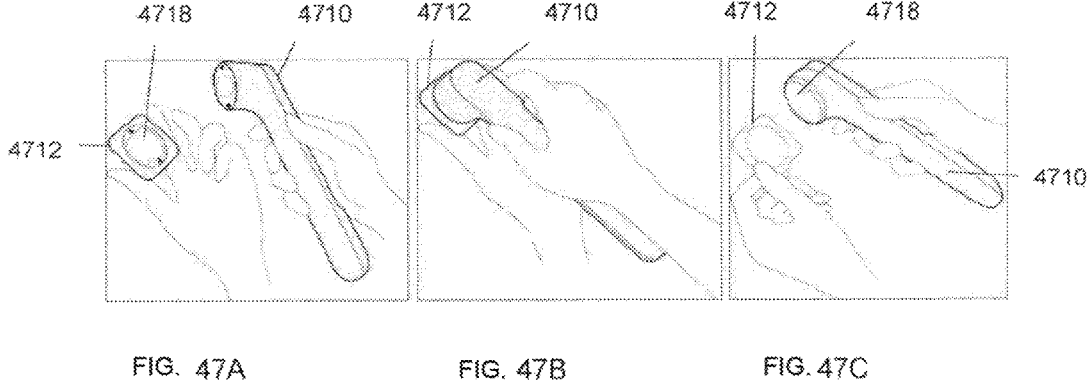
FIGS. 47A-47C show an embodiment of connecting an ultrasound device to a coupling component from the packaging.
Figure 48:
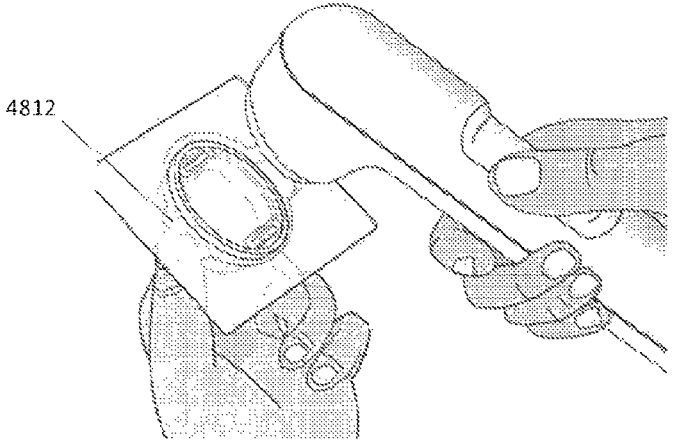
FIG. 48 shows an embodiment of coupling component packaging.

FIGS. 47A-C illustrate embodiments of a reusable main device 4710 and a disposable component 4712 with a coupling pad. FIG. 47A shows a reusable main device 4710 in a user's right hand and a package 4712 comprising a disposable component 4718 with a coupling pad in a user's left hand. The disposable component 4718 comprises metallic components such as magnets configured for attachment to magnets n the main device. As shown in FIG. 47B, the magnetic attachment scheme retains the bacteriostatic nature of the disposable component during the connection between the reusable component and the disposable component by not requiring manual manipulation of the disposable component by the user. A user can simply move the main device to the disposable component until the magnets sufficiently attract to attach the disposable component to the reusable main device. FIG. 47C shows the disposable component 4718 attached to the main device 4710 and empty packaging 4712 after removal of the disposable component 4718. FIG. 48 illustrates another view of a coupling component packaging 4812.

In some embodiments, the package comprises a decoupling feature such as wings surrounding the coupling component. The wings can comprise additional depressions in the packaging surrounding the coupling component. Applying pressure to the wings can allow air into the packaged coupling component and break any existing seal between the coupling component and the packaging, allowing a user to remove the disposable without damaging the gel and avoid touching the coupling component while removing it from the packaging. The wings or decoupling feature can comprise any one or more depressions surrounding the coupling component within the packaging.

Figure 49:
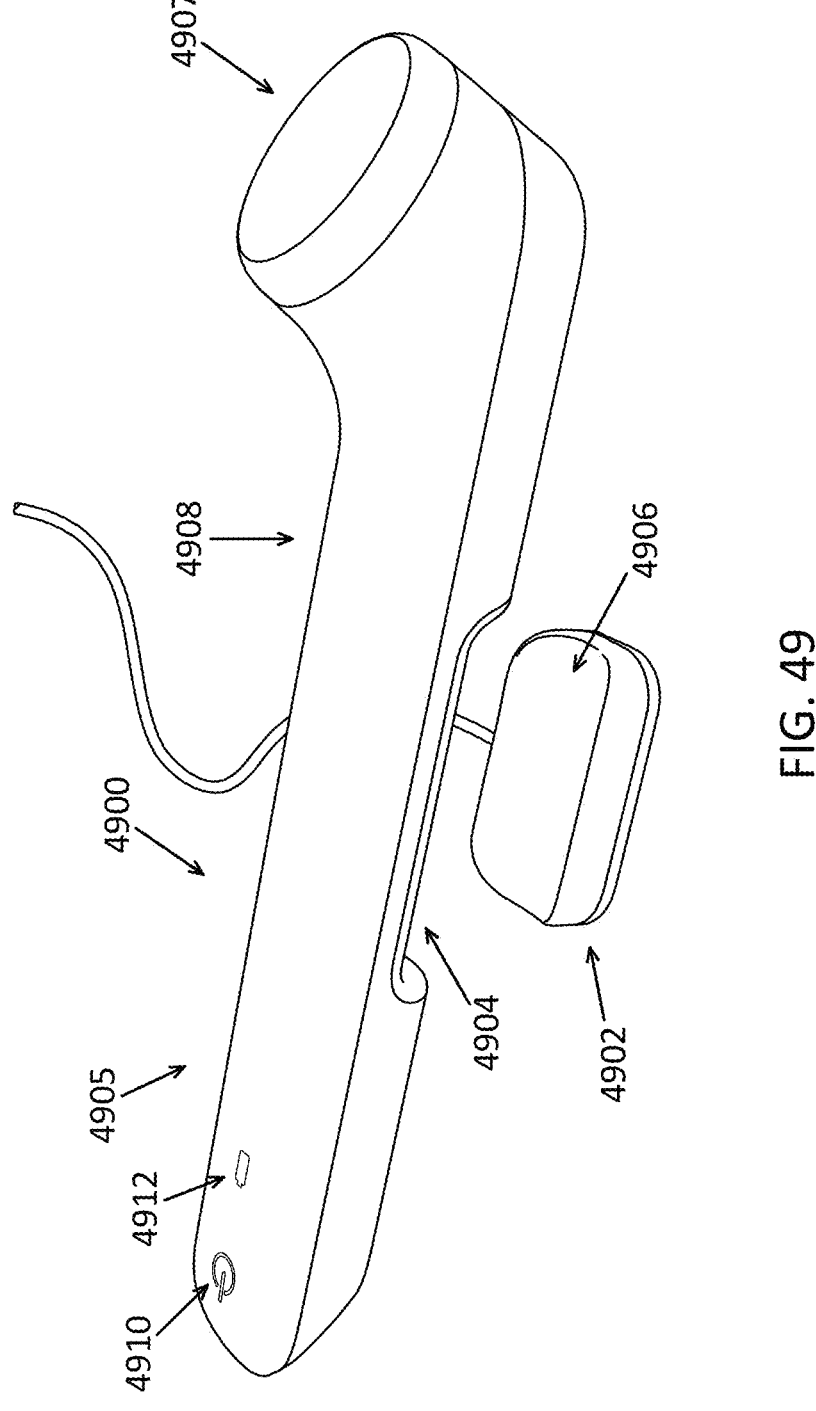
FIG. 49 shows an embodiment of an ultrasound device and inductive charger.

FIG. 49 illustrates an embodiment of an ultrasound device 4900, which includes an ultrasonic transducer component 4908 and coupling pad component 4907, and a corresponding charger 4902. In this example, one or more batteries of the device 4900 can be inductively charged by the charger 4902. The charger 4902 may be attached to an AC/DC Wall Mount Adapter and plugged into a standard outlet. The device 4900 and the charger 4902 can include corresponding features configured to mate during charging. For example, the device 4900 may include a recess 4904 adapted to accommodate at least a portion of the charger 4902. The recess 4904 can allow the device 4900 to rest on the charger 4902 during recharging. The charger 4902 may include a channel 4906, also referred to as a cradle, in which the device 4900 can rest. The housings of each of the charger 4902 and the device 4900 can have a generally smooth profile, which can make the charger 4902 and the device 4900 easy to clean. A handle portion 4905 of the transducer component 4908 can have can include a user interface including one or more control buttons, such as an on/off button (power button) 4910. In some cases, the handle 4905 includes a single control button. In some cases, the handle 4905 includes an indicator 4912 to indicate a state of the device 4900, such as whether the device is on or off. The indicator 4912 may include a visual indicator, such a light.

Figure 50:
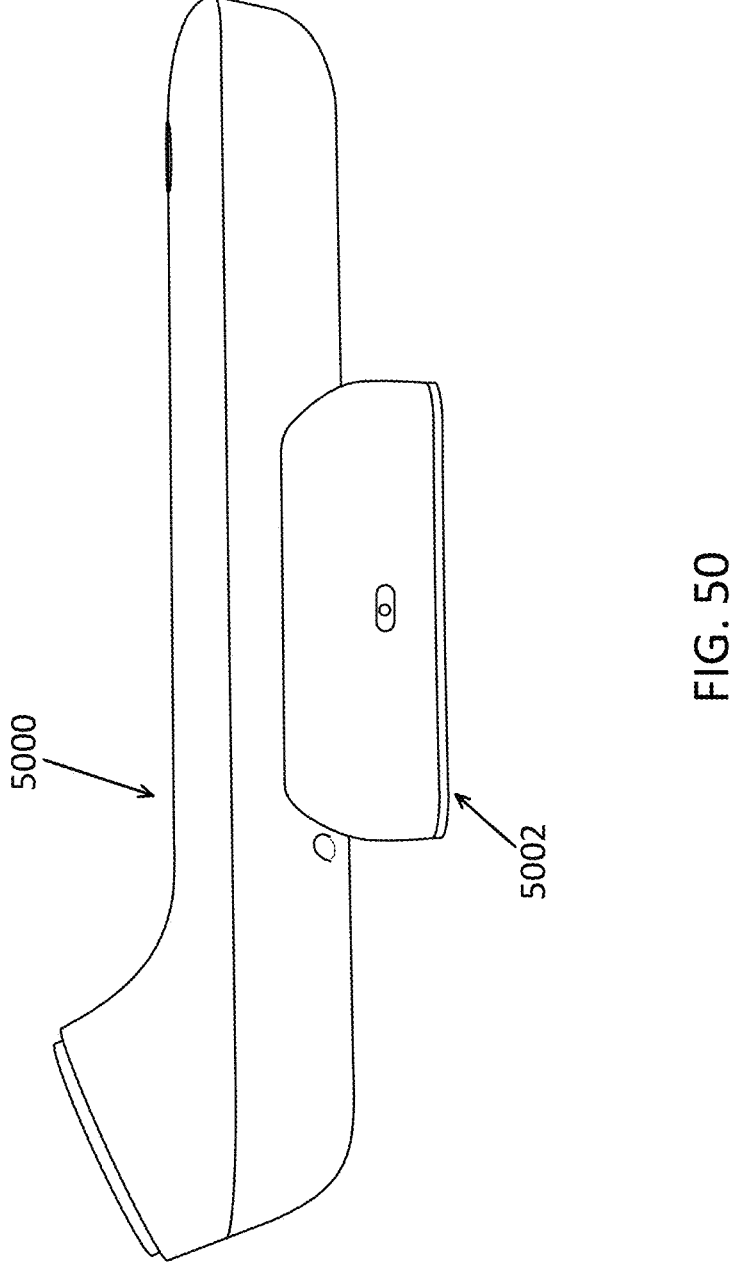
FIG. 50 shows an embodiment of an ultrasound device without a coupling pad, where the ultrasound device is supported within an inductive charger.

FIG. 50 illustrates an embodiment showing an ultrasound device 5000 positioned in a corresponding inductive charger 5002. As shown, the charger 5002 can be placed on a support surface, such as a table top, and serve as a supportive base for the device 5000 during charging.

Figure 51:
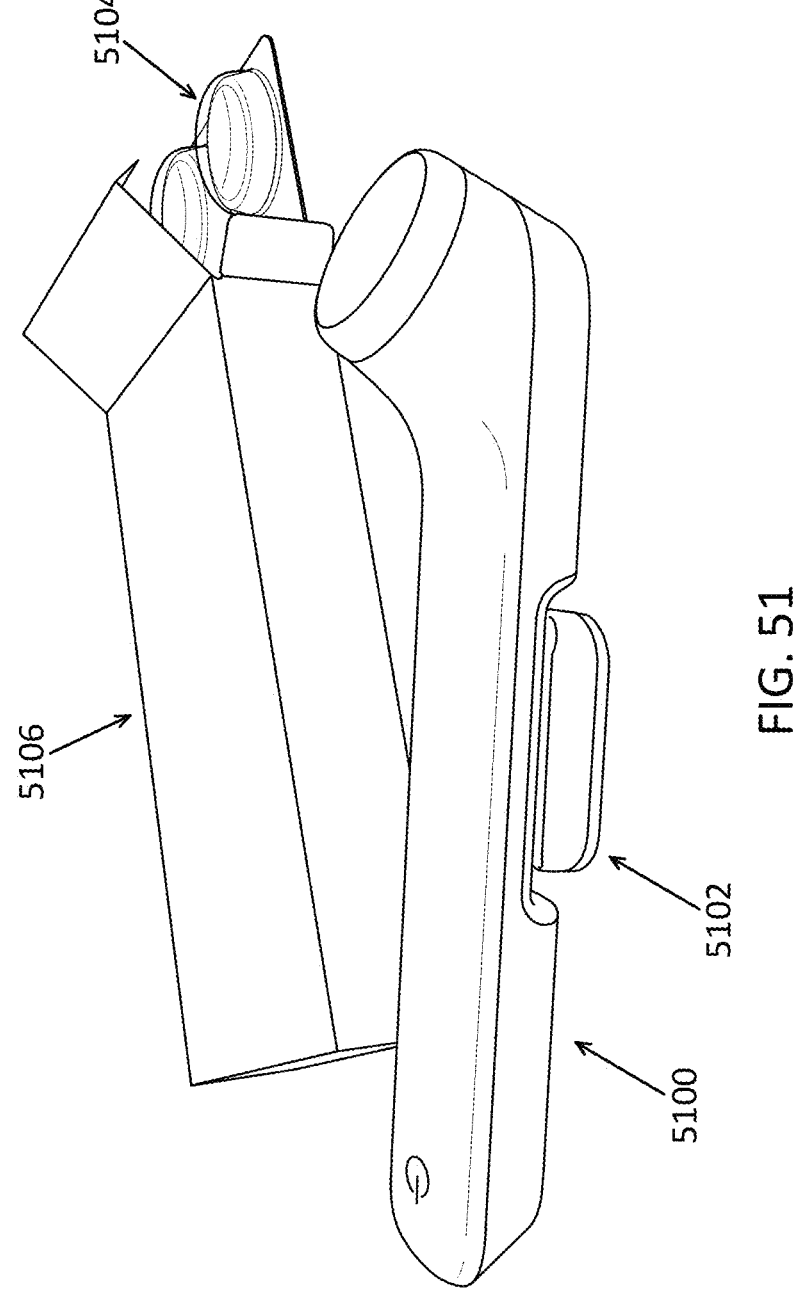
FIG. 51 shows an embodiment of an ultrasound device, inductive charger and packaged coupling pads.

FIG. 51 illustrates an embodiment showing an ultrasound device 5100, charger 5102, blister pack tray 5104 (holding multiple coupling pad components), and outer consumer packaging 5106 (e.g., box).

Several studies were conducted to demonstrate performance of the device. A first study demonstrated safety in ten women with a single-application of the ultrasonic therapy, as there were no device-related adverse events reported.

Figure 52B:
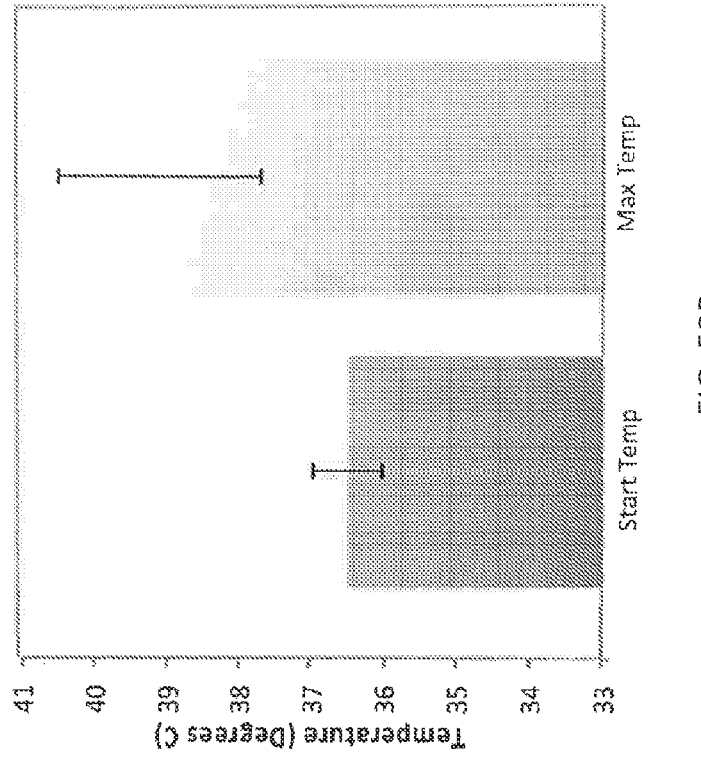
FIGS. 52A and 52B are bar graphs showing results from a second study showing changes in blood flow and temperature after using an ultrasound device described herein.
Figure 52A:
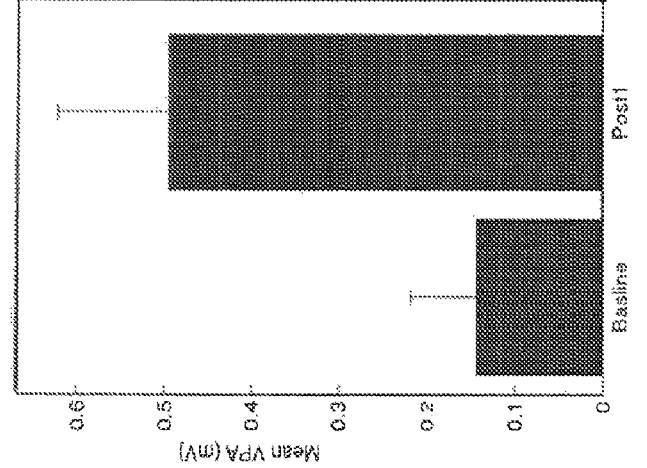

FIGS. 52A and 52B illustrate results from a second study measuring changes in blood flow and temperature change after a single dose of therapy in nine women. FIG. 52A shows the mean vaginal blood flow increase recorded with ultrasound application. Vaginal blood flow was measured through the use of a vaginal photoplethysmography probe (VPG), the gold standard of measurement in female arousal research, and temperature was measured with an intravaginally placed thermocouple. Vaginal Pulse Amplitude (VPA) was recorded from the VPG probe using a pre-ultrasound application reading as a baseline (Baseline) and a 10 minute post-ultrasound application (Post1). FIG. 52B shows average temperature increases recorded with ultrasound application. After 8 minutes of ultrasound therapy, a 300% increase in vaginal blood flow and a 2.6 degree Celsius (° C.) increase in temperature were observed. Patient-reported symptoms also improved, as 68% of women reported feeling more lubricated for 24 hours or more after a single treatment. Further, patient demand for a non-hormonal therapy to treat vaginal dryness was also validated, as more than 100 women indicated interest for the 19 clinical study appointments available.

Figure 53A:
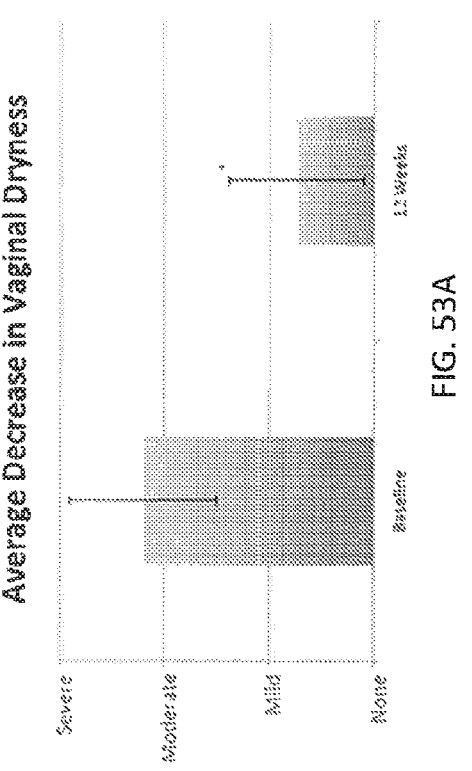
FIGS. 53A and 53B are bar graphs showing results from a clinical study showing results from repeated application of low-frequency ultrasound using an ultrasound device described herein.
Figure 53B:
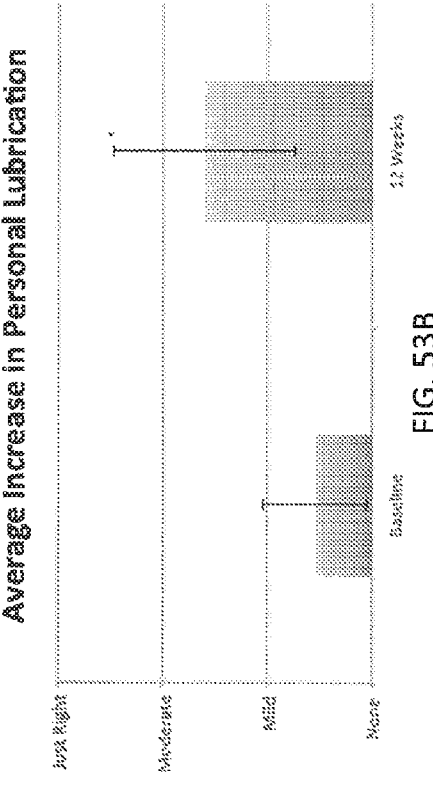

FIGS. 53A and 53B illustrate results from a third clinical study to investigate the effects of repeated application of low-frequency ultrasound. In the third study, twenty women used the ultrasound therapy at home daily for eight minutes per day over the course of three months. Patient-reported symptoms and gynecologist evaluated tissue responses via the Vaginal Health Index (VHI) and the Vaginal Maturation Index (VMI) were tracked across the study. Of the 20 women enrolled and 16 women completed the study. Two women withdrew from the study, one woman was withdrawn by the principal investigator due to a confounding medical condition, and one woman's device was broken when returned the end of the study. 81% of women reported drastic improvements in their vaginal dryness, demonstrating significant symptom relief. FIGS. 53A and 53B indicate measured improvement via a four-question Likert-scale survey instrument for dryness and personal lubrication, demonstrating significant change at 12 weeks compared to participants' baseline scores. Notably, these results are as good, or better, than the Phase III trial results of several FDA-approved products to treat vaginal dryness. Each of these on-the-market products are used by women today and thus demonstrate the efficacy bar required for approval and market adoption. This preliminary data suggest that the ultrasound therapies described herein can meet this bar. Further, survey results of the third clinical study indicated that nearly two thirds of the participants who completed the study indicated they would want to purchase the therapy device.

Figures 54, 55:
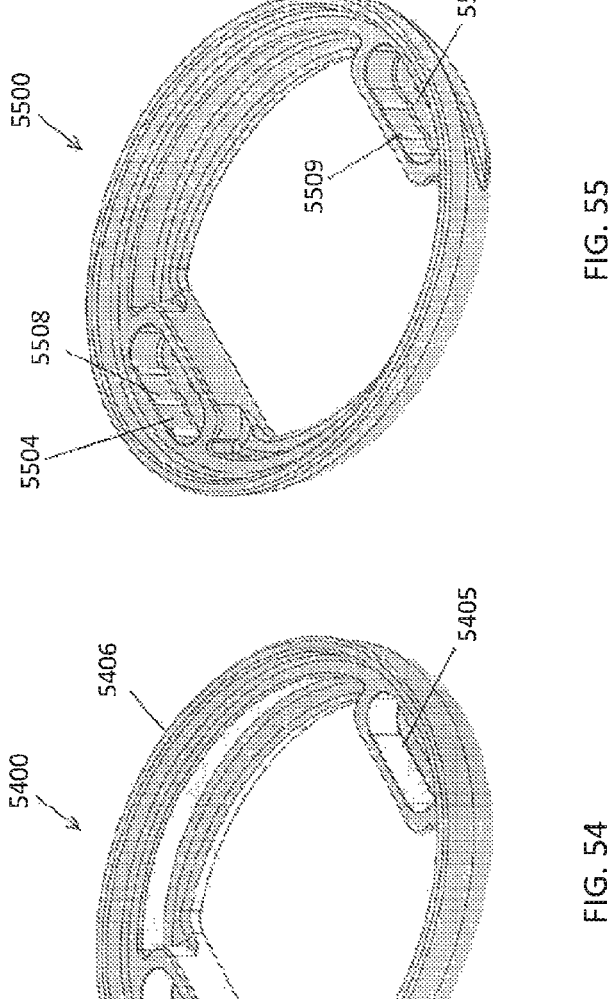
FIG. 54 show another embodiment of a support ring of a coupling pad component.
FIG. 55 show a further embodiment of a support ring of a coupling pad component.

FIG. 54 illustrates another embodiment of a support ring 5400 for providing structure to the coupling pad. As described above, the pad material may be molded into the support ring 5400. The support ring 5400 can have a similar general shape (e.g., oval cross-section) and dimensions as the support ring 3500 (FIGS. 26A-26D) described above. The support ring 5400 can include a cavities 5404 and 5405 for accepting metallic components for coupling the support ring 3500 with the reusable main component. An outer lip 5406 is configured to mate with a corresponding shape of the main component.

FIG. 55 illustrates another embodiment of a support ring 5500 similar to the support ring 5400 except that cavities 5504 and 5505 include one or more internal ribs 5508 and 5509. The internal ribs 5508 and 5509 may be configured to improve engagement with corresponding metallic components within the cavities 5504 and 5505 for compatibility with high-volume manufacturing.

Any of the devices described herein can include features configured to verify a disposable component (e.g., coupling pad component) for use with a reusable component (e.g., ultrasound transducer component). Such features can include communication technology to communicate data between the reusable component and the coupling pad component. In some examples, the communication is accomplished through optical reading technology (also referred to as an optical scanning technology). For example, the coupling pad component can include a barcode, quick response (QR) code reading or other optically readable code that a reader, as part of the ultrasound transducer component, can identify and use to validate the coupling pad component. Such verification capability can provide a number of advantages. As described herein, the coupling pad component is shaped, sized and has features to fit with a corresponding transducer assembly, for example, to provide optimal propagation of ultrasound energy (e.g., intensity and/or waveform) from the transducer assembly to the patient's tissues. Further, the shape, size and features of the coupling pad component may ensure proper placement/orientation of the coupling pad component with respect to the patient's anatomy and to provide proper propagation direction of the ultrasound energy (e.g., FIGS. 5 and 6), even with blind placement of the device. A coupling pad component that does not include the required shape, size and/or other features (e.g., counterfeit coupling pad component) may not allow the ultrasound energy to effectively transfer a therapeutic dose to the patient and/or may cause localized heating of tissue that may cause discomfort for the patient. Additionally, the electronic components of the transducer assembly are designed to operate with the coupling pad component without overheating under normal operating conditions. A "counterfeit" coupling pad component may cause the transducer assembly to overheat or otherwise function improperly.

Additionally, in some cases, it may be important to ensure that the coupling pad component is not reused. This is because in some embodiments the coupling pad component may include a material (e.g., gel or biocompatible fluid) having relatively high fluid (e.g., water) content. Once exposed to air, such material can desiccate such that the coupling pad component cannot correctly couple correctly with the transducer and sufficiently transfer ultrasound energy to provide the proper therapeutic effect. Further, a used coupling pad component is no longer clean and can harbor bacteria, which can lead to infections (e.g., a urinary tract or yeast infection). Some of these risks can be mitigated by labeling packing or user instructions with warnings against reuse of coupling pad components. However, a technological solution, such as an optical reader, may be more effective at eliminating these risks.

Another advantage of an optical reader system is that the optical code can store ultrasound parameters, such as for prescribed therapeutic treatments. For example, operating parameters (e.g., therapy duration, lockout duration, ultrasound frequency, duty cycle and/or intensity of the ultrasound energy) may be encoded in the optical code of the disposable component, thereby allowing a healthcare provider or patient to adjust the therapy by changing the disposable component. In one example, the healthcare provider may prescribe an initial disposable component that has a higher intensity or duty cycle and a "maintenance" disposable component with lower intensity to maintain the clinical benefit but at a lower power. In another example, a high-power disposable component that includes a code associated with controller instructions to operate using a higher intensity may be prescribed for patients that don't see a benefit when using a "standard" disposable component with a code associated with controller instructions to operate using a "standard" intensity settings. The changes in therapy may be affected by simply changing the disposable component rather than having to re-program the ultrasound device or have multiple versions of the ultrasound device available. In some cases, the device is provided with a set of different disposable components with codes for different therapeutic settings.

Figure 56A:
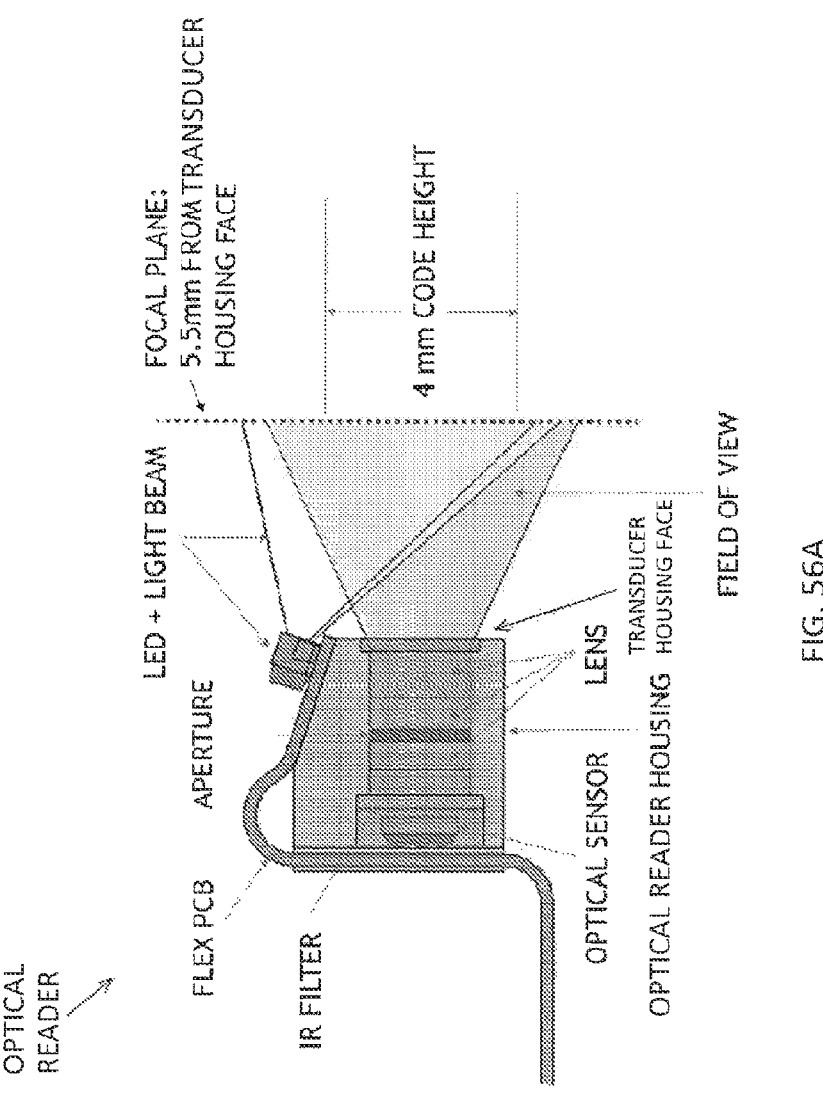
FIGS. 56A-56D show an embodiment of an optical reader and an optical code on a support ring.
Figure 56B:
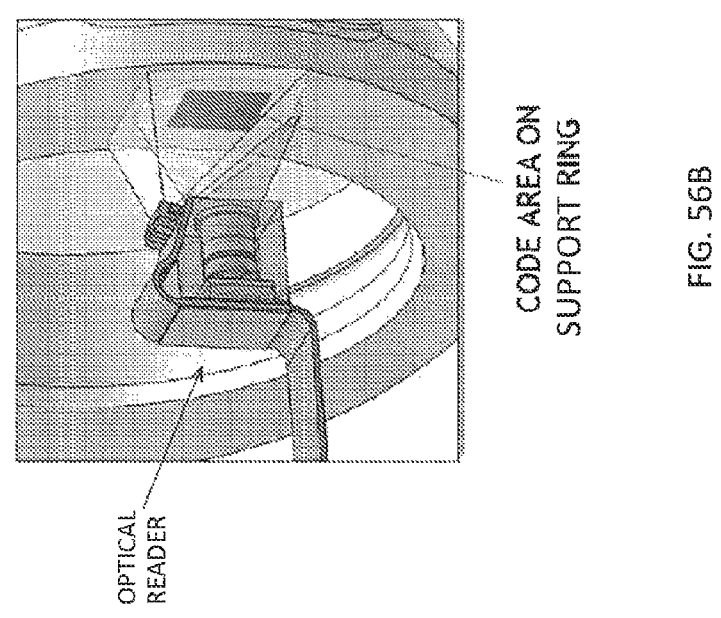

FIGS. 56A and 56B illustrate an example optical reader assembly, which can be incorporated into the ultrasound transducer component. In some embodiments, the code reader is an infrared light-based camera system. One or more illumination sources, such as a light emitting diode (LED) is configured to direct light beams through a window of the ultrasonic device housing so that the light can illuminate a code area on the coupling pad component. In some cases, one or more infrared (e.g., near infrared) LEDs may be preferred due to their energy efficiency, size and low cost. As shown in FIG. 56B, the code area of the coupling pad component may be on a proximal surface (relative to the transducer component) of the support ring of the coupling pad component. The code area of the coupling pad includes a readable code, such as a barcode (e.g., linear barcode or matrix (2D) barcode) or other coded image. One example of a 2D barcode is a quick response (QR) code. The code may be disposed on a surface of the coupling pad component (e.g., printed or painted on) or embedded within a material of the coupling pad component. In some embodiments, the code is engraved (e.g., laser engraved) into the coupling pad component. The code may be miniature in size. For example, the code may have an area ranging from about 1 $mm^2$ to about 50 $mm^2$. The code can include identifying information associated with the coupling pad component, such as manufacturing information and/or therapy parameters associated with using with the coupling pad component. Therapy parameters may include ultrasound frequency, duration of therapy, ultrasound power, duty cycle, intensity and duration of lockout. Coupling pad information may include a unique ID (e.g., to prevent re-use), expiration date, coupling gel material, attachment mechanism (e.g., to inform the controller to look for magnetic signal), version (e.g., to check for compatibility), Error checking code (e.g., to make sure the code was read correctly, such as a checksum or CRC code). The code may include information related to whether the coupling pad component has already been used. In some embodiments, the code has a data storage capacity ranging from about 5 b to about 3 Kb. In some embodiments, the code is encrypted. In some cases, the code includes information that is compressed, and the optical reader decompresses the compressed information, which is interpreted by decoder software of the ultrasound device.

Returning to FIG. 56A, light reflected from the code is focused by lens system, which can include one more lenses, apertures and/or filters (e.g., infrared filter), and which directs the reflected light to one or more optical sensors. The optical sensor(s) can include any type of image sensor, such as a complementary metal-oxide-semiconductor (CMOS) or charge-coupled device (CCD) image sensor. The lens system and optical sensor(s) may be housed within an optical reader housing. The sensor(s) can be operationally coupled to a printed circuit board (PCB). In some cases, the PCB is a flex PCB that is conformable to a desired shape. In the example shown, the flex PCB includes a first portion that is mounted on the back of the optical reader housing for optimal communication with the sensor(s), and a second portion that is mounted on a sidewall (e.g., top side) of the optical reader housing for proper placement of the illumination source (e.g., LED) that is operationally coupled to the flex PCB.

The optical reader can be adapted to reliably convey information in a confined, dark space with a short focal distance. The focal distance refers to a distance from the optical reader that the optical reader can reliably read a code. The focal distance can correspond to the distance from the optical assembly lens to a focal plane as shown in FIG. 56A. In some embodiments, the focal distance ranges from about 1 millimeter (mm) to about 12 mm (e.g., 1-12 mm, 1-6 mm, 2-12 mm, 3-7 mm, 2-6 mm, or 5-6 mm). The optical reader can be adapted to read a very small code. For example, a field of view of the optical reader can be adapted to read a code a particular size. In some embodiments, the code has a height ranging from about 2 mm to about 10 mm (e.g., 2-10 mm, 3-5 mm, 3-6 mm, 3-7 mm, 2-6 mm, or 2-9 mm).

Figure 56D:
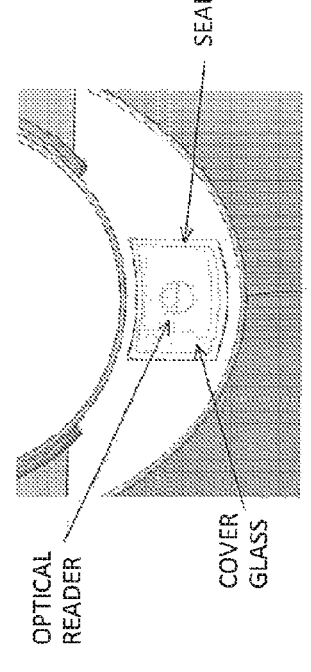
Figure 56C:
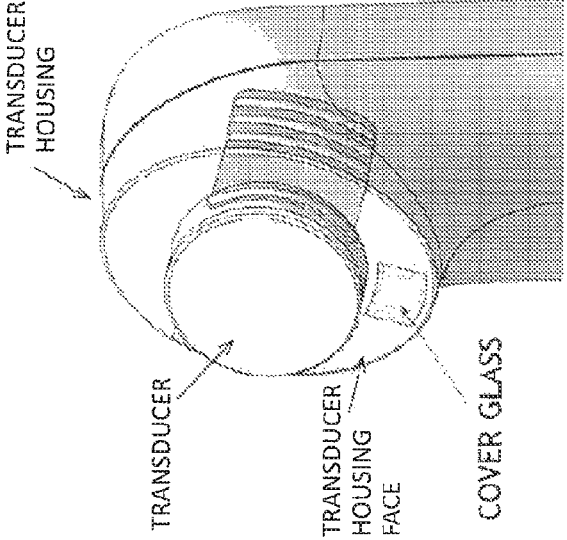

In some cases, the optical reader is enclosed within the transducer housing, such as illustrated in FIGS. 56C and 56D. The transducer housing can include a cover glass (also referred to as a window) through which light to and from the optical reader can be transmitted into and out of the transducer housing. The window can be made of a material sufficiently transparent for the optical reader to transmit and receive optical signals for reading the optical code. In some cases, the window is made of an optically transparent polymer and/or glass material. The interface between the window and the transducer housing is sealed (e.g., water-tight seal). In some cases, the seal may be formed during a molding (e.g., over-molding) or additive manufacturing process. In some cases, a gasket and/or sealant may run along the outer edge of the window to provide the seal. In some embodiments, the window is positioned on a generally annular or oval shaped transducer housing face at the head portion of the device. In some cases, the transducer housing face is adapted to contact the support ring of the contact pad, as described herein. The window can have any shape and size. In the example shown, the window has a near-rectangular shape with two curved sides corresponding to the curved annular or oval shape of the transducer housing face.

It should be noted that the features of the optical reader are specifically adapted for implementation with an ultrasonic vulvovaginal rejuvenation device and that conventional optical scanning technology may not be suitable for the device. For example, currently available barcodes may not be capable of storing the amount of data required in the limited space available on the coupling pad component. Additionally, conventional scanners typically include lasers and moving mirrors, which are fragile and thus prove challenging for alignment and long-term durability. Furthermore, the illumination source for the device should avoid the use of lasers, as these can be harmful to the human eye. The system should also avoid visible light systems, as these could be seen as invasive by the user. Additionally, conventional barcode scanners typically require a larger amount of physical space than the ultrasonic devices described herein can accommodate. Thus, the optical reader is adapted to operate in the small confined space with short focal distance and under low light conditions, as described herein.

In some cases, one or more ultrasound parameters of the ultrasound device may be set by reading the code on the disposable component. For example, the therapy time, intensity, frequency, duty cycle, pulse repetition rate and/or lockout time may be modified by the disposable component. This could be very useful for situations where a doctor may want to prescribe a therapy change. For the changes to be implemented, the patient may then only have to get a new disposable component with the new parameter information incorporated in the code. Different disposable components may have different codes to inform the reusable component to operate with different parameter settings. For example, a "high output" disposable component may have a code that informs the reusable component (controller) to use a relatively high power (e.g., 4 W) and a "regular dose" disposable that would cause the reusable component to output relatively intermediate power (e.g., 3.4 W).

Figure 57:
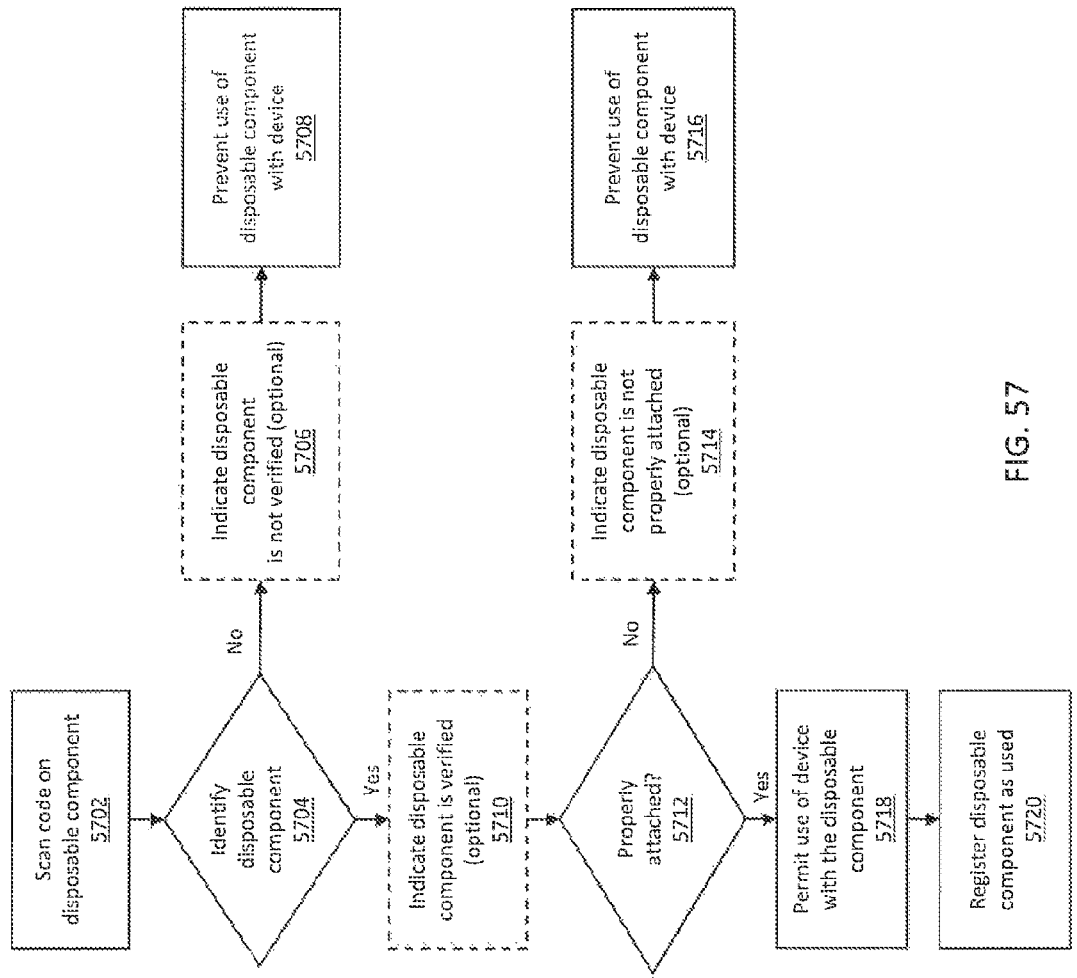
FIG. 57 shows a flowchart showing an example process for using an optical reader of an ultrasonic transducer device according to some embodiments.

FIG. 57 illustrates a flowchart indicating an example process for using an optical reader of an ultrasonic transducer device. To use the optical reader, the user can hold the transducer device and point the optical reader window toward an optical code on a disposable component (e.g., coupling pad component) to scan the optical code (5702). In some embodiments, the user activates the code reader using a switch (e.g., button) on the housing of the transducer device. In some embodiments, the button for activating the optical reader is the same as the power button. In other embodiments, the button for activating the optical reader is a different button as the power button. In some embodiments, the code reader automatically scans the optical code. In some embodiments, the code is in contact with the window or as far as about 20 mm away (e.g., between 0 mm and 20 mm away). In some embodiments, the code reader is adapted to scan and identify the code on or through packaging containing the disposable component (e.g., a blister pack).

The code reader then identifies the disposable component (5704) using the scanned code. Identifying the disposable component may involve determining whether the scanned code is associated with a verified disposable component (e.g., pre-approved and/or not used). Alternatively or additionally, identifying the disposable component may involve receiving process parameters associated with a particular therapeutic treatment, which can be stored and used by the device to deliver the particular therapeutic treatment to the user.

If the code is not identified by the code reader as being associated with a verified disposable component, the device may optionally indicate to the user that the disposable component is not verified (5706). Such indicator may be a visual and/or audible indicator. For example, a light on the device may turn on or off and/or a speaker of the device may produce a sound indicating the disposable component is not verified. If the disposable component is determined not be verified, the device will not permit the device to be used with the disposable component (5708). In some embodiments, the disposable component will not be verified if software (instructions carried out by the processor(s)) does not identify the code when compared to one or more databases of verified codes stored in storage and/or memory of the device. A verified code may be associated with a disposable component that has be pre-approved to meet required specifications for use with the device. A "counterfeit" disposable component may not have a code or may have a code that is not identified by the device as corresponding to a verified code in the database(s). Additionally or alternatively, a verified code may be associated with a disposable component that is determined to not to have been previously used. This can prevent the user from reusing a disposable component, which may harbor harmful pathogens and/or be dried out. The device may prevent use with an unverified disposable component by not turning on (e.g., preventing the transducer from activating) even if the unverified disposable component is attached to the head of the device.

If the code is identified by the code reader as being associated with a verified disposable component, the device may optionally indicate to the user that the disposable component is verified (5710). Such indicator may be a visual and/or audible indicator. The visual (e.g., a light) and/or audible (e.g., speaker sound) indicator may be different than the visual and/or audible indicator indicating that the device is not verified. When the user attaches the disposable component to the head portion of the device, the device can determine whether the disposable component is properly attached to the device (5712). Proper attachment may be determined by feedback from one or more sensors, such as one or more magnetic sensors, on the device or from the optical reader itself. If it is determined that the disposable component is not properly attached, the device may optionally indicate this to the user by a visual and/or audible indicator (5714). The visual (e.g., a light) and/or audible (e.g., speaker sound) indicator may be different than the visual and/or audible indicator indicating that the device is verified and/or not verified. If the disposable component is not properly attached, the user may be prevented from turning on the device (e.g., prevent the transducer from activating) until the disposable component is properly attached (5716). If the device determines that the disposable component is properly attached, the device may permit the user to use the device (e.g., turn on the transducer) with the attached disposable component (5718). After the user uses the disposable component, the disposable component can be registered by the device as being used in one or more databases stored in the device or accessible to the device (e.g., stored in a device external to the ultrasound device).

It should be noted that the device may include one or both of the processes of identifying the disposable component (5704) and determining whether the disposable component is properly attached (5712). That is, in some embodiments, the device can be adapted to identify the disposable component (5704) but not to determine whether the disposable component is properly attached (5712). Likewise, in some embodiments, the device can be adapted to determine whether the disposable component is properly attached (5712) but not to identify the disposable component (5704). In other embodiments, the device can be adapted to identify the disposable component (5704) and to determine whether the disposable component is properly attached (5712).

Figure 58:
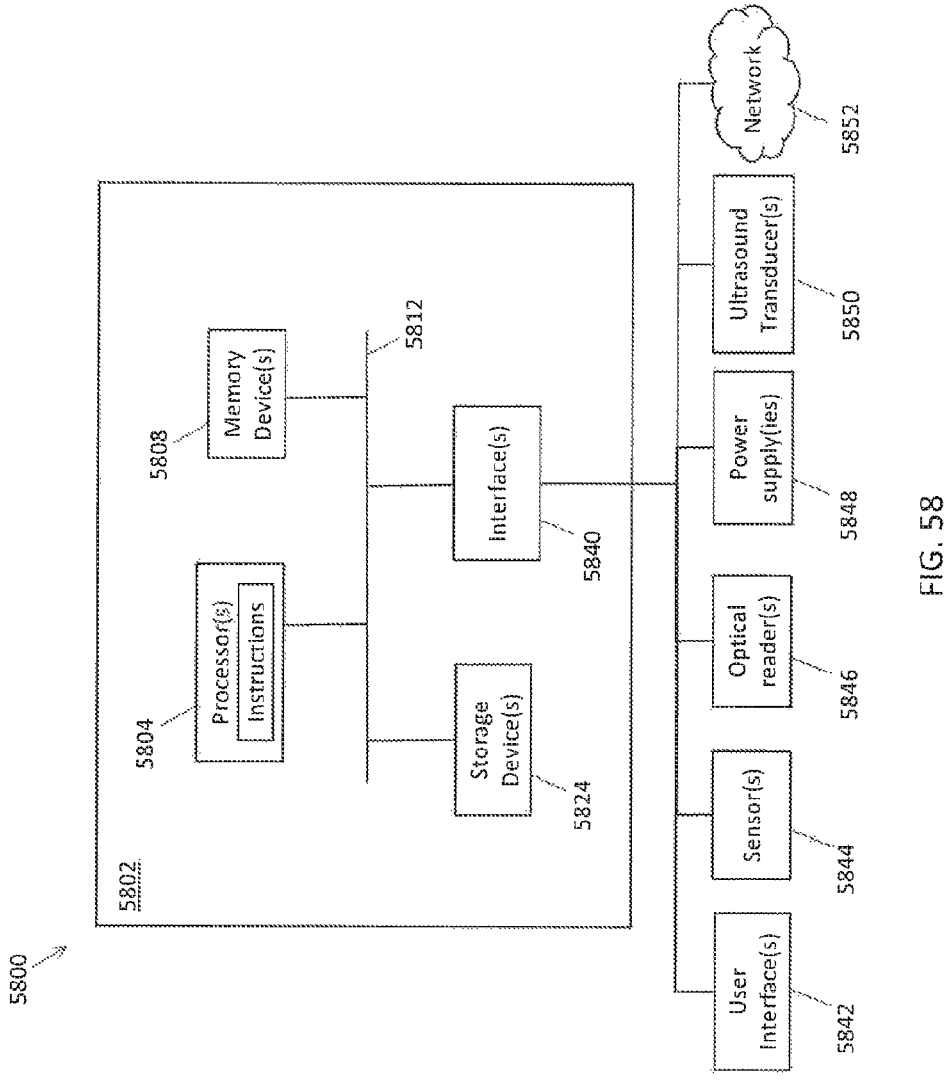
FIG. 58 shows an embodiment of a computing system for an ultrasonic transducer device according to some embodiments.

FIG. 58 illustrates a diagrammatic representation of an example computing system 5800, which may be part of any of the devices described herein. Computing system 5800 can include a computer 5802 having one or more processors 5804 configured to perform instructions (e.g., software instructions) according to any one or more of the functionalities, aspects, and/or methodologies of the present disclosure. For example, the processor(s) 5804 may be adapted to determine whether an optically readable code is associated with a pre-approved disposable component and/or a used disposable component. In some cases, the processor(s) 5804 may be adapted to determine whether a disposable component is properly attached to an ultrasound transducer component. The processor(s) 5804 may communicate with other components, for example, via bus 5812. Computer 5802 can also include one or more memory devices 5808 that communicates with the one or more processors 5804 and with other components, for example, via a bus 5812. The bus 5812 may include any of several types of bus structures including, but not limited to, a memory bus, a memory controller, a peripheral bus, a local bus, and any combinations thereof, using any of a variety of bus architectures.

Memory device(s) 5808 may include various components (e.g., machine-readable hardware storage media) including, but not limited to, a random access memory component (e.g., a static RAM "SRAM", a dynamic RAM "DRAM", etc.), a read only component, and any combinations thereof. In one example, the memory includes a basic input/output system (BIOS), including basic routines that help to transfer information between elements within computer 5802, such as during start-up, may be stored in memory device(s) 5808. Memory device(s) 5808 may also include (e.g., stored on one or more machine-readable hardware storage media) instructions (e.g., software) embodying any one or more of the aspects and/or methodologies of the present disclosure. In another example, memory 5808 may further include any number of program modules including, but not limited to, an operating system, one or more application programs, other program modules, program data, and any combinations thereof.

The computer 5802 may also include a storage device 5824, such as, but not limited to, a machine readable hardware storage medium. Storage device 5824 may be connected to bus 5812 by an appropriate interface, such as SCSI, advanced technology attachment (ATA), serial ATA, universal serial bus (USB), IEEE 1394 (FIREWIRE), I2c, and any combinations thereof. In one example, storage device 5824 (or one or more components thereof) may be removably interfaced with computer 5802 (e.g., via an external port connector). Storage device 5824 can include a computer readable medium to provide nonvolatile and/or volatile storage of machine-readable instructions, data structures, program modules, and/or other data for computer 5802. In one example, software instructions may reside, completely or partially, within computer readable medium of the storage device 5824. Additionally or alternatively, software instructions may reside, completely or partially, within processor(s) 5804.

The computer 5802 may also include one or more input/output (I/O) interfaces 5040 for operationally coupling the computer 5802 to one or more components of the ultrasonic transducer device and/or one or more devices other than the ultrasonic transducer device. The I/O interface(s) may include wired connections and/or wireless connections. The computer 5802 may be connected to one or more user interfaces 5842, which may include one or more controls (e.g., buttons) for controlling one or more functions of the device. For example, a power button may turn power to the ultrasonic transducer device on/off, and a code reader activation button may activate the code reader. In some examples, the user interface(s) 5842 include input/output devices separate from the ultrasonic transducer device. For example, in some cases, the I/O interface(s) may permit user input and/or output via one or more external computers, such as a tablet, laptop and/or smart phone. In some examples, the computer 5802 may be adapted to receive input from a touch screen, keyboard and/or microphone of a separate device(s) and/or sent output to a display, printer and/or speaker of a separate device(s). Example output data may include data collected by the ultrasonic transducer device and/or identification data associated with the ultrasonic transducer device and disposable component.

The computer 5802 may be operationally coupled to one or more ultrasound transducers 5850. The ultrasound transducer(s) 5850 may be adapted to generate ultrasound energy having a particular intensity, frequency, duty cycle, etc. based on the particular application. In the case of vaginal rejuvenation, the transducer(s) may be configured to generated ultrasound energy configured to penetrate tissue to a depth of about 3-5 cm. In such applications, the transducer(s) may be configured to generate ultrasound waves having an intensity ranging from about 0.25 W/cm$^2$ to about 5 W/cm$^2$ and/or a frequency ranging from about 0.5 MHz to about 4 MHz. In some cases, the ultrasound transducer(s) 5850 may be configured to generate a high intensity focused ultrasound (HIFU) with a focal area of high heat. HIFU applications may include treatments to destroy tissues (e.g., cancer cells, tumors) or in aesthetic applications (e.g., tightening skin).

The computer 5802 may be operationally coupled to one or more sensors 5844, for example, to provide feedback to the processor(s) 5804. The sensor(s) 5844 can include those adapted to detect proper attachment of the disposable component to the ultrasonic transducer device, such as a magnetic-based sensor assembly. In some cases, the sensor(s) 5844 include temperature sensor(s) to measure tissue temperature. The computer 5802 may be operationally coupled to one or more optical readers 5846, for example, to scan a code on a disposable component. The optical reader(s) 5846 may include an infrared light-based camera system for illuminating and detecting an optical code on the disposable component, which the processor(s) can use to determine whether the disposable component is verified and/or unused. The computer 5802 may be operationally coupled to one or more power supplies 5848 to provide power to the computer 5802 and/or other components of the ultrasonic transducer device. In some examples, the power supply(ies) include one or more batteries within the housing of the ultrasonic transducer device. The battery(ies) may be rechargeable via a charger (e.g., inductive charger). Alternatively or additionally, the ultrasonic transducer device may be configured to receive power from an external source (e.g., electrical outlet). In some embodiments, the computer 5802 may be configured to connect directly or indirectly (e.g., through one or more devices) to a wireless network 5852. The network 5852 may be a wide area network (e.g., the Internet, an enterprise network), a local area network, a telephone network, a data network associated with a telephone/voice provider, a direct connection between two computing devices, and any combinations thereof.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected," "attached" or "coupled" to another feature or element, it can be directly connected, attached or coupled to the other feature or element or intervening features or elements may be present. In contrast, when a feature or element is referred to as being "directly connected," "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims that follow, unless the context requires otherwise, the word "comprise," and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for applying ultrasonic energy to a subject, comprising:

a plurality of disposable components adapted to contact tissue of the subject comprising a plurality of optically readable codes, wherein the plurality of optically readable codes includes encoded identification information associated with the disposable component; and a reusable component comprising an ultrasound transducer assembly and a code reader assembly adapted to detect the plurality of optically readable codes of the plurality of disposable components, wherein the reusable component is adapted to verify that a one of the plurality of disposable components corresponds to a pre-approved disposable component, that the one of the plurality of disposable components is unused, or that the one of the plurality of disposable components corresponds to a pre-approved disposable component and is unused, wherein when the reusable component and the one of the plurality of disposable components are attached together, the ultrasound transducer assembly and the one of the plurality of disposable components are adapted to deliver ultrasound energy to the subject based on parameters for prescribed therapeutic treatments stored in the plurality of optically readable codes, wherein the parameters for the prescribed therapeutic treatment stored in the plurality of optically readable codes include therapy duration, lockout duration, ultrasound frequency, duty cycle, and intensity of the ultrasonic energy; wherein the one of plurality of disposable components having the one of the plurality of optically readable codes is configured to be swappable with another one of the plurality of disposable components having a different one of the plurality of optically readable codes to change the prescribed therapeutic treatment.

2. The device of claim 1, wherein the reusable component and the plurality of disposable components are adapted to deliver the ultrasound energy for imaging internal body structures of the subject.

3. The device of claim 1, wherein the reusable component and the plurality of disposable components are adapted to deliver a therapeutic ultrasound energy to one or more tissues of the subject including vaginal tissue of the subject.

4. The device of claim 1, wherein the reusable component and the plurality of disposable components are adapted to deliver a therapeutic ultrasound energy to the subject's genital tissue.

5. The device of claim 1, wherein the disposable component includes a coupling pad adapted to contact external genital tissue around the subject's vagina.

6. The device of claim 1, wherein the code reader assembly is adapted to emit light to illuminate the optically readable code.

7. The device of claim 1, wherein the optical reader assembly operates at a focal distance ranging from about 1 millimeter (mm) to about 12 mm.

8. The device of claim 1, wherein the plurality of disposable components include a coupling pad comprising a gel.

9. The device of claim 1, wherein a housing of the reusable component includes a window through which the code reader assembly transmits and receives light.

10. The device of claim 9, wherein the window is on a head portion of the reusable component, the head portion including a transducer head of the ultrasound transducer assembly.

11. The device of claim 10, wherein the window is on a transducer face of the head portion, wherein the transducer face is adapted to contact a support of the one of the plurality of disposable components when the one of the plurality of disposable components is properly attached to the reusable component.

12. The device of claim 1, wherein the device is configured to provide feedback to a user indicating that the one of the plurality of disposable components is properly attached to the reusable component.

13. A method of applying ultrasonic energy to a subject, the method comprising:

verifying a one of a plurality of optically readable codes on one of a plurality of disposable components using an optical reader assembly of an ultrasound device, wherein the verifying includes determining that the one of the plurality of disposable components corresponds to a pre-approved disposable component, that the one of the plurality of disposable components is unused, or that the one of the plurality of disposable components corresponds to a pre-approved disposable component and is unused;

delivering the ultrasonic energy to the subject based on parameters for prescribed therapeutic treatment stored in the one of the plurality of optically readable codes using the ultrasonic device with the one of the plurality of disposable components attached thereto contacting tissue of the subject, wherein delivering the ultrasonic energy to the subject based on the parameters for the prescribed therapeutic treatment stored in the one of the plurality of optically readable codes includes delivering the ultrasonic energy based on parameters stored in the one of the plurality of optically readable codes for therapy duration, lockout duration, ultrasound frequency, duty cycle, and intensity of the ultrasonic energy; and changing the prescribed therapeutic treatment by swapping the one of the plurality of disposable components having the one of the plurality of optically readable codes with another one of the plurality of disposable components having another one of the plurality of optically readable codes.

14. The method of claim 13, wherein the ultrasonic energy is adapted to deliver a therapeutic dose of ultrasonic energy to one or more tissues of the subject including vaginal tissue of the subject.

15. The method of claim 14, wherein delivering the therapeutic dose of ultrasonic energy increases blood flow to internal vaginal tissue up to 300% above a baseline level of blood flow to the internal vaginal tissue such that the increased level of blood flow to the internal vaginal tissue persists after delivery of therapeutic ultrasonic energy ceases.

16. The method of claim 15, wherein the plurality of disposable components includes a coupling pad comprising a deformable coupling structure adapted to contact external genital tissue around the subject's vagina.

17. The method of claim 13, further comprising determining that the one of the plurality of disposable components is properly attached to the ultrasound device prior to delivering the ultrasonic energy to the subject.

18. The method of claim 17, wherein the determining includes verifying sufficient contact between the disposable component and the ultrasound device.

19. The method of claim 17, wherein the determining includes detecting attachment of the disposable component to the ultrasound device using one or more magnetoresistive sensors.

\* \* \* \* \*